(12) United States Patent
Mann et al.

(10) Patent No.: US 8,160,702 B2
(45) Date of Patent: *Apr. 17, 2012

(54) METHOD FOR DIGITAL CARDIAC RHYTHM MANAGEMENT

(75) Inventors: Brian Mann, Edgartown, MA (US); James S. Whiting, Los Angeles, CA (US); Neal L. Eigler, Pacific Palisades, CA (US)

(73) Assignee: Pacesetter, Inc., Sylmar, CA (US)

( * ) Notice: Subject to any disclaimer, the term of this patent is extended or adjusted under 35 U.S.C. 154(b) by 296 days.

This patent is subject to a terminal disclaimer.

(21) Appl. No.: 12/565,672

(22) Filed: Sep. 23, 2009

(65) Prior Publication Data

US 2010/0016918 A1    Jan. 21, 2010

Related U.S. Application Data

(63) Continuation of application No. 11/027,646, filed on Dec. 30, 2004, now Pat. No. 7,616,991, which is a continuation of application No. 11/015,336, filed on Dec. 17, 2004, now abandoned.

(60) Provisional application No. 60/531,238, filed on Dec. 19, 2003.

(51) Int. Cl.
    *A61N 1/00* (2006.01)
(52) U.S. Cl. ............................................. 607/9
(58) Field of Classification Search ................ 607/9
    See application file for complete search history.

(56) References Cited

U.S. PATENT DOCUMENTS

| | | | |
|---|---|---|---|
| 3,672,352 A | 6/1972 | Summers | |
| 4,038,990 A | 8/1977 | Thompson | |
| 4,679,144 A | 7/1987 | Cox et al. | |
| 4,830,006 A | 5/1989 | Haluska et al. | |
| 4,850,371 A | 7/1989 | Broadhurst et al. | |
| 4,877,032 A | 10/1989 | Heinze et al. | |
| 4,899,751 A | 2/1990 | Cohen | |
| 4,899,752 A | 2/1990 | Cohen | |
| 4,899,758 A | 2/1990 | Finkelstein et al. | |
| 4,967,749 A | 11/1990 | Cohen | |
| 4,984,572 A | 1/1991 | Cohen | |
| 5,103,828 A | 4/1992 | Sramek | |

(Continued)

FOREIGN PATENT DOCUMENTS

EP        0 472 411 A1    2/1992

(Continued)

OTHER PUBLICATIONS

Amendment of Oct. 18, 2007, submitted in U.S. Appl. No. 11/026,951, filed Dec. 30, 2004.

(Continued)

*Primary Examiner* — George Manuel
(74) *Attorney, Agent, or Firm* — Knobbe Martens Olson & Bear LLP

(57) ABSTRACT

A cardiac rhythm management apparatus includes a proximal housing, a distal housing and a lead. The proximal housing includes a first energy storage device. The distal module is implantable within a patient's heart, and includes a second energy storage device, at least one electrode, and a control module. The control module controls the delivery of at least one electrical stimulus from the second energy storage device to a location in communication with the patient's heart. The lead connects the proximal housing to the distal module and is configured to communicate one or more digital signals between the proximal housing and the distal module.

20 Claims, 38 Drawing Sheets

U.S. PATENT DOCUMENTS

| | | | |
|---|---|---|---|
| 5,113,869 A | 5/1992 | Nappholz et al. |
| 5,129,394 A | 7/1992 | Mehra |
| 5,163,429 A | 11/1992 | Cohen |
| 5,190,528 A | 3/1993 | Fonger et al. |
| 5,314,418 A | 5/1994 | Takano et al. |
| 5,324,327 A | 6/1994 | Cohen |
| 5,368,040 A | 11/1994 | Carney |
| 5,372,607 A | 12/1994 | Stone et al. |
| 5,398,692 A | 3/1995 | Hickey |
| 5,423,873 A | 6/1995 | Neubauer et al. |
| 5,464,434 A | 11/1995 | Alt |
| 5,498,524 A | 3/1996 | Hall |
| 5,535,752 A | 7/1996 | Halperin et al. |
| 5,566,680 A | 10/1996 | Urion et al. |
| 5,593,430 A | 1/1997 | Renger |
| 5,626,621 A | 5/1997 | Skolund et al. |
| 5,693,075 A | 12/1997 | Plicchi et al. |
| 5,697,375 A | 12/1997 | Hickey |
| 5,697,958 A | 12/1997 | Paul et al. |
| 5,700,283 A | 12/1997 | Salo |
| 5,704,352 A | 1/1998 | Tremblay et al. |
| 5,743,267 A | 4/1998 | Nikolic et al. |
| 5,749,909 A | 5/1998 | Schroeppel et al. |
| 5,752,976 A | 5/1998 | Duffin et al. |
| 5,758,652 A | 6/1998 | Nikolic |
| 5,782,898 A | 7/1998 | Dahl et al. |
| 5,861,003 A | 1/1999 | Latson et al. |
| 5,861,018 A | 1/1999 | Feierbach |
| 5,904,708 A | 5/1999 | Goedeke |
| 5,919,210 A | 7/1999 | Lurie et al. |
| 5,921,935 A | 7/1999 | Hickey |
| 5,935,158 A | 8/1999 | Holmstrom et al. |
| 5,976,174 A | 11/1999 | Ruiz |
| 5,999,848 A | 12/1999 | Gord et al. |
| 6,024,704 A | 2/2000 | Meador et al. |
| 6,024,756 A | 2/2000 | Huebsch et al. |
| 6,112,116 A | 8/2000 | Fischell et al. |
| 6,120,442 A | 9/2000 | Hickey |
| 6,152,885 A | 11/2000 | Taepke |
| 6,163,723 A | 12/2000 | Roberts et al. |
| 6,223,081 B1 | 4/2001 | Kerver |
| 6,223,087 B1 | 4/2001 | Williams |
| 6,234,973 B1 | 5/2001 | Meador et al. |
| 6,272,379 B1 | 8/2001 | Fischell et al. |
| 6,272,382 B1 | 8/2001 | Faltys et al. |
| 6,277,078 B1 | 8/2001 | Porat et al. |
| 6,309,350 B1 | 10/2001 | Van Tassel et al. |
| 6,328,699 B1 | 12/2001 | Eigler et al. |
| 6,381,493 B1 | 4/2002 | Stadler et al. |
| 6,409,674 B1 | 6/2002 | Brockway et al. |
| 6,418,348 B1 | 7/2002 | Witte |
| 6,424,867 B1 | 7/2002 | Snell et al. |
| 6,473,653 B1 | 10/2002 | Schallhorn et al. |
| 6,480,744 B2 | 11/2002 | Ferek-Petric |
| 6,501,983 B1 | 12/2002 | Natarajan et al. |
| 6,529,777 B1 | 3/2003 | Holmstrom et al. |
| 6,553,263 B1 | 4/2003 | Meadows et al. |
| 6,574,510 B2 | 6/2003 | Von Arx et al. |
| 6,580,946 B2 | 6/2003 | Struble |
| 6,645,143 B2 | 11/2003 | Van Tassel et al. |
| 6,711,440 B2 | 3/2004 | Deal et al. |
| 6,760,628 B2 | 7/2004 | Weiner et al. |
| 6,824,521 B2 | 11/2004 | Rich et al. |
| 7,013,178 B2 | 3/2006 | Reinke et al. |
| 7,115,095 B2 | 10/2006 | Eigler et al. |
| 7,137,953 B2 | 11/2006 | Eigler et al. |
| 7,211,048 B1 | 5/2007 | Najafi et al. |
| 7,225,034 B2 | 5/2007 | Ries et al. |
| 7,286,882 B2 | 10/2007 | Cole |
| 7,450,996 B2 * | 11/2008 | MacDonald et al. ......... 607/115 |
| 7,616,991 B2 | 11/2009 | Mann et al. |
| 2002/0013613 A1 | 1/2002 | Haller et al. |
| 2002/0051551 A1 | 5/2002 | Leysieffer et al. |
| 2002/0105436 A1 | 8/2002 | Bell et al. |
| 2002/0116034 A1 | 8/2002 | Miller et al. |
| 2002/0133200 A1 | 9/2002 | Weiner et al. |
| 2002/0188329 A1 | 12/2002 | Struble |
| 2003/0055344 A1 | 3/2003 | Eigler et al. |
| 2003/0055345 A1 | 3/2003 | Eigler et al. |
| 2003/0055461 A1 | 3/2003 | Girouard et al. |
| 2003/0139785 A1 | 7/2003 | Riff et al. |
| 2004/0019285 A1 | 1/2004 | Eigler et al. |
| 2004/0106874 A1 | 6/2004 | Eigler et al. |
| 2004/0116992 A1 | 6/2004 | Wardle et al. |
| 2004/0147969 A1 | 7/2004 | Mann et al. |
| 2004/0167580 A1 | 8/2004 | Mann et al. |
| 2004/0193021 A1 | 9/2004 | Zdeblick et al. |
| 2005/0080460 A1 | 4/2005 | Wang et al. |
| 2005/0136385 A1 | 6/2005 | Mann et al. |
| 2005/0165456 A1 | 7/2005 | Mann et al. |
| 2005/0288596 A1 | 12/2005 | Eigler et al. |
| 2005/0288604 A1 | 12/2005 | Eigler et al. |
| 2005/0288722 A1 | 12/2005 | Eigler et al. |
| 2006/0009810 A1 | 1/2006 | Mann et al. |
| 2006/0079793 A1 | 4/2006 | Mann et al. |
| 2006/0149324 A1 | 7/2006 | Mann et al. |
| 2006/0149330 A1 | 7/2006 | Mann et al. |
| 2006/0149331 A1 | 7/2006 | Mann et al. |
| 2007/0032831 A1 | 2/2007 | Eigler et al. |

FOREIGN PATENT DOCUMENTS

| | | |
|---|---|---|
| EP | 1 050 265 A2 | 11/2000 |
| EP | 1 057 448 A1 | 12/2000 |
| WO | WO 96/11722 | 4/1996 |
| WO | WO 99/56812 | 11/1999 |
| WO | WO 2004/066814 A2 | 8/2004 |

OTHER PUBLICATIONS

Amendment of Jan. 16, 2007, submitted in U.S. Appl. No. 11/027,598, filed Dec. 30, 2004.

Amendment of Sep. 18, 2007, submitted in, commonly assigned U.S. Patent No. 7,616,991, filed Dec. 30, 2004.

Amendment of Sep. 27, 2007, submitted in U.S. Appl. No. 11/015,336, filed Dec. 17, 2004.

Bailey, Steve, Device Tracks Ailing Hearts, online article at www.enquirer.com, Aug. 24, 2000.

U.S. Appl. No. 11/015,336, filed Dec. 17, 2004, titled Digital Electrode for Cardiac Rhythm Management. Inventors: Mann et al. The specification is the same as the present application. Claims were submitted in the parent application, U.S. Appl. No. 11/015,336, filed Dec. 17, 2004.

U.S. Appl. No. 11/026,951, filed Dec. 30, 2004, titled Digitally Controlled Cardiac Rhythm Management. Inventors: Mann et al. The specification is the same as the present application. Claims were submitted in the parent application, U.S. Appl. No. 11/015,336, filed Dec. 17, 2004.

U.S. Appl. No. 11/027,598, filed Dec. 30, 2004, titled Flexible Lead for Digital Cardiac Rhythm Management. Inventors: Mann et al. The specification is the same as the present application. Claims were submitted in the parent application, U.S. Appl. No. 11/015,336, filed Dec. 17, 2004.

U.S. Patent No. 7,616,991, filed Dec. 30, 2004, titled Method for Digital Cardiac Rhythm Management. Inventors: Mann et al. The specification is the same as the present application. Claims were submitted in the parent application, U.S. Appl. No. 11/015,336, filed Dec. 17, 2004.

U.S. Appl. No. 11/027,820, filed Dec. 30, 2004, titled Cardiac Rhythm Management With Interchangeable Components. Inventors: Mann et al. The specification is the same as the present application. Claims were submitted in the parent application, U.S. Appl. No. 11/015,336, filed Dec. 17, 2004.

Final Office Action of Apr. 18, 2006, commonly assigned U.S. Appl. No. 11/027,598, filed Dec. 30, 2004.

Final Office Action of Dec. 23, 2008, commonly assigned U.S. Appl. No. 11/027,598, filed Dec. 30, 2004.

Final Office Action of Jan. 2, 2008, commonly assigned U.S. Patent No. 7,616,991, filed Dec. 30, 2004.

Final Office Action of Jul. 11, 2008, commonly assigned U.S. Appl. No. 11/026,951, filed Dec. 30, 2004.

Final Office Action of Jul. 18, 2008, commonly assigned U.S. Appl. No. 11/026,951, filed Dec. 30, 2004.

Final Office Action of Jul. 27, 2007, commonly assigned U.S. Appl. No. 11/015,336, filed Dec. 17, 2004.
Final Office Action of May 1, 2008, commonly assigned U.S. Appl. No. 11/027,820, filed Dec. 30, 2004.
Final Office Action of May 23, 2006, commonly assigned U.S. Appl. No. 11/015,336, filed Dec. 17, 2004.
Final Office Action of Sep. 17, 2007, commonly assigned U.S. Appl. No. 11/027,598, filed Dec. 30, 2004.
International Search Report and Written Opinion of Mar. 30, 2006, commonly assigned PCT Application No. PCT/US04/42694, filed Dec. 17, 2004.
Lowry, Fran, Heart failure patients, doctors linked in cyberspace, online article at www.theheart.org, Sep. 14, 2000.
Neergaard, Lauran, Internet assists in daily heart monitoring, CNN.com health web page: Feb. 22, 2000, (copyright 2000, Cable News Network).
Non-final Office Action of Aug. 9, 2005, commonly assigned U.S. Appl. No. 11/027,598, filed Dec. 30, 2004.
Non-final Office Action of Dec. 10, 2007, commonly assigned U.S. Appl. No. 11/027,598, filed Dec. 30, 2004.
Non-final Office Action of Dec. 12, 2008, commonly assigned U.S. Appl. No. 11/027,820, filed Dec. 30, 2004.
Non-final Office Action of Dec. 13, 2007, commonly assigned U.S. Appl. No. 11/015,336, filed Dec. 17, 2004.
Non-final Office Action of Dec. 17, 2008, commonly assigned U.S. Appl. No. 11/026,951, filed Dec. 30, 2004.
Non-final Office Action of Dec. 28, 2007, commonly assigned U.S. Appl. No. 11/026,951, filed Dec. 30, 2004.
Non-final Office Action of Dec. 4, 2006, commonly assigned U.S. Appl. No. 11/015,336, filed Dec. 17, 2004.
Non-final Office Action of Jan. 14, 2009, commonly assigned U.S. Appl. No. 11/015,336, filed Dec. 17, 2004.
Non-final Office Action of Jan. 23, 2007, commonly assigned U.S. Appl. No. 11/026,951, filed Dec. 30, 2004.
Non-final Office Action of Jun. 19, 2007, commonly assigned U.S. Patent No. 7,616,991, filed Dec. 30, 2004.
Non-final Office Action of Jun. 20, 2008, commonly assigned U.S. Patent No. 7,616,991, filed Dec. 30, 2004.
Non-final Office Action of Oct. 11, 2007, in U.S. Appl. No. 11/027,820, filed Dec. 30, 2004.
Non-final Office Action of Oct. 16, 2006, commonly assigned U.S. Appl. No. 11/027,598, filed Dec. 30, 2004.
Non-final Office Action of Sep. 8, 2005, commonly assigned U.S. Appl. No. 11/015,336, filed Dec. 17, 2004.
Originally filed claims, submitted in, commonly assigned U.S. Appl. No. 11/027,820, filed Dec. 30, 2004.
Soufer, Robert, Treating a Sick Heart, Heart Disease, Nova Online web page (copyright 1997, WGBH).
Steinhaus, David M. et al., Initial Experience with an Implantable Hemodynamic Monitor, Circulation, vol. 93, No. 4, pp. 745-752, Feb. 15, 1996.

* cited by examiner

FIG. 6A Right Atrial Pressure Waveforms

Low mean atrial pressure
    1. Hypovolemia
    2. Improper zeroing of the transducer
Elevated mean atrial pressure
    1. Intravascular volume overload states
    2. Right ventricular failure due to valvular disease (tricuspid or pulmonic stenosis or regurgitation)
    3. Right ventricular failure due to myocardial disease (right ventricular ischemia, cardiomyopathy)
    4. Right ventricular failure due to left heart failure (mitral stenosis/regurgitation, aortic stenosis/regurgitation, cardiomyopathy, ischemia)
    5. Right ventricular failure due to increased pulmonary vascular resistance (pulmonary embolism, chronic obstructive pulmonary disease, primary pulmonary hypertension)
    6. Pericardial effusion with tamponade physiology
    7. Obstructive atrial myxoma
Elevated a wave (any increase to ventricular filling)
    1. Tricuspid stenosis
    2. Decreased ventricular compliance due to ventricular failure, pulmonic valve stenosis, or pulmonary hypertension
Cannon a wave
    1. Atrial-ventricular asynchrony (atria contract against a closed tricuspid valve, as during complete heart block following premature ventricular contraction, during ventricular tachycardia, with ventricular pacemaker)
Absent a wave
    1. Atrial fibrillation or atrial standstill
    2. Atrial flutter
Elevated v wave
    1. Tricuspid regurgitation
    2. Right ventricular heart failure
    3. Reduced atrial compliance (restrictive myopathy)
a wave equal to v wave
    1. Tamponade
    2. Constrictive pericardial disease
    3. Hypervolemia
Prominent x descent
    1. Tamponade
    2. Subacute constriction and possibly chronic constriction
    3. Right ventricular ischemia with preservation of atrial contractility
Prominent y descent
    1. Constrictive pericarditis
    2. Restrictive myopathies
    3. Tricuspid regurgitation
Blunted x descent
    1. Atrial fibrillation
    2. Right atrial ischemia
Blunted y descent
    1. Tamponade
    2. Right ventricular ischemia
    3. Tricuspid stenosis
Miscellaneous abnormalities
    1. Kussmaul's sign (inspiratory rise or lack of decline in right atrial pressure)-constrictive pericarditis, right ventricular ischemia
    2. Equalization ($\leq$5 mm Hg) of mean right atrial, right ventricular diastolic, pulmonary artery diastolic, pulmonary capillary wedge, and pericardial pressures in tamponade
    3. M or W patterns: right ventricular ischemia, pericardial constriction, congestive heart failure
    4. Ventricularization of the right atrial pressure: severe tricuspid regurgitation
    5. Saw tooth pattern: atrial flutter
    6. Dissociation between pressure recording and intracardiac ECG: Ebstein's anomaly

*Left Atrial Pressure/Pulmonary Capillary Wedge Pressure Waveforms*

Low mean atrial pressure
    1. Hypovolemia
    2. Improper zeroing of the transducer
Elevated mean atrial pressure
    1. Intravascular volume overload states
    2. Left ventricular failure due to valvular disease (mitral or aortic stenosis or regurgitation)
    3. Left ventricular failure due to myocardial disease (ischemia or cardiomyopathy)
    4. Left ventricular failure due to systemic hypertension
    5. Pericardial effusion with tamponade physiology
    6. Obstructive atrial myxoma
Elevated *a* wave (any increase to ventricular filling)
    1. Mitral stenosis
    2. Decreased ventricular compliance due to ventricular failure, aortic valve stenosis, or systemic hypertension
Cannon *a* wave
    1. Atrial-ventricular asynchrony (atria contract against a closed mitral valve, as during complete heart block following premature ventricular contraction, during ventricular tachycardia, with ventricular pacemaker)
Absent *a* wave
    1. Atrial fibrillation or atrial standstill
    2. Atrial flutter
Elevated *v* wave
    1. Mitral regurgitation
    2. Left ventricular heart failure
    3. Ventricular septal defect
*a* wave equal to *v* wave
    1. Tamponade
    2. Constrictive pericardial disease
    3. Hypervolemia
Prominent *x* descent
    1. Tamponade
    2. Subacute constriction and possibly chronic constriction
    3. Right ventricular ischemia with preservation of atrial contractility
Prominent *y* descent
    1. Constrictive pericarditis
    2. Restrictive myopathies
    3. Mitral regurgitation
Blunted *x* descent
    1. Atrial fibrillation
    2. Atrial ischemia
Blunted *y* descent
    1. Tamponade
    2. Ventricular ischemia
    3. Mitral stenosis
Pulmonary capillary wedge pressure not equal to left ventricular end-diastolic pressure
    1. Mitral stenosis
    2. Left atrial myxoma
    3. Cor triatriatum
    4. Pulmonary venous obstruction
    5. Decreased ventricular compliance
    6. Increased pleural pressure
    7. Placement of catheter in a nondependent zone of lung

*FIG. 6B*

*Pulmonary Artery Pressure Waveforms*

Elevated systolic pressure
    1. Primary pulmonary hypertension
    2. Mitral stenosis or regurgitation
    3. Congestive heart failure
    4. Restrictive myopathies
    5. Significant left to right shunt
    6. Pulmonary disease (pulmonary embolism, chronic obstructive pulmonary disease)

Reduced systolic pressure
    1. Hypovolemia
    2. Pulmonary artery stenosis
    3. Sub- or supravalvular stenosis
    4. Ebstein's anomaly
    5. Tricuspid stenosis
    6. Tricuspid atresia Reduced pulse pressure
    1. Right heart ischemia
    2. Right ventricular infarction
    3. Pulmonary embolism
    4. Tamponade Bifid pulmonary artery waveform
    1. Large left atrial *v* wave transmitted backward (i.e., MR)

Pulmonary artery diastolic pressure greater than pulmonary capillary wedge pressure
    1. Pulmonary disease
    2. Pulmonary embolus
    3. Tachycardia

| PARAMETERS MEASURED | Mean | | | Respiratory Component | | Cardiac Component | | | Intracardiac ECG | | Core Temp |
|---|---|---|---|---|---|---|---|---|---|---|---|
| DIAGNOSIS | RA | LA | RA-LA | RA | LA | RA | LA | HR | Rhythm | ST segment | |
| Cardiac hemodynamics | | | | | | | | | | | |
| CHF -compensated | ⇕ | ⇕ | ⇕ | | | | | | | | |
| CHF-mild | ↑↑ | ↑↑ | ↑↑ | | | | ↑↓∀ | ⇕ | | | ← |
| CHF-moderate | ↑↑↑ | ↑↑↑ | ↑↑↑ | | ↓↑ | | ↑↓∀ | ⇕ | | | ← |
| CHF - severe | ↑↑↑∀t ↓ | ↑↑↑∀t ↓ | ↑↑↑∀t ↓ | ↓↑ | ↓↑ | | ↑↓∀ | | | | |
| CHF- overtreated | ↑↑ ∀t | ↑↑ ∀t | ↑↑ ∀t | | | | ↑↑ | | | | |
| CHF - mitral regurgitations | ↑↑ ∀t | ↑↑ ∀t | ↑↑ ∀t | | | | | | | | |
| CHF-rapid onset | ↑↑ | ↑↑ | ≈0 | | | | | | | | |
| CHF- acute mitral regurgitations | ↑↑ | ≥↑ | ≥↑ | | | | ↑↑ ∀t | | | | |
| Cardiac tamponade | | | | | | Blunted-y-descent | | ⇕ | | | |
| Myocardial ischemia | | | | | | | | | SR | ∪alternans | |
| Cardiac rhythm | | | | | | | | | | | |
| Normal Sinus Rhythm | | | | | | | | 50-100 | SR | ↑ʋ | |
| Sinus Tachycardia | | | | | | | | >100 | SR | | |
| Sinus Bradycardia | | | | | | | | <50 | SR | | |
| Supraventricular Tachycardia | | | | | | | | >120 | Reg QRS <110 msec | | |
| Atrial Fibrillation - controlled | | | | | | | | 60-100 | Irreg, no p-wave | | |
| Atrial Fibrillation - rapid | | | | | | | | >100 | Irreg, no p-wave | | |
| Ventricular Tachycardia | | | | | | Cannon a-waves | Cannon a-waves | >120 | Reg QRS >110 msec; AV dissociation | | |
| Complete Heart Block | | | | | | Cannon a-waves | Cannon a-waves | <50 | AV dissociation | | |
| Non cardiac | | | | | | | | | | | |
| Respiratory Distress | | | | ↑↑ | ↑↑ | | | ← | | | |
| hyperthermia | | | | | | | | | | | ←↑ |
| hypothermia | | | | | | | | | | | ↓↑ |

| PRESSURES | Average (mm HG) | Range (mm HG) |
|---|---|---|
| Right atrium | | |
|     *a* wave | 6 | 2-7 |
|     *v* wave | 5 | 2-7 |
|     mean | 3 | 1-5 |
| Right ventricle | | |
|     peak systolic | 25 | 15-30 |
|     end-diastolic | 4 | 4-7 |
| Pulmonary artery | | |
|     peak systolic | 25 | 15-30 |
|     end-diastolic | 9 | 4-12 |
|     mean | 15 | 9-10 |
| Pulmonary capillary wedge | | |
|     mean | 9 | 4-12 |
| Left atrium | | |
|     *a* wave | 10 | 4-16 |
|     *v* wave | 12 | 6-21 |
|     mean | 8 | 2-12 |
| Left ventricle | | |
|     peak systolic | 130 | 90-140 |
|     end-diastolic | 8 | 5-12 |
| Central aorta | | |
|     peak systolic | 130 | 90-140 |
|     end-diastolic | 70 | 60-80 |
|     mean | 85 | 70-105 |
| VASCULAR RESISTANCES | MEAN (dyne-sec-cm$^{-5}$) | RANGE (dyne-sec-cm) |
| Systemic vascular resistance | 1100 | 700-1600 |
| Total pulmonary resistance | 200 | 100-3000 |
| Pulmonary vascular resistance | 70 | 20-1300 |

*FIG. 19*

METHOD FOR DIGITAL CARDIAC RHYTHM MANAGEMENT

This application is a continuation of U.S. application Ser. No. 11/027,646, filed Dec. 30, 2004, which is a continuation of U.S. application Ser. No. 11/015,336, filed Dec. 17, 2004, which is a nonprovisional application of U.S. Provisional No. 60/531,238 filed Dec. 19, 2003, each of which is hereby incorporated by reference in its entirety.

BACKGROUND

1. Technical Field

This disclosure relates generally to systems and methods for detecting, diagnosing and treating cardiovascular disease in a medical patient using cardiac rhythm management devices and methods that use novel digital electrode technology.

2. Description of the Related Art

The optimum management of patients with chronic diseases requires that therapy be adjusted in response to changes in the patient's condition. Ideally, these changes are measured by daily patient self-monitoring prior to the development of symptoms. Self-monitoring and self-administration of therapy forms a closed therapeutic loop, creating a dynamic management system for maintaining homeostasis. Such a system can, in the short term, benefit day-to-day symptoms and quality-of-life, and in the long term, prevent progressive deterioration and complications.

In some cases, timely administration of a single dose of a therapy can prevent serious acute changes in the patient's condition. One example of such a short-term disease management strategy is commonly used in patients with asthma. The patient acutely self-administers an inhaled bronchodilator when daily readings from a hand-held spirometer or flowmeter exceed a normal range. This has been effective for preventing or aborting acute asthmatic attacks that could lead to hospitalization or death In another chronic disease, diabetes mellitus, current self-management strategies impact both the short and long term sequelae of the illness. Diabetic patients self-monitor blood glucose levels from one to three times daily and correspondingly adjust their self-administered injectable insulin or oral hypoglycemic medications according to their physician's prescription (known as a "sliding scale"). More "brittle" patients, usually those with juvenile-onset diabetes, may require more frequent monitoring (e.g., 4 to 6 times daily), and the readings may be used to adjust an external insulin pump to more precisely control glucose homeostasis. These frequent "parameter-driven" changes in diabetes management prevent hospitalization due to symptoms caused by under-treatment (e.g., hyperglycemia with increased hunger, thirst, urination, blurred vision), and over-treatment (e.g., hypoglycemia with sweating, palpitations, and weakness). Moreover, these aggressive management strategies have been shown to prevent or delay the onset of long-term complications, including blindness, kidney failure, and cardiovascular disease.

There are approximately 60 million people in the U.S. with risk factors for developing chronic cardiovascular diseases, including high blood pressure, diabetes, coronary artery disease, valvular heart disease, congenital heart disease, cardiomyopathy, and other disorders. Another 10 million patients have already suffered quantifiable structural heart damage but are presently asymptomatic. Still yet, there are 5 million patients with symptoms relating to underlying heart damage defining a clinical condition known as congestive heart failure (CHF). Although survival rates have improved, the mortality associated with CHF remains worse than many common cancers. The number of CHF patients is expected to grow to 10 million within the coming decade as the population ages and more people with damaged hearts are surviving.

CHF is a condition in which a patient's heart works less efficiently than it should, and a condition in which the heart fails to supply the body sufficiently with the oxygen-rich blood it requires, either during exercise or at rest. To compensate for this condition and to maintain blood flow (cardiac output), the body retains sodium and water such that there is a build-up of fluid hydrostatic pressure in the pulmonary blood vessels that drain the lungs. As this hydrostatic pressure overwhelms oncotic pressure and lymph flow, fluid transudates from the pulmonary veins into the pulmonary interstitial spaces, and eventually into the alveolar air spaces. This complication of CHF is called pulmonary edema, which can cause shortness of breath, hypoxemia, acidosis, respiratory arrest, and death. Although CHF is a chronic condition, the disease often requires acute hospital care. Patients are commonly admitted for acute pulmonary congestion accompanied by serious or severe shortness of breath. Acute care for congestive heart failure accounts for the use of more hospital days than any other cardiac diagnosis, and consumes in excess of 20 billion dollars in the United States annually.

Cardiac rhythm management devices such as pacemakers, are an important tool in the treatment of cardiovascular diseases. Typically, an implantable pacemaker uses a minimum of two electrodes to stimulate tissue. At least one of these electrodes is in contact with the heart tissue to be stimulated, and is called a pacing electrode. The required second electrode need not be in contact with tissue being stimulated, in which case it is called an "indifferent" electrode. The indifferent electrode does not even have to be in the heart. Cardiac pacemakers in commercial use today all have the same basic configuration in which stimulating electrical pulses are produced by a pulse generator located outside the heart, typically in a subcutaneous pocket in the upper chest near one shoulder. The stimulating electrical pulses are applied to the electrodes via one or more electrical conductors within an insulated flexible cable, or "lead", which is connected at its proximal end to the pulse generator. The distal end of the lead is placed within the heart at a desired pacing location, for example in the apex of the right ventricle. Some pacemaker leads, called "unipolar" leads, have only a pacing electrode, typically at the distal end of the lead. In this case, the required indifferent electrode may be provided by the metallic housing of the generator, or conceivably could be located on another lead. Commonly, unipolar pacemaker leads have a single conductor connecting the generator to a single pacing electrode located at its distal end. Bipolar pacemaker leads have two conductors, one connected to a pacing electrode located at or near the distal end of the lead, the other connected to an "indifferent" electrode, usually configured as a ring electrode, located on the lead some distance proximal to its distal end.

SUMMARY OF CERTAIN INVENTIVE ASPECTS

Several embodiments of this disclosure relate to systems and methods for detecting, diagnosing and treating cardiovascular disease in a medical patient using cardiac rhythm management devices and methods that use novel digital electrode technology.

As discussed above, some cardiac rhythm management devices apply electrical stimuli to the heart. In addition to applying electrical stimuli to the heart, cardiac pacemakers also commonly measure, or "sense," the natural electrical activity within the heart in order to adjust, withhold, or apply stimulation in response to specific electrophysiological conditions. Sensing electrodes are commonly incorporated on pacing leads. In most cases, the same electrode used for pacing is also used for sensing. Although sharing of electrodes for pacing and sensing is common, it does have limitations. The sensed electrical signals are much weaker than the pacing pulses, and must be highly amplified before being used in various ways to control the operation of the pacemaker. An ideal sensing electrode should have a large surface area for this very reason, while an ideal pacing electrode should have a small surface area to minimize power requirements. Moreover, following each pacing pulse there is a time interval during which sensing cannot take place because the relatively high pacing pulse voltage persists for some time due to capacitance in the lead. Thus, potentially important electrophysiological data may be lost during this interval with presently available pacemaker technology. One example of such data is the evoked response to the pacing stimulus. It would be beneficial to provide a lead with separate sensing and pacing electrodes. However, in some cases, such a lead would conventionally require separate sensing and pacing conductors as well, which would disadvantageously require the lead diameter to be increased. Thus, conventional combination sensing/pacing electrodes represent a compromise between optimal pacing performance and optimal sensing performance, and conventional pacemaker leads represent a compromise between optimal electrode performance and lead size, complexity, and reliability, as discussed further below.

In some pacemakers, the lead further incorporates one or more physiological sensors. The lead must then also provide the electrical connections required to power the sensor(s) and to return the physiological sensor signal back to the pacemaker generator. One disadvantage with such multiple function pacemaker leads is the that increased number of electrical conductors required within the lead forces the lead to be larger in diameter and less flexible, or that the conductors become smaller. Smaller conductors in pacemaker leads may break more often over time, resulting in lower lead reliability. Smaller conductors have higher electrical resistance, resulting in an undesirable voltage drop between the generator and the pacing electrode(s). An increased number of conductors also increases the complexity of the connector that plugs into the pacemaker generator housing.

Conventional cardiac pacemakers in clinical use, although employing digital electronics in the pacemaker generator, use analog voltages for pacing, sensing and physiological measurements. As such, the sensing signals in particular are subject to noise due to muscular activity, radiofrequency (RF) interference, and potential cross-talk between physiological and electrical sensing signals. Pacemaker lead conductors carrying analog signals act as antennas for RF noise and for induced voltages due to RF energy used in magnetic resonance imaging (MRI) scanners. RF noise on the sense conductor may cause erroneous pacing, even with sophisticated digital filtering algorithms commonly used in pacemaker sensing systems. Voltages induced by RF and changing magnetic fields are a primary reason why MRI scanning is contraindicated for patients with implantable cardiac pacemakers.

In general, incorporation of a sensor within a unipolar pacing lead typically requires plural conductors that run the length of the lead. This arrangement provides the proper electrical connection between the implanted pacemaker and the sensor, and between the pacemaker and the tip electrode. For a bipolar lead, an additional conductor is typically required. One disadvantage of these arrangements is that the more electrical conductors that are required in a lead, the greater potential for lead unreliability. See U.S. Pat. Nos. 5,843,135, 4,791,935, 4,497,755, 4,485,813, 4,432,372, all herein incorporated by reference. Lead reliability is an important consideration, and several embodiments of the present invention minimize the number of conductors required to run the length of the pacing lead. Accordingly, several embodiments of the present invention maximize lead reliability. Several embodiments of the present invention also provide a lead which incorporates a pressure sensor or similar transducer positioned toward the distal end for sensing a heart parameter, the lead having a safe arrangement enabling the use of only one or two conductors for providing a connection to both the sensor and a pacing/sensing electrode positioned at or about the distal tip of the lead.

In one embodiment, a cardiac rhythm management (CRM) apparatus is provided. In one embodiment, the CRM comprises: a proximal housing, wherein the proximal housing comprises a first energy storage device; a distal module (sometimes referred to as a distal housing) implantable within a patient's heart, wherein the distal module comprises a second energy storage device, at least one electrode and a control module, wherein the control module controls the delivery of at least one electrical stimulus from said second energy storage device to a location in communication with said patient's heart; and a lead, wherein the lead connects the proximal housing to the distal module and is configured to communicate one or more digital signals between the proximal housing and the distal module.

In one embodiment, the control module controls the transfer of energy from the first energy storage device to the second energy storage device. In another embodiment, the proximal housing controls the transfer of energy from the first energy storage device to the second energy storage device In a further embodiment, an implantable therapeutic apparatus is provided. In one embodiment, the implantable therapeutic apparatus comprises: a proximal housing, wherein the proximal housing comprises an energy storage device; a distal module, wherein the distal module comprises an electrode and a control module, wherein the control module controls the delivery of at least one electrical stimulus to the patient via said electrode; and a lead, wherein the lead connects the proximal housing to the distal module and is configured to communicate one or more digital signals between the proximal housing and the distal module. The electrical stimulus, in one embodiment, comprises one or more electrical pulses.

In one embodiment, the therapeutic apparatus comprises a cardiac rhythm management (CRM) device. In one embodiment, the CRM device comprises a cardiac pacemaker and/or a cardiac defibrillator.

In one embodiment, the implantable therapeutic apparatus comprises one or more of the following: a neurological stimulator, a muscle stimulator device, a drug infusion pump, a ventricular assist device, a brain stimulator.

In one embodiment, the implantable therapeutic apparatus comprises a proximal housing that is implantable near the patient's shoulder.

In a further embodiment, the implantable therapeutic apparatus comprises a lead, wherein the lead comprises one or more conductors. In one embodiment, two conductors are used. In another embodiment, three conductors are used.

In one embodiment, the implantable therapeutic apparatus comprises a first energy storage device that comprises a battery or capacitor. In another embodiment, the distal module comprises a battery or capacitor.

In one embodiment, the implantable therapeutic apparatus comprises a pacing electrode. In one embodiment, the implantable therapeutic apparatus comprises at least one sensing electrode and at least one pacing electrode, wherein said sensing electrode has a larger surface area than said pacing electrode.

In a further embodiment, the implantable therapeutic apparatus comprises a distal module that comprises at least one physiological sensor. In one embodiment, the physiological sensor includes a pressure sensor and/or a thermometer. In another embodiment, the electrical stimulus comprises one or more electrical pulses. In another embodiment, the implantable therapeutic apparatus also includes a sensing amplifier. In yet another embodiment, the one or more digital signals comprises a sense-detect signal.

In yet another embodiment, a cardiac rhythm management apparatus for delivering one or more electrical pulses to a patient's heart is provided. In one embodiment, this apparatus comprises: a proximal housing, wherein said proximal housing is configured to be implanted within a medical patient, and wherein said proximal housing is configured to store electrical energy; a distal module configured to be implanted within a heart, wherein the distal module comprises a first energy storage device and a control module; an electrode, operable to deliver one or more electrical pulses from the first energy storage device to the heart; and a lead, wherein said lead is configured to communicate one or more digital signals between said proximal housing and said distal module, and wherein said control module controls communication of said digital signals on the lead.

In one embodiment, the distal module further comprises a second energy storage device. In another embodiment, said one or more digital signals are used to charge the second energy storage device. In another embodiment, said second energy storage device provides power to said control module. In another embodiment, said second energy storage device stores provides energy to said first energy storage device by using a charge pump. In another embodiment, said distal module further comprises a sensing amplifier. In another embodiment, said distal module further comprises a sensor configured to provide a sensor signal, and said distal module controls delivery of a therapy based at least in part on said sensor signal.

In one embodiment, said distal module further comprises a processor, said processor is configured to generate a processed signal based at least in part on the sensor signal, and the distal module is configured to communicate the processed signal to said proximal housing said lead. In another embodiment, said distal module further comprises at least one sensing electrode. In another embodiment, said lead further comprises a conductor, and said at least one sensing electrode is indirectly connected to said conductor. In yet another embodiment, the lead further comprises a conductor, and the electrode is indirectly connected to the conductor.

In another embodiment, an apparatus for treating cardiovascular disease in a medical patient is provided. In one embodiment, this apparatus comprises: a housing, a distal module comprising a sensor, operable to generate a sensor signal indicative of a fluid pressure within a left atrium of a heart; a lead, wherein the lead is configured to communicate one or more digital signals between the housing and the distal module; a signal processor, operable to generate a processor output indicative of a treatment, wherein said processor output is based at least in part on the sensor signal; and a signaling device, operable to generate a treatment signal indicative of a therapeutic treatment, wherein said treatment signal is based at least in part on said processor output.

In one embodiment, the distal module further comprises at least one electrode. In another embodiment, the at least one electrode is operable to sense a physiological parameter. In another embodiment, the physiological parameter comprises electrical depolarization. In yet another embodiment, the at least one electrode is operable to deliver an electrical stimulus to a location in the heart.

In one embodiment, a method of managing a cardiac rhythm in a medical patient is provided. In one embodiment, this method comprises: implanting a proximal housing in a location external to the patient's heart wherein said proximal housing stores energy; implanting a distal module in the patient's heart; implanting a lead in the patient to couple said proximal housing and said distal module; transferring at least a portion of said stored energy from said proximal housing to said distal module through one or more digital signals; storing said transferred energy in the distal module; and using at least a portion of the transferred energy in the distal module to deliver one or more electrical pulses to the heart, thereby managing a cardiac rhythm in the patient.

In one embodiment, the method comprises storing said at least a portion of said energy in said distal module. In another embodiment, the method comprises sensing the electrical activity of the medical patient's heart with a sensing electrode. In one embodiment, the method comprises delivering said one or more electrical pulses to the heart using a pacing electrode. In a further embodiment, the method comprises recharging the energy stored in the proximal housing. In one embodiment, the method further comprises the step of measuring a pressure signal indicative of a pressure within the left atrium.

In one embodiment of the present invention, a method of managing a cardiac rhythm in a medical patient is provided. In one embodiment, this method comprises: implanting a proximal housing, a distal module, and a lead coupling said proximal housing and said distal module in a patient; transferring energy from said proximal housing to said distal module through one or more digital signals; and delivering one or more electrical pulses to the heart from said distal module, wherein said one or more electrical pulses comprise at least a portion of the energy received from the proximal housing, thereby managing a cardiac rhythm in the patient.

In yet another embodiment, a physiologic monitoring apparatus is provided. In one embodiment, the physiologic monitoring apparatus comprises: an implantable first component operable to connect to an implantable therapeutic device (ITD), wherein said implantable first component comprises a transducer and a communicator, wherein said transducer is operable to convert a physiologic signal to an electrical signal, and wherein said communicator is operable to communicate with an external second apparatus component receiver; and a removable telemetry antenna operable to be removed and replaced with said ITD. In one embodiment, the ITD comprises a cardiac rhythm management device.

In another embodiment, a physiological monitoring device is provided. In one embodiment, the physiological monitoring device comprises: a proximal housing adapted to be implanted within a patient at a location external to an organ to be monitored; a distal module adapted to be implanted within the patient at a location at least partially internal to the organ to be monitored; a lead, said lead having at least a first end, a second end, and a connector attached to said first end, wherein said lead is connected to said distal module at said second end, and wherein said lead is configured to conduct power and data signals between the distal module and the proximal housing, and wherein the connector is adapted to interchangeably connect to an antenna coil or a cardiac rhythm management device provided within said proximal housing.

In one embodiment, the cardiac rhythm management device is configured to provide said power and data signals. In another embodiment, the antenna coil is configured to provide said power and data signals. In another embodiment, the distal module is configured to automatically operate under a first mode of operation when said connector is connected to said antenna coil, and said distal module is configured to automatically operate under a second mode of operation when said connector is connected to said cardiac rhythm management device.

In another embodiment, a cardiac rhythm management device is provided. In one embodiment, the cardiac rhythm management device comprises: a proximal housing, wherein said proximal housing is configured to be implanted within a patient, wherein said proximal housing is configured to store electrical energy, and wherein said proximal housing is adapted to be implanted at a location external to a heart; a distal module adapted to be implanted within the heart, and to provide electrical energy received from said proximal housing to said heart, wherein said distal module is configured to provide defibrillation protection to said heart; and a lead, wherein said lead electrically couples said proximal housing and said distal module, and wherein said lead provides said electrical energy from said proximal housing to said distal module.

In one embodiment, a flexible lead for implantation within a human body, is provided. In one embodiment, the flexible lead comprises: a lead length, wherein said lead length extends from a first end to a second end, wherein said first end is coupled to a proximal housing implanted at a first location within a human body, and said second end is coupled to a distal housing implanted at a second location within a human body; and at least two conductors, wherein said at least two conductors extend from the first end to the second end, and wherein said at least two conductors are in electrical communication with at least three electrodes, and wherein said at least three electrodes are greater in quantity than said at least two conductors.

In one embodiment, the lead further comprises a shielding, wherein said shielding extends from said first end to said second end, covering at least one of said at least two conductors over said lead length. In another embodiment, the first location is proximate a shoulder, and said second location is in inside of a heart. In another embodiment, the at least three electrodes comprise an indifferent electrode, a pacing electrode, and a sensing electrode.

In one embodiment, an implantable sensor apparatus is provided, wherein said sensor apparatus is capable of being powered externally by RF at one frequency or powered by an ITD at a different frequency. In one embodiment, the device is externally powered by an RF sine wave or powered by monophasic pulses from an ITD.

In an alternative embodiment, an implantable device that provides one or more electrical stimuli is provided. In one embodiment, a remote distal electrode for delivering stimuli co-located with an output switch, a capacitor and defibrillator protection is provided.

In one embodiment, an implantable device that provides one or more electrical stimuli, comprising a remote distal electrode co-located with sensing amplifier and detector, is provided.

In one embodiment, a system wherein the communication between a CRM and a digital electrode comprises digital communication is provided. In one embodiment, the digital communication comprises a digital sense detect signal sent from the digital electrode to the proximal housing (module). In another embodiment, the digital communication comprises a digital pace trigger command sent from the proximal housing (module) to the digital electrode. In a further embodiment, the digital communication comprises a digitized sense signal sent from the digital electrode to the proximal housing (module).

In one embodiment, a system having separate pace and sense electrodes without separate conductors in the lead for sensing and pacing is provided.

In a further embodiment, a system comprising a digital electrode that automatically detects whether it is powered externally or from an ITD, and automatically switches to the external or ITD configuration, is provided. In one embodiment, the power pulses from the ITD are used by the digital electrode to synchronize the digital electrode (and/or sensor, if present) clock and/or communication.

In one embodiment, an apparatus having an electrode with its conducting surface area reduced by coating a portion of the surface with an insulating material is provided. In one embodiment, reflective impedance is used to communicate information to an external device.

BRIEF DESCRIPTION OF THE DRAWINGS

The structure and operation of the invention will be better understood with the following detailed description of embodiments of the invention, along with the accompanying illustrations, in which:

FIGS. 6A-6C provide a list of examples by which signals may be interpreted to facilitate diagnosis, prevention and treatment of cardiovascular disease.

FIG. 7 shows a table of cardiac and non-cardiac diagnostic states derivable from measurements at the intra-atrial septum.

FIG. 19 provides a table of normal hemodynamic values.

DETAILED DESCRIPTION

Figure 1:
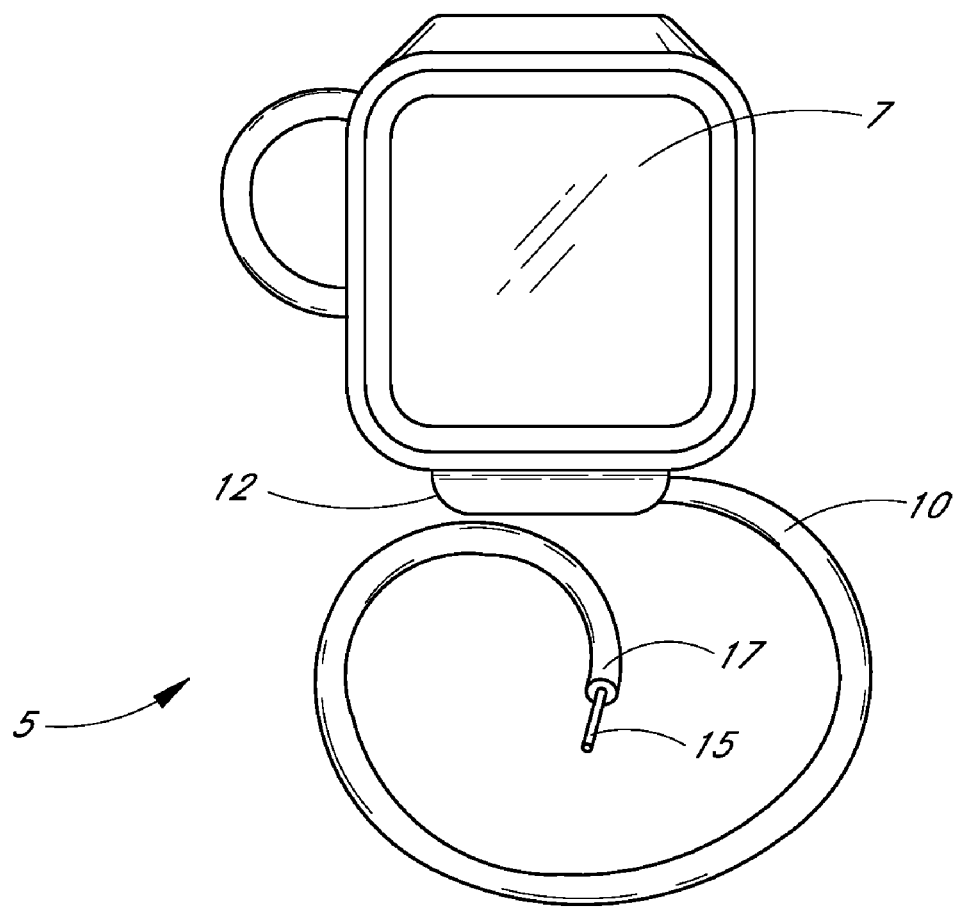
FIG. 1 depicts apparatus suitable for practicing at least one embodiment of the invention.

In one embodiment of the present invention an apparatus for treating cardiovascular disease in a medical patient is provided. The apparatus includes a sensor, an implantable housing, at least one implantable lead, a signal processor, and a signaling device. In one embodiment, the apparatus is a physiologically optimized dosimeter (POD), such as the HeartPOD™ device. Cardiovascular disease, as used herein, shall be given its ordinary meaning, and shall also include conditions that create or are the result of heart disease such as high blood pressure, coronary artery disease, valvular heart disease, congenital heart disease, arrthymia, myocarditis, pericarditis, cardiomyopathy including dilated, hypertrophic, obliterative, and restrictive/infiltrative types, cardiac transplant rejection, and CHF. Additionally, cardiovascular disease shall also include disease states that affect the circulatory system including but not limited to peripheral arterial atherosclerosis, Berger's disease, cerebral vascular atherosclerosis, aortic or other great vessel aneurysm, aortic or other great vessel dissection, vasculitis, venous thrombophlebitis, and their sequelae.

In one embodiment of the present invention, a method of treating cardiovascular disease in a medical patient is provided. The method includes the steps of generating a sensor signal indicative of a fluid pressure within a left atrium of a heart, delivering an electrical stimulus to the heart, generating a processor output indicative of a treatment to a signaling device, and providing at least two treatment signals to the medical patient. The electrical stimulus is based at least in part on the sensor signal. The processor output is based at least in part on the sensor signal. Each treatment signal is distinguishable from one another by the patient, and is indicative of a therapeutic treatment. At least one signal is based at least in part on the processor output. In one embodiment, the step of delivering an electrical stimulus includes using a pacemaker or a defibrillator.

In several embodiments of the current invention, the apparatus and/or method for treating cardiovascular disease includes a cardiac rhythm management (CRM) apparatus. In one embodiment, the cardiac rhythm management apparatus includes a pacemaker. The term pacemaker includes anti-bradycardia and antitachycardia types. The term pacemaker also includes single chamber, dual chamber, and cardiac resynchronization therapy (CRT) types, the latter also called a biventricular pacemaker. In another embodiment, the cardiac rhythm management apparatus includes a defibrillator. The term defibrillator, as used herein, shall be given its ordinary meaning and shall include atrial and ventricular defibrillators with or without combination with any of the pacemaker types listed above, or other devices. In another embodiment, the cardiac rhythm management apparatus includes related devices that do not electrically depolarize all or some portion of the heart muscle to manage a cardiac rhythm or the synchrony of depolarization, but are used to perform some other function. For example, delivering electrical stimuli to cardiac muscle during the refractory period after depolarization may increase the strength of cardiac contraction, a phenomenon known as an 'ionotropic' effect. This may be helpful in generating more cardiac output in CHF patients with low cardiac output. In another example, many CHF patients have a condition known as sleep apnea where they momentarily stop breathing during sleep. This condition is potentially dangerous because lack of oxygen can induce fatal cardiac arrhythmias or worsening heart failure due to ischemia. In one embodiment of the current invention, the CRM is a rhythm management system that paces the diaphragm muscle or the phrenic nerves to benefit such patients.

In one embodiment of the invention, the apparatus and/or method for treating cardiovascular disease includes one or more sensors. In one embodiment, the sensor is designed to generate a sensor signal that is indicative of a fluid pressure within the left atrium of the patient's heart. As described herein, fluid pressure within the left atrium of a patient's heart is an excellent indicator for quantifying the severity of congestive heart failure, and for assessing the efficacy of drug therapy for treating congestive heart failure. A measurement of the fluid pressure within the left atrium of a patient's heart can be used for other clinical purposes as well, as described in greater detail below.

In one embodiment, the pressure sensor and its associated electronics are integrated within a sensor module attached to the distal end of a lead implanted in the heart. The proximal end of the lead is connected to a housing located outside the heart, typically under the skin in the area of the patient's shoulder. One advantage of this embodiment is that placing some or all of the sensor electronics in the distal module allows the number of conductors required in the lead between the sensor and the proximal housing to be minimized, as described in more detail below. In one embodiment, the distal sensor module comprises a miniature hermetically sealed housing. In one embodiment, the housing is cylindrical, with a diameter similar to the diameter of the lead. In one embodiment, the pressure sensor lead may also be used for pacing, with all or preferentially a portion of the outside of the sensor housing of the present invention used as one of the electrodes of the pacemaker. To even greater advantage, some of the pacing electronics (for example, the output pulse and input (sense) amplifier, filter, threshold detector & refractory circuit) may also be integrated within the sensor housing implanted within the heart. This embodiment has several potential advantages. One such advantage is that the lead conductors are isolated from the pacing electrode, providing immunity from induced currents when, for example, the patient is placed in the rapidly changing strong magnetic fields of a magnetic resonance imaging machine. Another such advantage is that placing the pacing sense electronics in the distal module eliminates noise originating in the lead conductors of a conventional pacemaker, since the low voltage sense signal need not be conducted through the lead. Yet another advantage is that separate sensing and pacing electrodes can be provided at or near the distal module without requiring separate sense and pacing conductors within the lead.

In one embodiment of the invention, the apparatus and/or method for treating cardiovascular disease includes one or more housing units comprising electronic modules. In one embodiment, the implantable apparatus includes a proximal housing comprising the generator of a cardiac rhythm management (CRM) apparatus, such as, for example, a pacemaker, or a defibrillator. A pacemaker generator conventionally includes various subassemblies for control, operation, processing, and communication. However, in some embodiments of the present invention, any one or more of these control, operation, processing, and communication functions may be performed by an assembly, or module, that is not included with the proximal generator housing.

In one embodiment, when implanted in the patient, the implantable housing contains a coil antenna and electronics to provide reflected impedance communications with an external device. However, as the patient's medical condition changes and indications for CRM develop, the implantable housing may be subsequently accessed, and the coil antenna may be removed and replaced with a CRM system. The implantable housing and electronics may include an interface that permits such interchangeability of components within the implantable housing without requiring explantation of the remaining components of the implanted congestive heart failure treatment apparatus. This feature of an embodiment of the invention is herein included within the term "upgradeability," or "upgradeable". These and additional embodiments of the implantable housing, as well as the apparatus, are provided in greater detail below.

In one embodiment, the lead couples the sensor to the implantable housing, and provides an electrical conduit for the transmission and/or communication of the sensor signal from the sensor to the housing. In other embodiments, however, as described in greater detail below, the lead provides an electrical stimulus, such as, for example, an electrical pulse, to a location in the heart, as determined by the CRM apparatus. In some embodiments, the electrical stimulus and the sensor signal are transmitted through the same lead. In a preferred embodiment, the electrical stimulus and the sensor signal are transmitted through the same conductors. This embodiment is particularly advantageous because the use of one conductor pair allows for a lead that is thinner, more flexible and/or sturdier. In another embodiment, separate conductors are provided within the lead for sensor signal communication and the CRM therapy. In yet another embodiment, energy or power is transmitted from the implantable housing through the lead to a distal module that may contain portions of a CRM apparatus, sensors, and portions of the signal processing necessary to control the cardiovascular disease treatment. These and other embodiments are described in greater detail below.

In one embodiment of the invention, the apparatus and/or method for treating cardiovascular disease includes one or more signal processors. In one embodiment, the signal processor determines a processor output that is indicative of an appropriate therapeutic treatment in response to the pressure-indicative signal provided by the sensor. The processor output is provided to a signaling device, which provides an appropriate treatment signal to the medical patient. The term "processor output" as used herein shall be given its ordinary meaning and shall also mean output from a signal processor and/or input to a signaling device, and shall include, but not be limited to, signals, including analog, digital, and/or optical signals, data, code, and/or text. The treatment signal may be provided by, for example, vibrating a signaling device located within the implantable housing. Alternatively, the treatment signal may be generated within the implantable housing and transmitted to a signaling device located external to the patient, such as a personal digital assistant (PDA). In another embodiment, the sensor signal is transmitted to an external device, such as, for example, a PDA, which includes a processor and signaling device to generate a processor output and provide a treatment signal to the patient. These and other embodiments are described in greater detail below.

In one embodiment of the invention, the apparatus and/or method for treating cardiovascular disease includes one or more signaling devices. In one embodiment, the signaling device includes a buzzer, an alarm, a display, a computer, a telephone, or a PDA, such as a PALM PILOT™ (Palm Computing, Inc.), a HANDSPRING VISOR® (Handspring, Inc.), or a combination cellular telephone/PDA. The signaling device may be operable to generate at least two treatment signals distinguishable from one another by the patient. In one embodiment, each signal is indicative of a specific therapeutic treatment. The treatment signal may be an electrical pulse, a vibration, a noise, audio, or visual data, including, but not limited to, instructions on a display screen or light emitting diodes. In one embodiment, the at least two treatment signals may include two numerical values or designations, a numerical value and an electrical pulse or vibration, multiple vibrations of varying amplitudes, durations, or frequencies, or any combination of two or more of any of the treatment signals described herein. In one embodiment, the signaling device is a PDA that displays an instruction, such as "take medication," "rest," or "call Doctor". These and other embodiments are described in greater detail below.

I. THE SYSTEM

A. Stand-Alone System

FIG. 1 shows an apparatus for treating cardiovascular disease, such as congestive heart failure, which includes an implantable module 5 in accordance with one embodiment of the invention. The implantable module 5 includes a housing 7 and a flexible, electrically conductive lead 10. The lead 10 is connectable to the housing 7 through a connector 12 that may be located on the exterior of the housing. In one embodiment, the housing 7 is outwardly similar to the housing of an implantable electronic defibrillator and/or pacemaker system. Defibrillator and pacemaker systems are implanted routinely in medical patients for the detection and control of tachy- and bradyarrhythmias. The flexible lead 10 is also generally similar to leads used in defibrillator and pacemaker systems, except that a compact sensor package 15 is disposed at or near the distal end 17 of the lead 10, the opposite end from the connector 12 on the housing 7. The sensor package 15 contains sensors to measure one or more physical parameters. An electrical signal or another form of signal indicative of these physical parameters is then communicated or transmitted along the lead 10 through the connector 12 and to the housing 7. The housing 7 may include a signal processor (not shown) to process the signal received from the sensor package 15 via the lead 10. In addition, the housing 7 may include telemetry or signaling devices (not shown), to either communicate with an external device, or signal the patient, or both. The elements inside the housing 7 may be configured in various ways, as described below, to communicate to the patient a signal, such as a treatment signal, indicative of an appropriate therapy or treatment based at least in part on one or more of the measured physical parameters.

One skilled in the art will appreciate that the lead can be of any length appropriate to connect the sensor package located at a first location with the housing located at a second location. In another embodiment, the lead length is zero, such that the sensor package are configured to occupy substantially the same location. Thus, in one embodiment, a leadless implantable system using telemetry between the heart and an external device is provided. In one embodiment, reflected impedance, rather than transmitted energy, is used to communicate with the implanted device, as described by U.S. Pat. No. 6,409,674 to Brockway et al., herein incorporated by reference.

Figure 2:
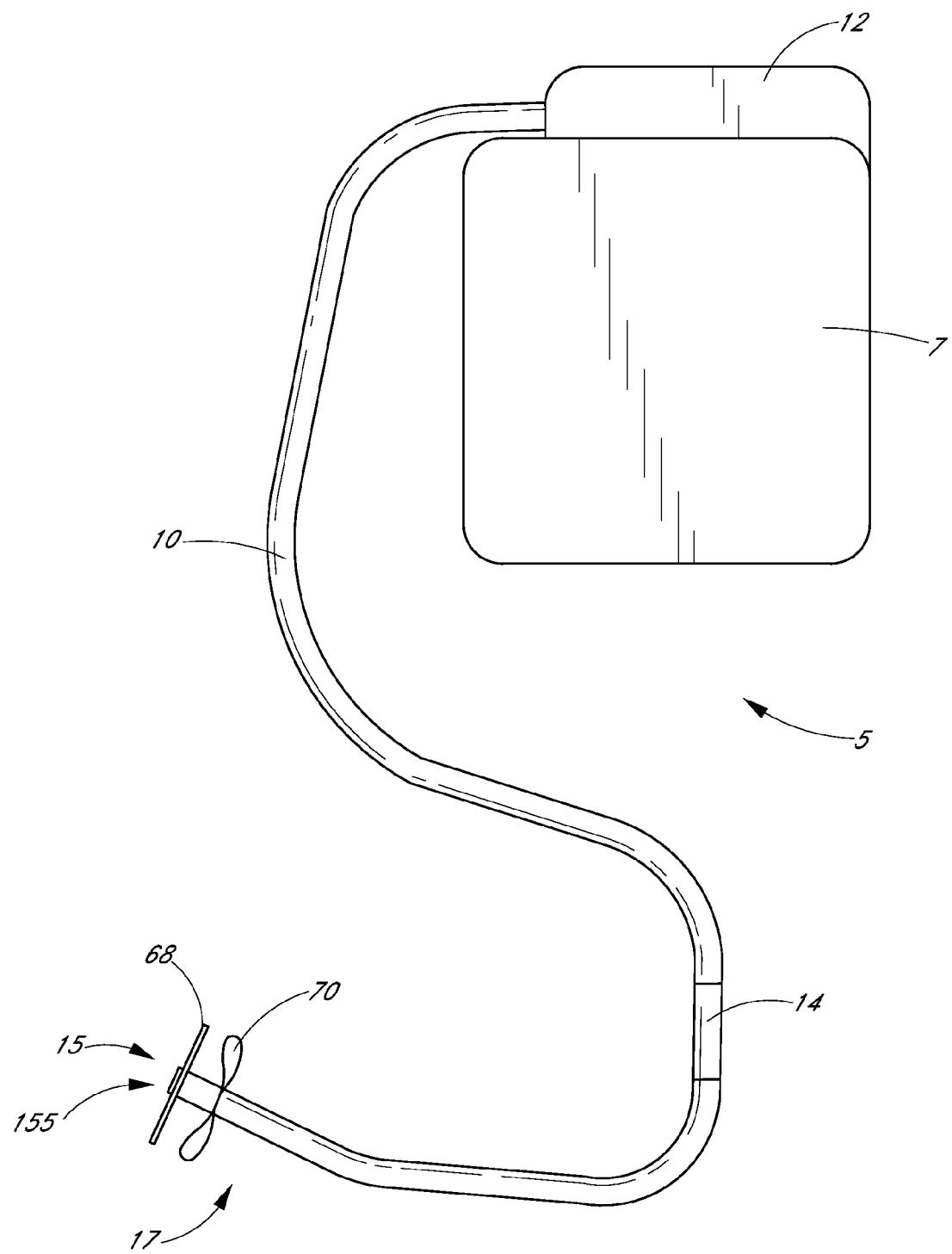
FIG. 2 depicts an implantable apparatus suitable for practicing another embodiment of the invention.

FIG. 2 shows another embodiment in which the sensor package or module 15 has distal 68 and proximal 70 anchors configured to anchor the sensor package 15 within the atrial septum of a patient's heart. FIG. 2 shows one embodiment of the implanted internal module 5, in which the implanted internal module 5 includes a physiologic sensor package or module 15. The physiologic sensor package 15 includes one or more sensors 155 and their accompanying electronics (not shown). The implanted module 5 also includes a flexible lead 10. The flexible lead 10 has a distal end 17 that comprises the sensor module 15, the metallic housing of which also functions as an electrode for sensing the intracardiac electrogram (IEGM), and an indifferent electrode 14. A header or connector 12 connects the flexible lead 10 and housing 7 of the implanted module 5. The housing 7 contains electronics (not shown) and other components (not shown) for communicating with an external module (not shown). One embodiment showing the contents of the housing 7 is illustrated in FIG. 3.

Figure 3:
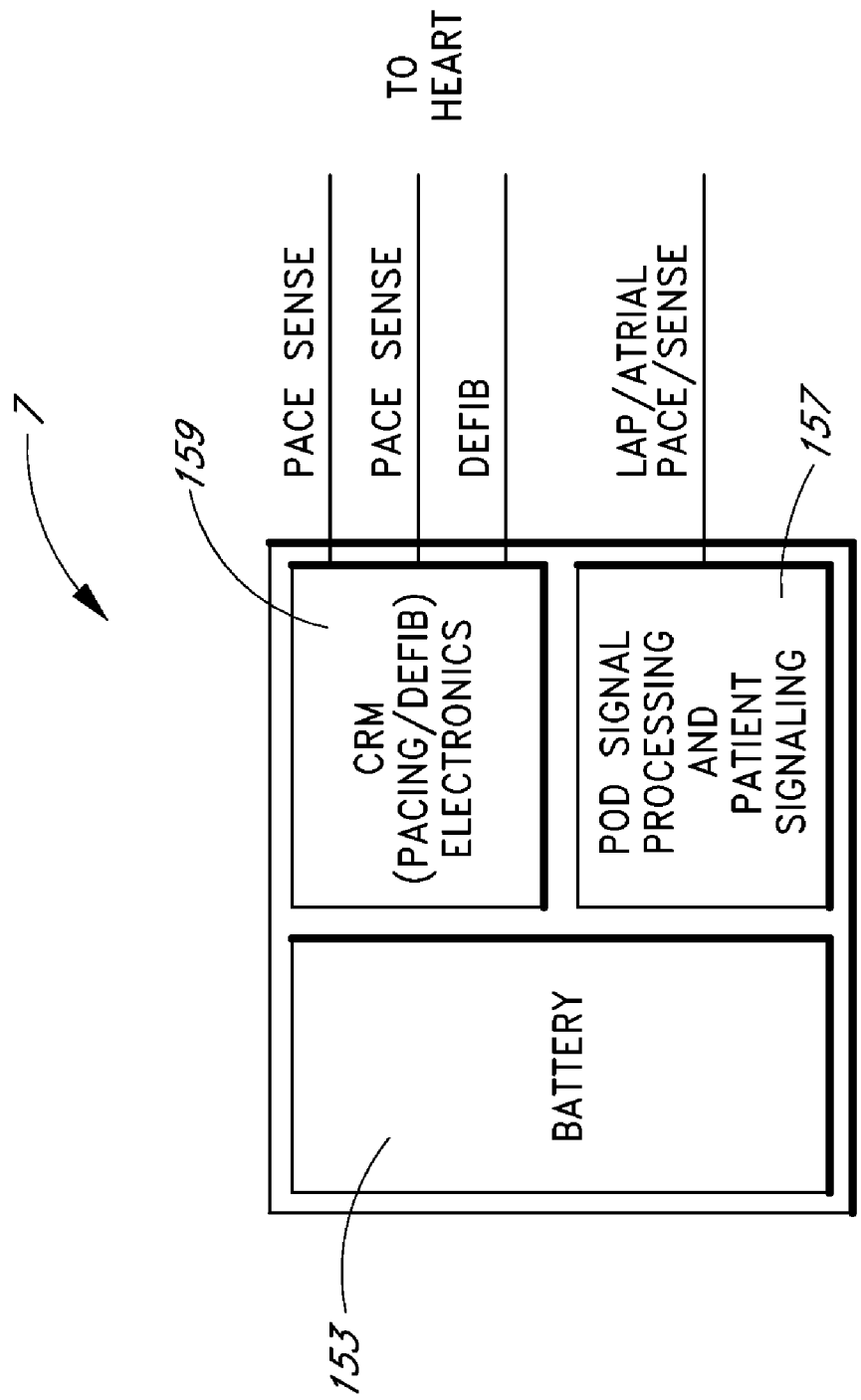
FIG. 3 is a schematic of one embodiment of the electronics located within the implantable housing of the implantable apparatus illustrated in FIG. 2.

As shown in FIG. 3, in one embodiment housing 7 includes a power supply 153, a CRM system 159, and a signal processing and patient signaling modules 157. The CRM system 159 is configured to provide an electrical stimulus, such as a pacing signal, to the patient's heart, and receive a sensor signal from implanted sensors (not shown). In one embodiment, the CRM system 159 is configured to include a defibrillator. The signal processing module 157 is coupled to at least one sensor that provides a signal indicative of the fluid pressure within the left atrium of the heart. The signal processing module 157 may also be configured to control distally implanted CRM components, or a sensor package or module, as described in greater detail herein.

In one embodiment of the invention, the apparatus for treating cardiovascular disease comprises at least one housing that has a flat and oval shape. In another embodiment, the housing shape is cylindrical, rectangular, elliptical, or spherical. One of skill in the art will understand that a variety of other shapes suitable for implantation can also be used. In one embodiment, the housing is about 20 mm by about 30 mm, about 10 mm by about 20 mm, or about 5 mm by about 10 mm. In one embodiment, the housing is about 5 mm thick. In one embodiment, the housing is implanted in the medical patient near the shoulder. In another embodiment, the housing has dimensions suitable for containing at least some components for controlling, powering and/or communicating with a sensor, and suitable for implantation inside of the body, as is well known to those of skill in the art. In another embodiment, the housing includes: an antenna, or a coil; a power source, including but not limited to a battery or a capacitor; a signal processor; a telemetry apparatus; a data memory; or a signaling device. In one embodiment, the apparatus is powered by an external power source through inductive, acoustical, or radio frequency coupling. In one embodiment, power is provided using electromagnetic emissions emitted from an electrical coil located outside the body. In one embodiment, power and data telemetry are provided by the same energy signal. In another embodiment, an electrical coil is implanted inside the body at a location under the skin near the patient's collarbone. In another embodiment, an electrical coil is implanted inside the patient's body at other locations. For example, in one embodiment, the coil is implanted under the skin in the lower abdomen, near the groin. One of skill in the art will understand that the device can be implanted in a variety of other suitable locations.

As described above and in other embodiments herein, a system for treating cardiovascular disease in a medical patient may include at least one physiological sensor used to generate a signal indicative of a physiological parameter on or in the patient's body. The system includes signal processing apparatus operable to generate a signal, such as a processor output, indicative of an appropriate therapeutic treatment, which in one embodiment is based at least in part upon the signal generated by the physiological sensor. In one embodiment, the system also includes a patient signaling device, which is used to communicate the signal indicative of the appropriate therapeutic treatment, such as a treatment signal, to the patient.

In one embodiment, the physiological sensor is a pressure transducer that is positioned to measure pressures within the patient's left atrium. Signals from the pressure sensor are monitored continuously or at appropriate intervals. Information is then communicated to the patient corresponding to appropriate physician-prescribed drug therapies. In one embodiment, the information is the treatment signal. In many cases, the patient may administer the drug therapies to him or herself without further diagnostic intervention from a physician.

Figure 4:
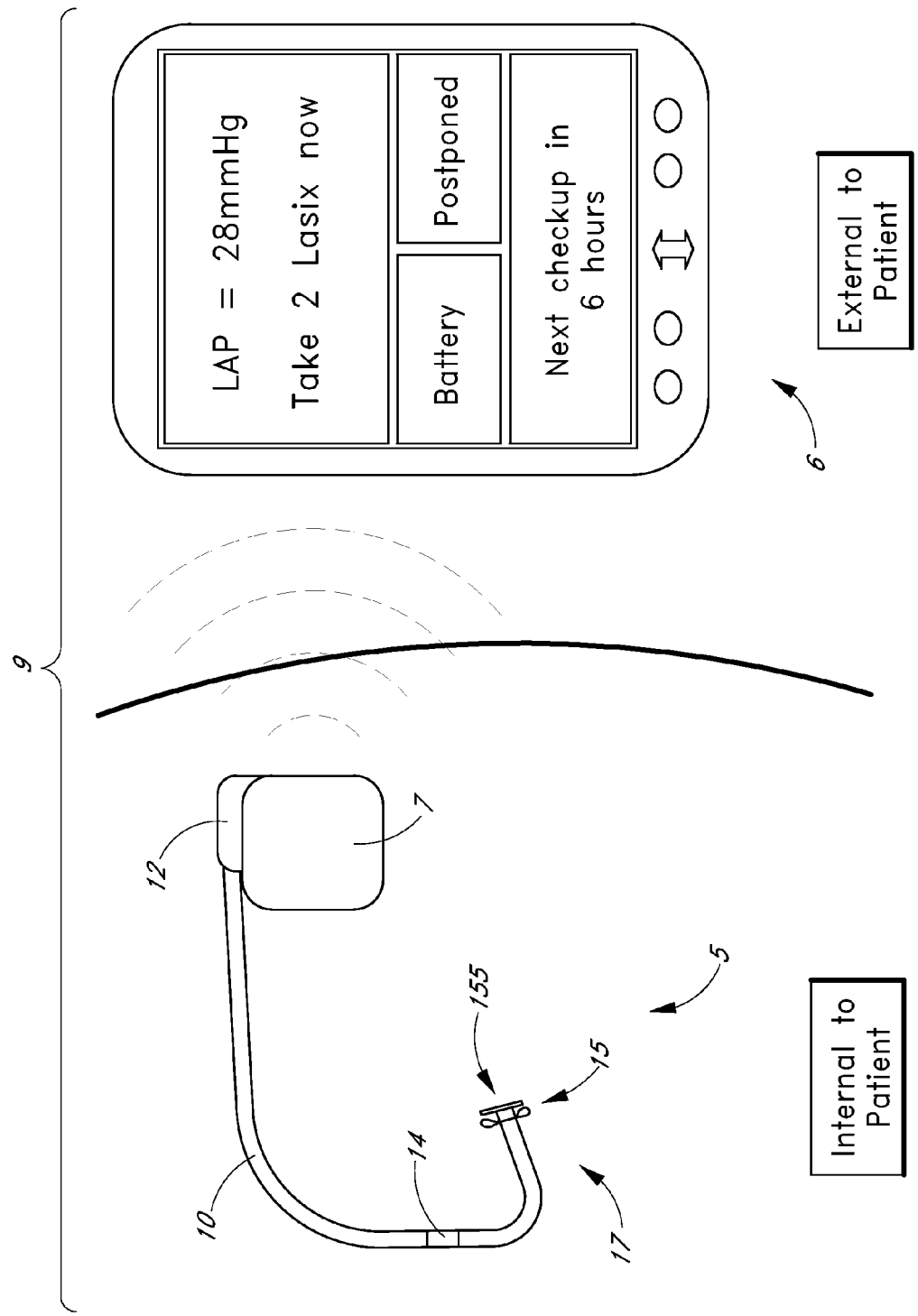
FIG. 4 is a system for treating cardiovascular disease.

FIG. 4 shows one embodiment of a system for treating cardiovascular disease 9. The system 9 includes a first component comprising an implantable module 5, such as that described with reference to FIG. 2, and a second component comprising an external patient advisory module 6, such as that described below with reference to FIG. 5. During system 9 operation, radio frequency signals are carried by a lead 10 between a pressure sensor package 15 located near the distal end 17 of the lead 10, and a housing 7 of an implantable module 5. The lead 10 includes a sensing/pacing electrode which is part of the sensor module 15 and an indifferent electrode 14. The circuitry inside the housing 7 includes an antenna coil (not shown). In this embodiment, signals are communicated between the implantable module 5 and an external device, such as a patient advisory module 6, via the antenna coil of the housing 7 and a second external coil (not shown) coupled to the external device 6.

In one embodiment, the housing 7 contains a battery (not shown) that powers the implantable device 5. In another embodiment, the implanted device 5 receives power and programming instructions from the external device 6 via radio frequency transmission between the external and internal coils. The external device 6 receives signals indicative of one or more physiological parameters from the implanted device 5 via the coils as well. One advantage of such externally powered implantable device 5 is that the patient will not require subsequent surgery to replace a battery. In one embodiment of the present invention, power is required only when the patient or the patient's caregiver initiates a reading. In other situations, where it is desired to obtain physiological information continuously, or where it is desired that the implanted device 5 also perform functions with higher or more continuous power requirements, the housing 7 may also contain one or more batteries. As described below, the housing 7 may also contain circuitry to perform additional functions that may be desirable.

Figure 5:
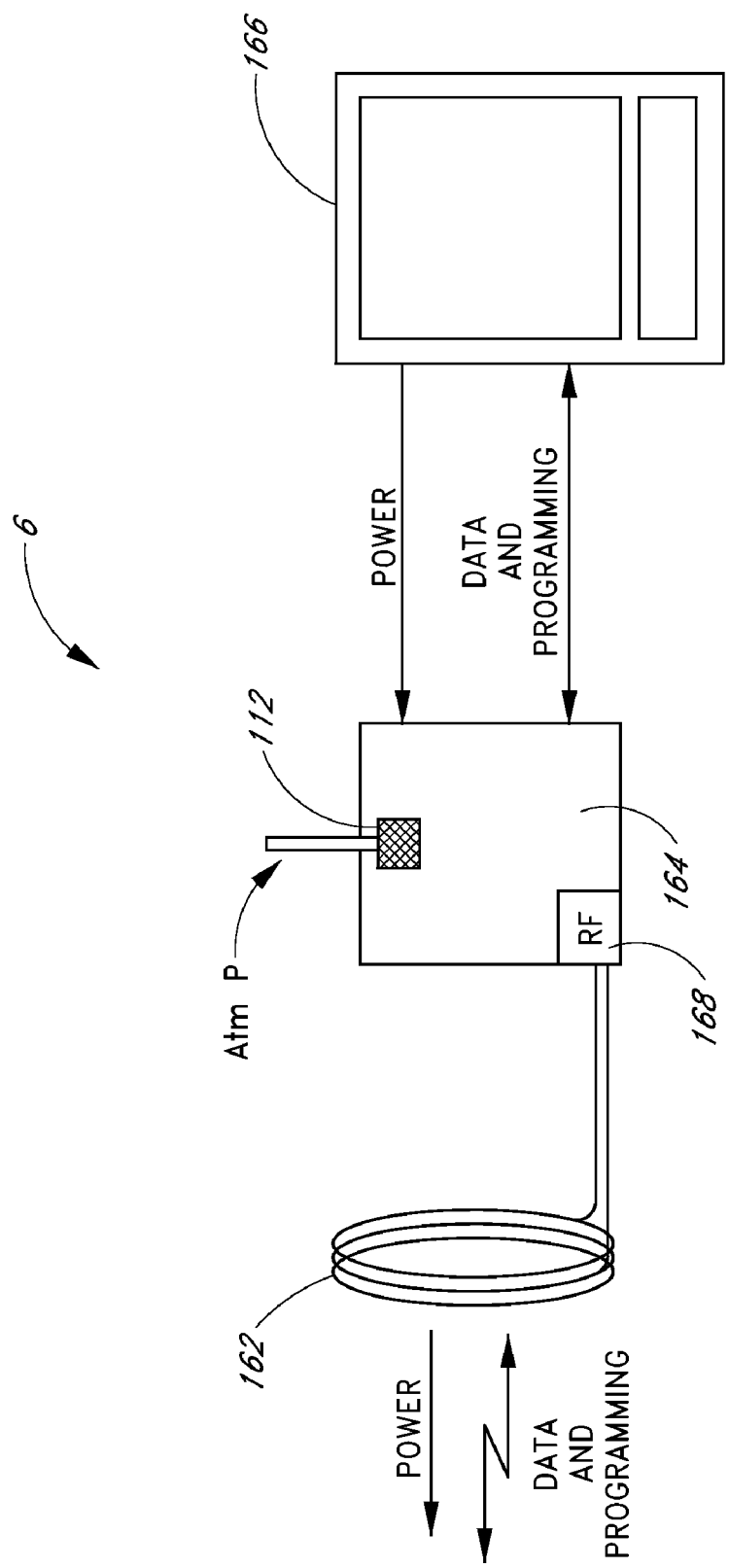
FIG. 5 is a block diagram of an external patient advisor/telemetry module for use in one embodiment of the present invention.

FIG. 5 shows one embodiment of the second component of the system, a patient advisory module 6. In one embodiment, the patient advisory module 6 includes a palm-type computer with added hardware and software. Referring to FIG. 5, a patient advisory module 6 includes a radio frequency telemetry module 164 with an associated coil antenna 162, which is coupled to a processing unit 166. In one embodiment, the processing unit 166 includes a palm-type computer, or personal digital assistant (PDA), as is well known to those of skill in the art. In one embodiment, the patient advisory module 6 powers the implanted apparatus (not shown) with the telemetry hardware module 164 and coil antenna 162. In another embodiment, the patient advisory module 6 receives physiological signals from the implanted first component of the system by wireless telemetry through the patient's skin.

The patient advisory module 6 may include an RF unit 168 and a barometer 112 for measuring the reference atmospheric pressure. In one embodiment, the RF unit 168 and barometer are located within the telemetry module 164, although they can be integrated with the processing unit 166 as well. The signal processing unit can be used to analyze physiologic signals and to determine physiologic parameters. The patient advisory module 166 may also include data storage, and a sub-module that contains the physician's instructions to the patient for therapy and how to alter therapy based on changes in physiologic parameters. The parameter-based physician's instructions are referred to as "the dynamic prescription," or DynamicRx™ (Savacor, Inc.). The instructions are communicated to the patient via the signaling module 166, or another module. The patient advisory module 166 is located externally and used by the patient or his direct caregiver. It may be part of system integrated with a personal digital assistant, a cell phone, or a personal computer, or as a "Stand-Alone" device (e.g., in one embodiment, the HeartPOD™ diagnostic and therapeutic drug management system) without combination with CRM apparatus. In one embodiment, the external patient advisory module comprises an external telemetry device, a signal processing apparatus, and a patient signaling device. In one embodiment, the patient advisory module is operable to obtain the sensor signal from the implantable sensor by telemetry through the patient's skin; obtain the atmospheric pressure from the barometer; and adjust the sensor signal indicative of a fluid pressure based at least in part upon the atmospheric pressure obtained by the barometer so that the adjusted sensor signal indicates the fluid pressure within the left atrium of the heart relative to the atmospheric pressure. In one embodiment the patient advisory module communicates with a remote site such as a doctor's office, clinic, hospital, pharmacy, or database. Revised patient instructions including the parameter-based dynamic prescription can be communicated back to the patient advisory module. This can be performed remotely via hard-wired telephone or fiberoptic cable networks or wirelessly using a host of communication technologies currently available. Data may be communicated in either direction and the Internet may be in part the conduit for such communication.

In one embodiment, the physiologic signals are analyzed and used to determine adjustable prescriptive treatment instructions that have been placed in the patient advisory module 6 by the patient's personal physician. Communication of the prescriptive treatment instructions to the patient may appear as written or graphic instructions on a display of the patient advisory module 6. These treatment instructions may include what medications to take, dosage of each medication, and reminders to take the medications at the appropriate times. In one embodiment, the patient advisory module 6 displays other physician-specified instructions, such as "Call M.D." or "Call 911" if monitored values become critical.

In an alternative embodiment, the treatment signal may be the numerical representation of the mean left atrial pressure in mm Hg, or the numerical representation of some other parameter indicative of fluid pressure in the left atrium. Physician specified treatments would be supplied to the patient in the form of a decoding reference providing different treatment instructions for specified ranges of left atrial pressure. Such a decoding reference could be written or printed instructions on a card that the patient keeps for reference. For example, a mean left atrial pressure (LAP) of 15 mm Hg could indicate the same treatment as a mean LAP of 16 mm Hg, both values being in a range indicating that the patient's heart failure is well compensated. An LAP of 25 mm Hg however would indicate decompensated CHF and would decode as different therapeutic instructions aimed at recompensating the state of CHF.

A third component of this system embodiment is designed for physician use. The third component is used to program the dynamic prescription and communicate it or load it into the patient advisory module 166. The third module may also contain stored data about the patient, including historical records of the physiologic signals and derived parameters transmitted from the patient implant and signaling modules. The third component may also communicate with external databases. In one embodiment, the third component is a physician input device, and includes a personal computer, a PDA, a telephone, or any other such device as is well known to those of skill in the art also comprising specific third component software or firmware programs.

In one embodiment, the second component (e.g., the patient advisory module 166) is in the form of one or more implants.

In one embodiment of the present invention, the first implant module (such as, for example, implantable module 5 of FIG. 1 and FIG. 2) may also contain an implant therapy unit, or ITU. The ITU generates an automatic therapy regime based upon the programmed dynamic prescription. The therapy may include, but is not limited to, a system for releasing bioactive substances from one or more implanted reservoirs, a system for controlling electrical pacing of the heart, and controllers for ventricular or other types of cardiac assist devices. For example, in one embodiment the sensor package is placed across the intra-atrial septum and serves as the atrial lead of a multichamber pacemaker. The physiologic sensor information is used to adjust pacing therapy such that pacing is performed only when needed to prevent worsening heart failure. One skilled in the art will appreciate that many systems or devices that control the function of the cardiovascular system may be used in accordance with several embodiments of the current invention.

In one embodiment of the invention, the advisory module 6 is programmed to signal the patient when it is time to perform the next cardiac status measurement and to take the next dose of medication. It will be recognized by those skilled in managing CHF patients that these signals may help the many patients who have difficulty taking their medication on schedule. Although treatment prescriptions may be complex, one embodiment of the current invention simplifies them from the patient's perspective by providing clear instructions. To assure that information regarding the best treatment is available to physicians, professional cardiology organizations such as the American Heart Association and the American College of Cardiology periodically publish updated guidelines for CHF therapy. These recommendations can serve as templates for the treating physician to modify to suit individual patient requirements. In one embodiment, the device routinely uploads data to the physician or clinic, so that the efficacy of the prescription and the response to parameter driven changes in dose can be monitored. This enables the physician to optimize the patient's medication dosage and other important treatments without the physician's moment-to-moment intervention.

In various embodiment of the invention, a device and method for dynamically diagnosing and treating cardiovascular illness in a medical patient are provided. In one embodiment, at least one physiological sensor is used to generate a signal indicative of a physiological parameter. In another embodiment, signal processing apparatus operable to generate a signal indicative of an appropriate therapeutic treatment based, at least in part, upon the signal generated by the physiological sensor, is also provided. In another embodiment a patient signaling device used to communicate the signal indicative of the appropriate therapeutic treatment to the patient is provided as well.

In one embodiment, a device and method for continuously or routinely monitoring the condition of a patient suffering from chronic cardiovascular disease are provided. As will be described in detail below, a system incorporating various embodiments of the invention monitors various physiologic parameters, such as the patient's left atrial pressure. Depending upon the magnitude of or changes in this pressure, for example, the system communicates a signal to the patient indicative of a particular course of therapy appropriate to manage or correct, as much as possible, the patient's chronic condition. In some embodiments, physician instructions and automated therapy are provided.

In one embodiment, the physiological sensor generates a signal indicative of a physiological parameter on or in the patient's body. In one embodiment, the signal processing apparatus generates a signal indicative of an appropriate therapeutic treatment based at least in part upon the signal generated by the physiological sensor. The patient signaling device may generate signals indicative of therapeutic treatments or courses of action the patient can take to manage or correct, as much as possible, the patient's condition.

In one embodiment, this method includes the steps of implanting one or more physiological sensors substantially permanently within the patient, operating the physiological sensor to generate a signal indicative of a physiological parameter, processing this physiological signal to generate a signal indicative of an appropriate therapeutic treatment, and communicating the appropriate therapeutic treatment to a user. In one embodiment, the user includes, but is not limited to, the patient, a caregiver, a medical practitioner or a data collection center.

In another embodiment, the system is combined with or incorporated into a CRM system, with or without physiologic rate control, and with or without backup cardioversion/defibrillation therapy capabilities.

In one embodiment, at least one indication of congestive heart failure (CHF) is monitored. Elevated pressure within the left atrium of the heart is the precursor of fluid accumulation in the lungs, which results in signs and symptoms of acute CHF. Mean left atrial pressure in healthy individuals is normally less than or equal to twelve millimeters of mercury (mm Hg). Patients with CHF that have been medically treated and clinically "well compensated" may generally have mean left atrial pressures in the range from 12 to 20 mm Hg. Transudation of fluid into the pulmonary interstitial spaces can be expected to occur when the left atrial pressure is above about twenty-five mm Hg, or at somewhat more than about thirty mm Hg in some patients with chronic CHF. Pulmonary edema has been found to be very reliably predicted by reference to left atrial pressures and less well correlated with conditions in any other chamber of the heart. Thus, the methods and apparatus of several embodiments of the invention may prove very useful in treating and preventing pulmonary edema and other adverse conditions associated with CHF. Pressure in the pulmonary veins, pulmonary capillary wedge position, and left ventricular end diastolic pressure (LVEDP) are generally indicative of left atrial pressure and are commonly used as surrogates of LAP. There are, however, specific conditions, that are well known to those skilled in the art, including cardiologists and physiologists, where these surrogates vary substantially from LAP and may be less predictive of impending heart failure. One example of such a condition is mitral valve stenosis where pulmonary edema develops despite a normal LVEDP due to a significant pressure gradient across the mitral valve. However, one of skill in the art will understand that several embodiments of the current invention can be used in conditions where the surrogates do not directly correlate with LAP. Other surrogate pressures that also, on specific occasion, indicate LAP include, but are not limited to: the pulmonary artery diastolic (PAD), mean pulmonary artery pressure or algorithms that estimate PAD from the right ventricular waveform, the right ventricular end diastolic, the right atrial pressure, and the central venous pressure, or the response of arterial pressure during forced expiration against a closed glottis or other resistance (Valsalva maneuver). Also included are other pressures, parameters or algorithms that are indicative of left atrial pressure that may be known to those skilled in the art.

An embodiment of the invention includes a permanently implanted device designed to define the presence of worsening CHF hours to days before the onset of symptoms and to provide for early preventative treatment according to the physician's individualized prescription. As such, an embodiment of the invention includes an integrated patient therapeutic system that determines therapeutic dosages for an individual patient based at least in part on internal physiologic signals. In another embodiment, the system consists of a small implantable sensor device and an external patient advisory module comprising a personal data assistant (PDA) and a telemetry module. The sensor system may be implanted into the patient's left atrial chamber by a transseptal catheterization procedure. There are already several thousand physicians in the U.S. and abroad with the experience and skills required for such device implantation. The implantation procedure can be performed on an outpatient basis in a hospital's cardiac catheterization laboratory. The implant may alternatively be placed at the time of open-heart or minimally invasive valve or bypass surgery where the surgeon, under direct, laparoscopic, or thorascopic vision, positions the device in the left atrium, left atrial appendage, or an adjacent pulmonary vein.

In one embodiment, the sensor system measures a left atrial pressure waveform, core body temperature and a cardiac electrogram, such as the intra cardiac electrogram (IEGM). Elevated left atrial pressure is the most accurate predictor of impending CHF, often preceding clinical symptoms by hours to days. Other embodiments of the left atrial pressure waveform may be used to diagnose a number of conditions, as listed in FIGS. 6A-6C. Core temperature is often depressed in acute CHF, but elevated prior to the development of fever in response to an infection, making core temperature a useful parameter for differentiating between these common conditions with similar symptoms but which require different treatments. The intracardiac electrogram may be useful in diagnosing arrhythmias and precipitating causes of worsening CHF.

FIG. 7 shows how left and right atrial pressure measurements may be combined with IEGM and core temperature measurement to diagnose a number of cardiac and non-cardiac conditions. The list of diagnostic states in FIG. 7 is exemplary, and by no means exhaustive of all the potential diagnostic states definable by the given parameters. Multiple states can exist simultaneously, for example, moderate CHF and rapid atrial fibrillation. The measured parameters can be used over large populations to define the probability of any given diagnostic state. Each diagnostic state may have a unique treatment. For example, mild CHF may be treated by increasing diuretic therapy, whereas rapid atrial fibrillation is treated with a drug that blocks AV node conduction. Many of the states listed can contribute to worsening CHF. Therefore, one of skill in the art will appreciate that several embodiments described herein can be used to treat not only CHF, but to treat cardiovascular disease in general.

The embodiments summarized above and described in greater detail below are useful for the treatment of cardiovascular disease, including congestive heart failure (CHF). CHF is an important example of a medical ailment currently not treated with timely, parameter-driven adjustments of therapy, but one that the inventors believe could potentially benefit greatly from such a strategy. Patients with chronic CHF are typically placed on fixed doses of an average of six drugs to manage the disease. The drug regimen commonly includes but is not limited to diuretics, vasodilators such as ACE inhibitors or A2 receptor inhibitors, beta-blockers such as Carvedilol, neurohormonal agents such as spironolactone, and inotropic agents usually in the form of cardiac glycosides such as, for example, digoxin. In addition, patients typically are taking other cardiovascular drugs to limit disease progression, symptoms or complications. Examples include 'statins' to lower cholesterol, nitrate to relieve chest pain, and aspirin or warfarin to prevent clotting.

1. Implantation and Anchoring a. Placement and Anchoring in the Left Atrium

Figure 8:
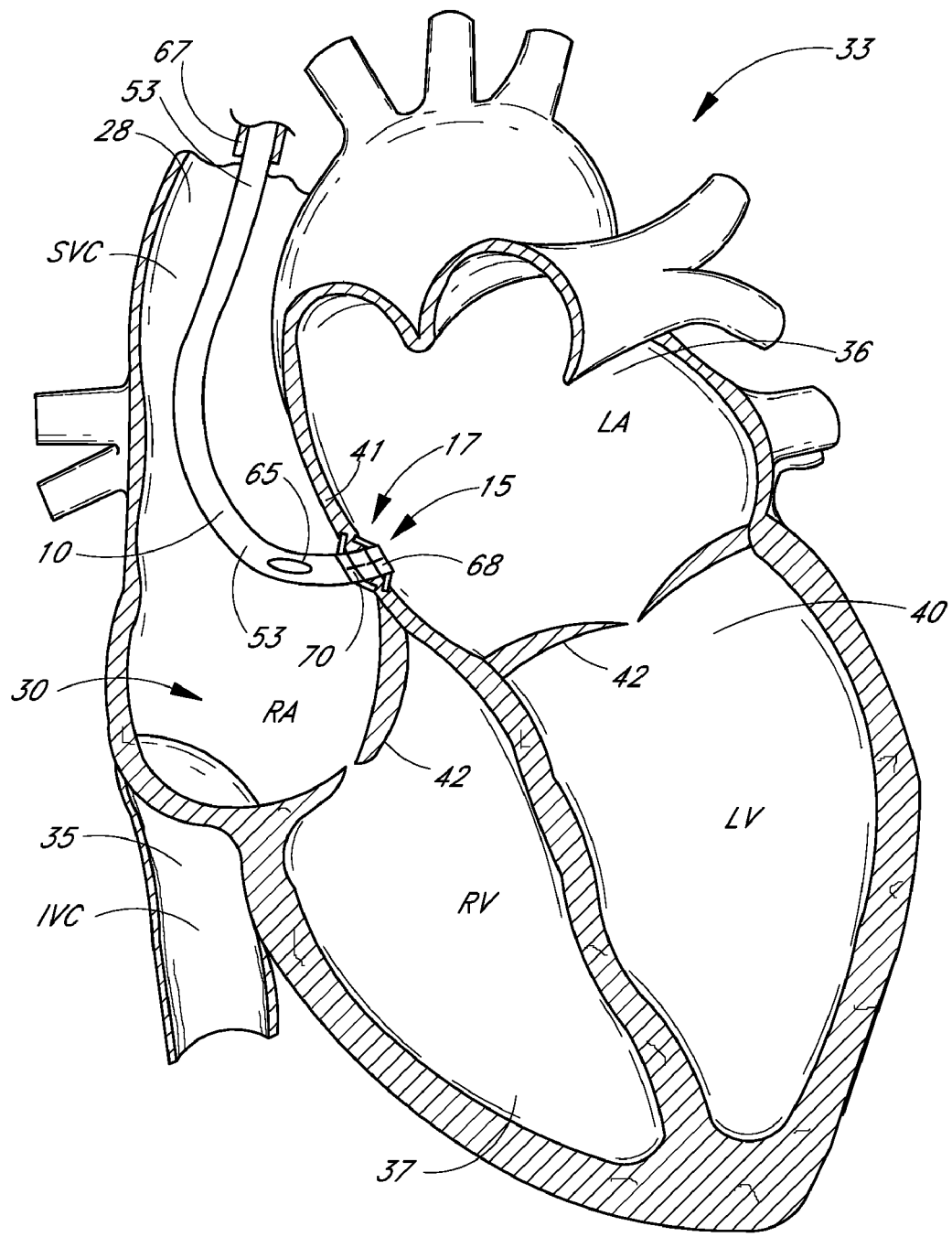
FIG. 8 shows the flexible lead of FIG. 13. The sheath has been withdrawn to deploy the proximal distal anchors on the right and left atrial sides of the atrial septum, and a pressure sensing transducer is in fluid contact with the patient's left atrium.

In one embodiment, such as that illustrated in FIG. 8, an implantable device is implanted percutaneously in the patient by approaching the left atrium 36 through the right atrium 30, penetrating the patient's atrial septum 41 and positioning one or more physiological sensors 15 in the atrial septum 41, on the septal wall of the left atrium 36, or inside the patient's left atrium 36. FIG. 8 shows an embodiment in which a sensor package 15 is deployed across the atrial septum 41. The sensor lead 10 is coupled to a physiological sensor or sensors 15 and anchoring apparatus at the lead 10 distal end 17. The anchoring apparatus includes a distal anchor 68 (sometimes referred to as an anchor, spring anchor, or distal foldable spring anchor) that expands in diameter upon release and is located at or near the distal tip of the sensor 15, and a proximal anchor 70 (sometimes referred to as an anchor, spring anchor, or proximal foldable spring anchor). The distal and proximal anchors 68, 70 are sufficiently close together that when deployed the two anchors 68, 70 sandwich the intra-atrial septum 41 between them, thus fixing the sensor/lead system to the septal wall. The intra-atrial septum 41 is typically between about 1 and about 10 mm thick. In one embodiment, the anchors 68, 70 are made of a highly elastic biocompatible metal alloy such as superelastic nitinol. The lead 10 may contain a lumen that exits the lead 10 at its proximal end. A stiffening or bending stylet can be inserted in the lumen to aid in passage of the sensor(s) and lead 15, 10. After a transseptal catheterization has been performed (as described below), a delivery sheath/dilator system of diameter sufficient to allow passage of the sensor/lead system is placed from a percutaneous insertion site over a guidewire until the distal end of a sheath 67 is in the left atrium 36. Left atrial position can be confirmed under fluoroscopy by contrast injection, or by the pressure waveform obtained when the sheath 67 is connected to an external pressure transducer. To aid the procedure, the sheath 67 may include a proximal hemostasis valve to minimize air entrainment during device insertion. A side port with a stopcock is useful to aspirate any remaining air and to inject radiographic contrast material. Additionally, later sheath 67 removal may be facilitated by using a "peel-away" type of sheath. These features of vascular sheaths are commercially available and well know to those familiar with the art. With the spring anchors 68, 70 folded and forming a system with minimal diameter, the system is loaded into the sheath 67 and advanced until the distal anchor 68 just exits the sheath 67 in the left atrium 36 and is thus deployed to its sprung diameter. The sheath 67 is carefully withdrawn without deploying the proximal anchor 70 and the sheath 67 and sensor/lead system are withdrawn as a unit while contrast is injected through the sheath 67 around the sensor lead until contrast is visible in the right atrium 30. The proximal sheath 67 is further withdrawn, allowing the proximal anchor 70 to spring to its unloaded larger diameter, thus fixing the distal portion of the sensor lead to the septum 41.

It will also be apparent that, in several embodiments, a similar sensor/lead system can be inserted through an open thoracotomy or a minimally invasive thoracotomy, with the anchoring system fixating the sensor/lead to a location such as the free wall of the left atrium, the left atrial appendage, or a pulmonary vein, all of which provide access to pressures indicative of left atrial pressure.

Figure 9:
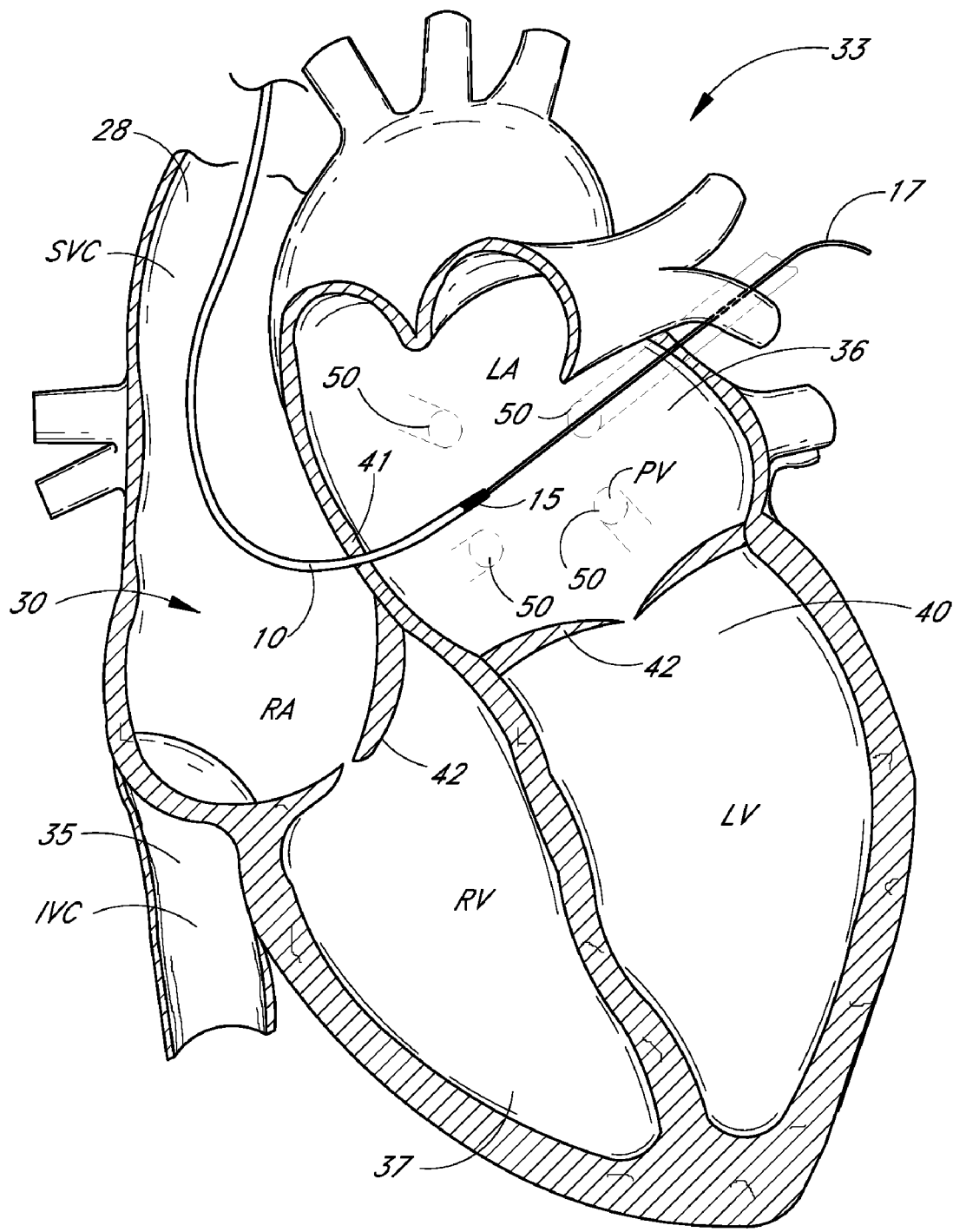
FIG. 9 depicts a method for anchoring a flexible electrical lead within the patient's heart.

In one alternative embodiment, a flexible lead 10 is partially advanced into a pulmonary vein 50 connected to the left atrium 36 such that one or more physiological sensors 15 disposed on the flexible lead 10 a predetermined distance from its distal end 17 are positioned within the left atrium 36 or the pulmonary vein 50, as shown in FIG. 9. In another embodiment, the distal portion 17 of the flexible lead 10 is partially advanced into the left atrial appendage such that anchoring apparatus will be occlusive of the appendage, for example as taught by Lesh et al. in U.S. Pat. No. 6,152,144, incorporated by reference herein. The physiologic sensors 15 are positioned on the lead 10 proximal to the occlusive anchors so that they sense conditions in the left atrium.

Figure 12:
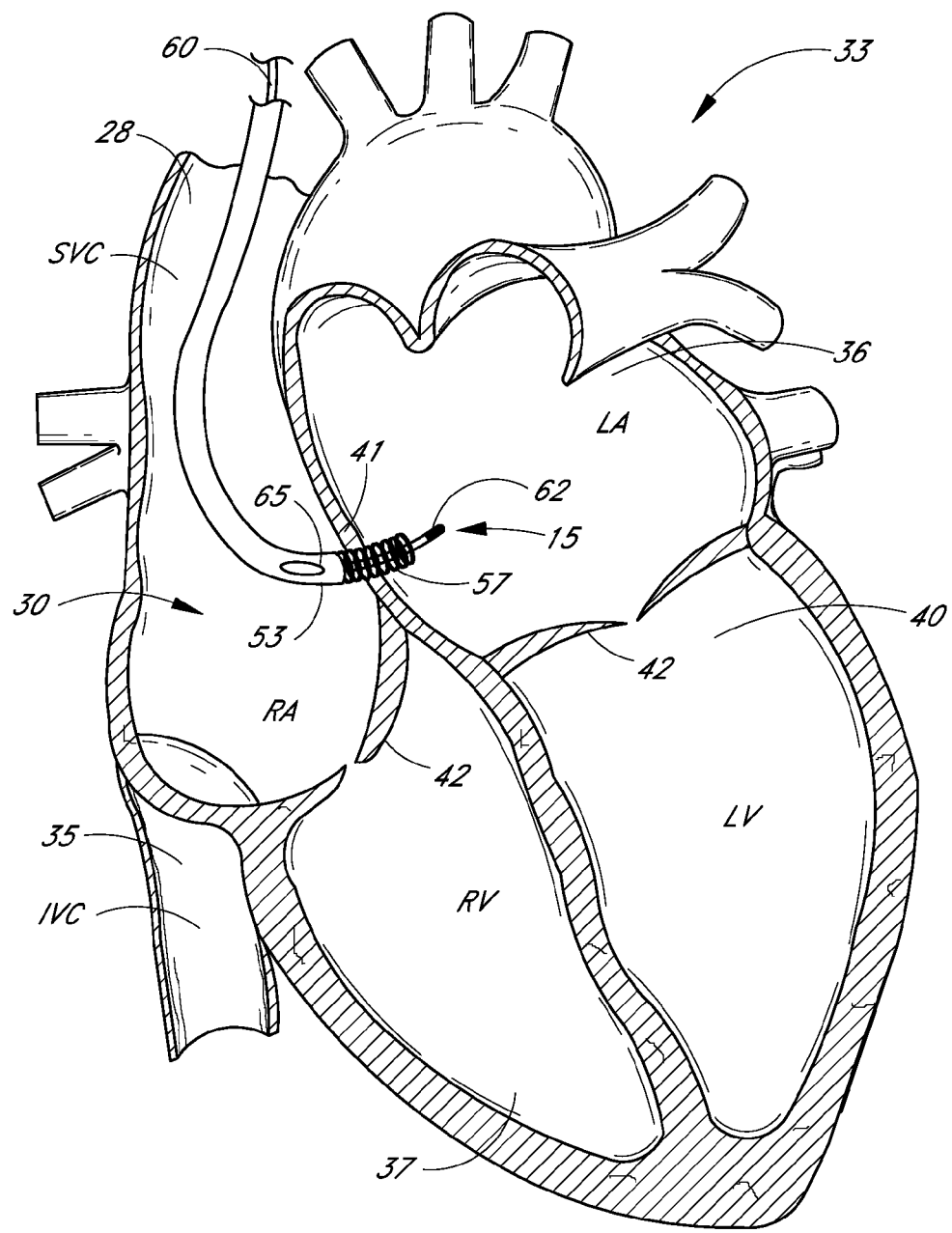
FIG. 12 shows the apparatus depicted in FIG. 11, with a pressure sensing transducer in place in the patient's left atrium.
Figure 14:
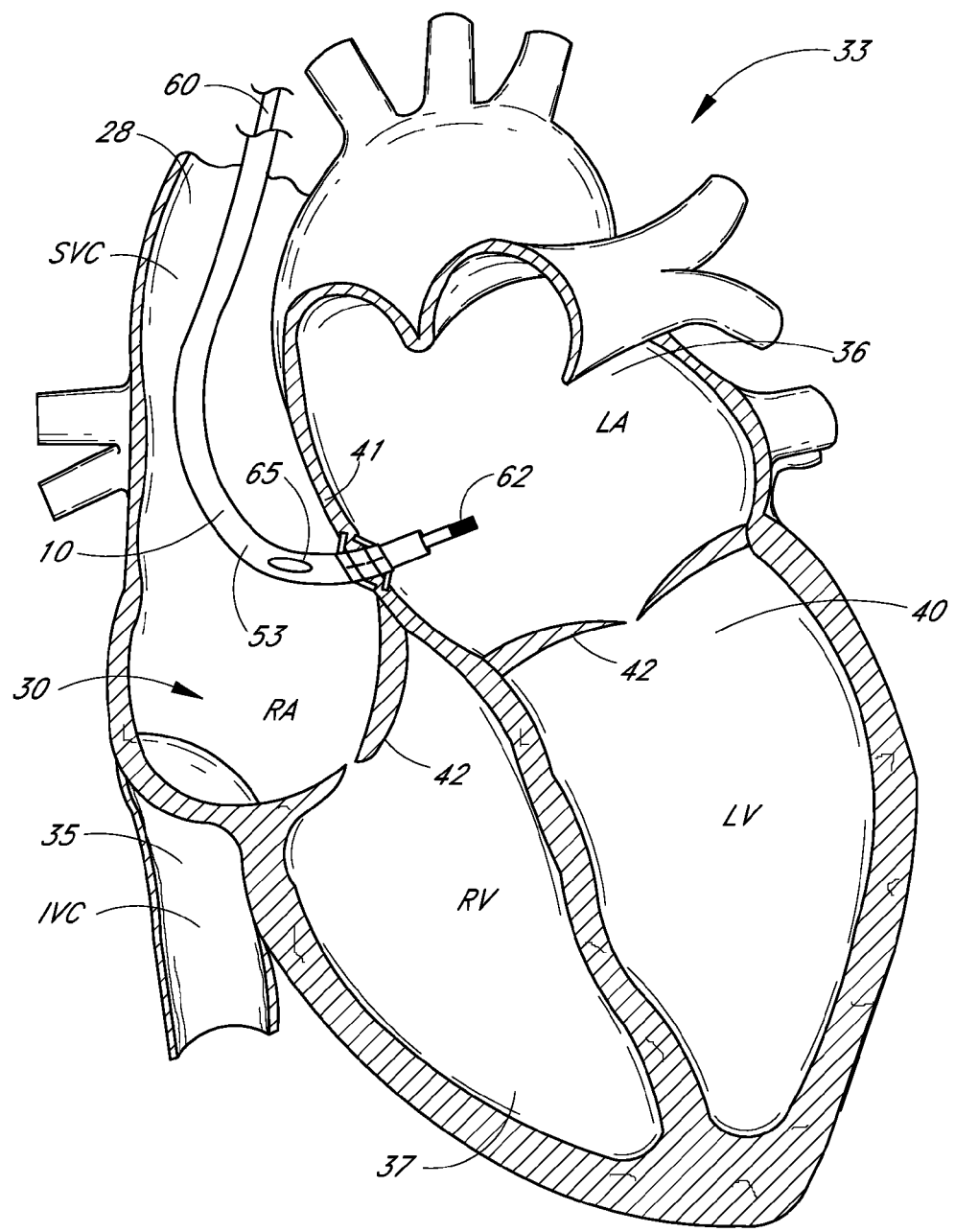
FIG. 14 shows the flexible lead of FIG. 15 and FIG. 16, with a pressure sensing transducer in place inside the patient's left atrium.
Figure 15:
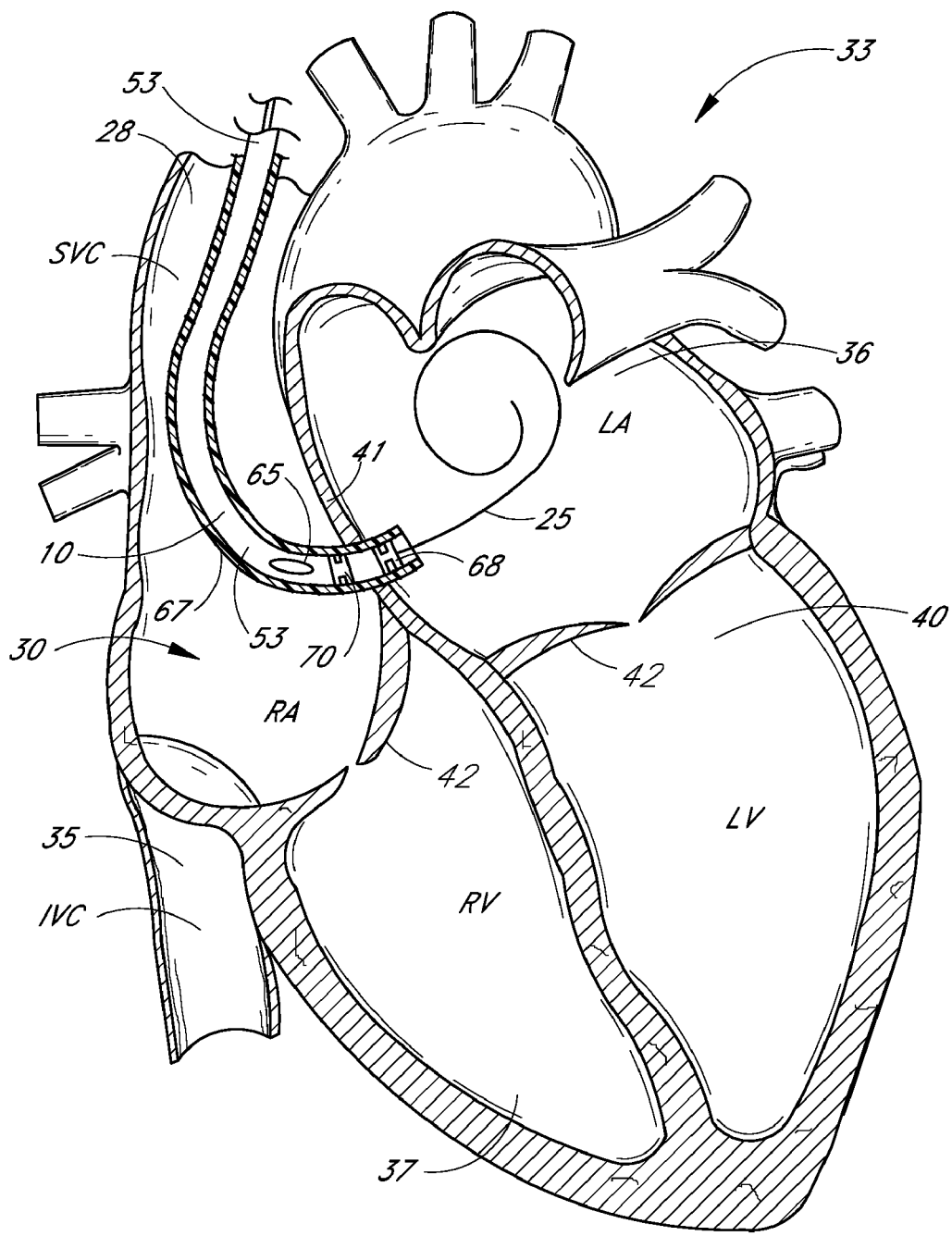
FIG. 15 depicts a flexible lead including deployable anchors carried inside a removable sheath and placed through the atrial septum.
Figure 16:
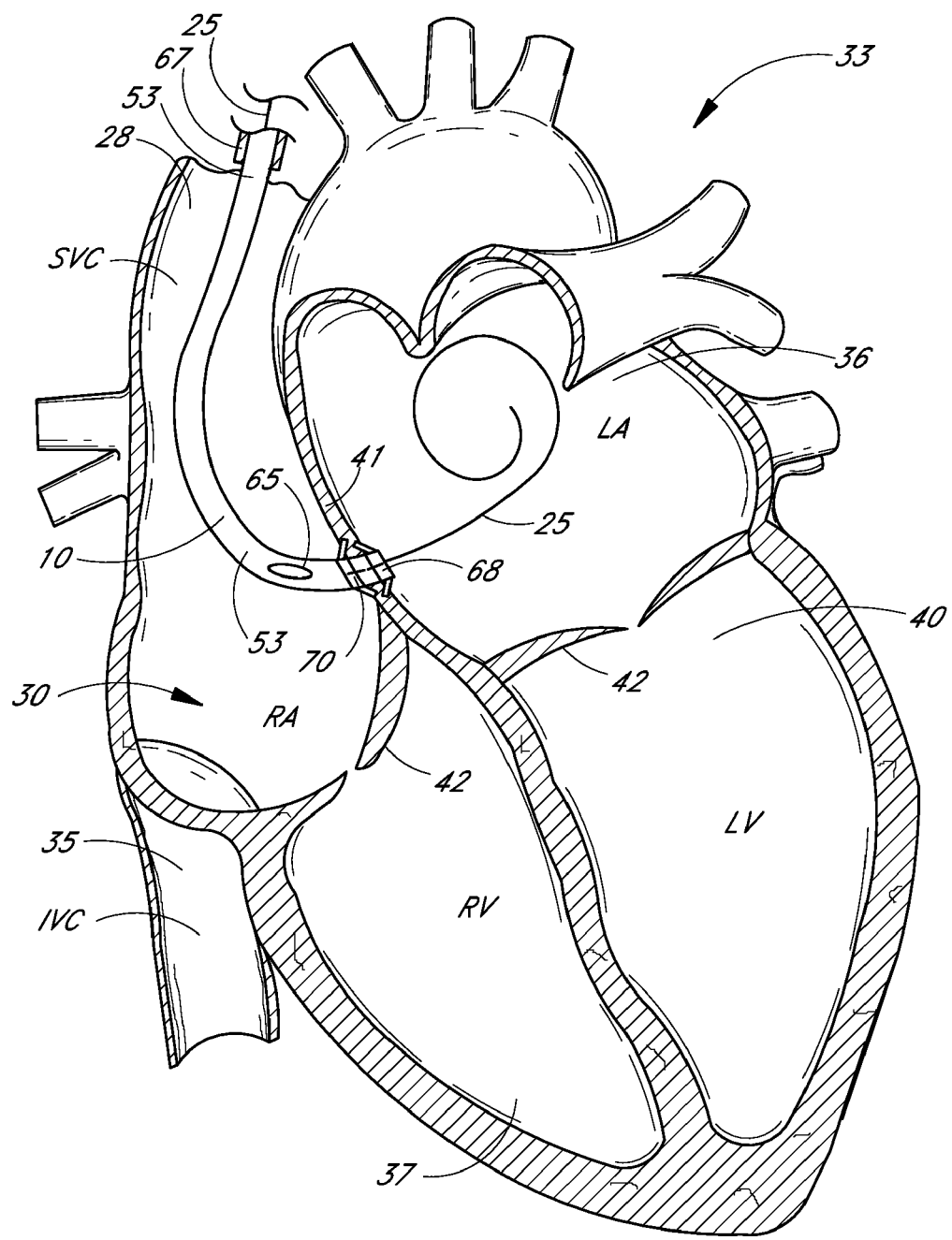
FIG. 16 shows the flexible lead of FIG. 15 with the sheath withdrawn to deploy the anchors on opposite sides of the atrial septum.

In other embodiments, such as those shown in FIG. 12 and FIG. 14, a first lead component 53 includes an anchoring apparatus, for example, a helical screw 57, which is advanced to the atrial septum 41. The anchoring apparatus is deployed to anchor the first lead component 53 into the patient's atrial septum 41. A second lead component 60 includes a physiological sensor, for example, a pressure transducer 62, which is advanced along the first lead component 53 until the second lead component 60 is in a position such that the physiological sensor is positioned within the patient's left atrium 36.

b. Implantation in the Left Atrium

Referring to the embodiment depicted in FIG. 8, the system is implanted through the left atrial septum 41 such that the pressure sensor 15 is exposed to the pressure in the left atrial chamber 36 of the heart. The left atrial septum 41 can be accessed from the right atrium 30 through the inferior or superior vena cava 35, 28, as is well known to those skilled in the arts of, for example, pacemaker lead placement, catheter ablation for control of arrhythmias originating in the left atrium or pulmonary veins, percutaneous repair of the mitral valve, and percutaneous closure of an atrial septal defect. In one embodiment, the flexible lead 10 and pressure transducer 15 are anchored to the atrial septum 41. This placement can be achieved using vascular access techniques that are well-known to those familiar with the performance of invasive cardiovascular procedures, in particular, interventional cardiologists, electrocardiologists, and cardiovascular surgeons. These procedures are commonly performed with the aid of visualization techniques, including standard fluoroscopy, cardiac ultrasound, or other appropriate visualization techniques used alone or in combination.

Access to the central venous circulation may be achieved by use of the standard Seldinger technique through the left or right subclavian vein, the right or left internal jugular vein, or the right or left cephalic vein. Alternatively, access may be made via the Seldinger technique into the right femoral vein. In either case, a Brockenbrough catheter and needle are used to pierce the atrial septum 41 for access to the left atrium 36, as described below.

i. Superior Venous Access (Subclavian or Internal Jugular Vein)

Figure 10:
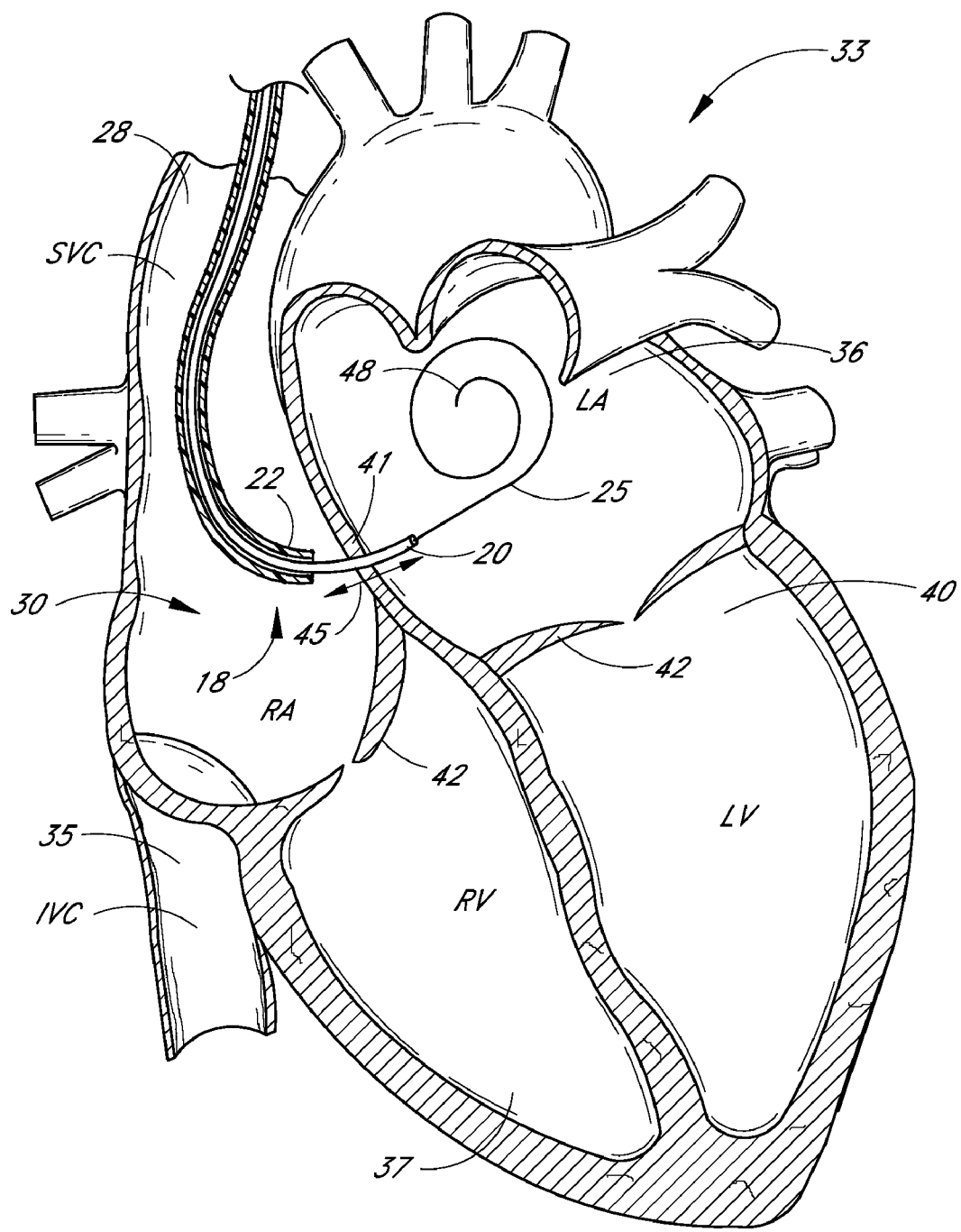
FIG. 10 is a schematic sectional view of a patient's heart illustrating an atrial septal puncture for implanting one embodiment of the current invention.

FIG. 10 provides a schematic sectional view of the patient's heart 33 and shows the apparatus used to access the left atrium 36. FIG. 10 depicts an access assembly 18 comprising a Brockenbrough catheter 20 inside a sheath 22, with a flexible guidewire 25 residing within the Brockenbrough catheter 20. As FIG. 10 indicates, the access assembly has been placed through the superior vena cava 28 into the right atrium 30 of the heart 33. FIG. 10 also shows the inferior vena cava 35, the left atrium 36, the right ventricle 37, the left ventricle 40, the atrial septum 41 that divides the two atria 30, 36, and the valves 42 between the right atrium 30 and right ventricle 37, and the left atrium 36 and left ventricle 40. The reader will appreciate that the view of FIG. 10 is simplified and somewhat schematic, but that nevertheless FIG. 10 and the other views included herein will suffice to illustrate adequately the placement and operation of an embodiment of the present invention.

ii. Placement of the Lead

With the access assembly 18 in place within the right atrium 30, the Brockenbrough catheter 20 is used to pierce the atrial septum 41 by extending the Brockenbrough needle (not shown) through the atrial septum 41 into the left atrium 36. In the figures, the atrial septum 41 has been pierced by the needle, the catheter 20 has been advanced over the needle, and the needle has been withdrawn from the catheter 20, leaving the catheter 20 in place inside the left atrium 36. Optionally, a guidewire 25 may be advanced through the needle into the left atrium 36 before or after advancing the catheter 20, or it may be placed into the left atrium 36 through the catheter 20 alone after the needle has been withdrawn.

As indicated by the arrows 45 in FIG. 10, the sheath 22 may extend into the left atrium 36, or it may remain on the proximal side of the atrial septum 41 within the right atrium 30. FIG. 10 shows the guidewire 25 extended from the end of the Brockenbrough catheter 20 to secure continuous access into the left atrium 36. As depicted therein, the guidewire 25 has a curled, "pig-tail" style distal tip 48 to better secure the guidewire 25 within the left atrium 36 and to safeguard against inadvertent withdrawal through the atrial septum 41. Alternatively, a "floppy tip" guide wire may be used, which can be safely advanced well into one of the pulmonary veins, again to safeguard against inadvertent withdrawal through the atrial septum 41. Once the guidewire 25 is securely in place in the left atrium 35, the Brockenbrough catheter 20 may be withdrawn so that the flexible lead 10 may be placed through the peel-away sheath 22.

With the guidewire 25 securely in place with its distal tip 48 inside the left atrium 36, the flexible lead 10 may be advanced into the left atrium 36. The flexible lead 10 might itself include a central lumen configured to receive the proximal end of the guidewire 25, thereby allowing the flexible lead 10 to be advanced down the guidewire 25 toward the left atrium 36. More commonly, an exchange catheter, which may be in the form of a peel-away sheath 22, will be advanced down the guidewire 25 and placed into the left atrium 36, the guidewire 25 may then be withdrawn, after which the flexible lead 10 will be advanced down the exchange catheter and into position.

In one embodiment, a peel-away sheath 22 is used to allow the sheath to be removed once the distal end of the lead 10 is implanted. The peel-away feature is used if the proximal end of the lead 10 is permanently attached to the coil housing assembly (described above). Alternatively, a non-peel-away sheath with proximal hemostasis valve and side port as described above can be used, for example, if the lead is detachable from the coil assembly and if the lead or a stiffening stylet fixed within the central lumen of the lead is long enough to remove the sheath while maintaining control over the proximal end of the lead. These configurations of sheaths and methods of sheath removal are well known to those skilled in the art.

iii. Anchoring the Sensor and Lead

Once the pressure transducer 15 of the flexible lead 10 is positioned within the left atrium 36, the lead 10 should be anchored in place to ensure that the pressure transducer 15 stays reliably and permanently in the desired location.

One method for anchoring the flexible lead 10 in place is depicted in FIG. 9, which is a somewhat schematic depiction of the major structures of the heart. FIG. 9 shows the four pulmonary veins 50 that connect to the left atrium 36. In the particular apparatus depicted in FIG. 9, the flexible lead 10 includes a pressure transducer 15 located on the body of the lead 10 a predetermined distance proximal of the distal end 17 of the lead 10.

Referring back to FIG. 9, the distal end 17 of the flexible lead 10 in this embodiment can be bent by the operator in much the same way as a distal tip such as might be found on a steerable angioplasty guidewire or another similar device. This feature assists the operator in steering the flexible lead 10 into a selected one of the pulmonary veins 50, with the pressure transducer 15 disposed within the interior space of the left atrium 36, or even within the pulmonary vein itself. Placement of the pressure transducer 15 within the pulmonary vein is effective because pressures within the pulmonary vein are very close to pressures within the left atrium. It will be appreciated by those skilled in the art that visualization markers (not shown) may be provided at appropriate locations on the flexible lead 10 to assist the operator in placing the device as desired. With the flexible lead 10 in place as shown, the body's own natural healing mechanism may permanently anchor the flexible lead 10 in place both at the penetration site through the atrial septum 41, and where the flexible lead 10 contacts the interior surface of the pulmonary vein 50 in which the tip of the lead 10 resides. The pressure transducer 15 might also be placed at locations such as the left atrial appendage (not shown in FIG. 9) where the pressure is nearly the same as the left atrium 36, or the left ventricular cavity, where at identifiable phases of the cardiac cycle the pressure is momentarily nearly the same as that in the left atrium 36.

Figure 11:
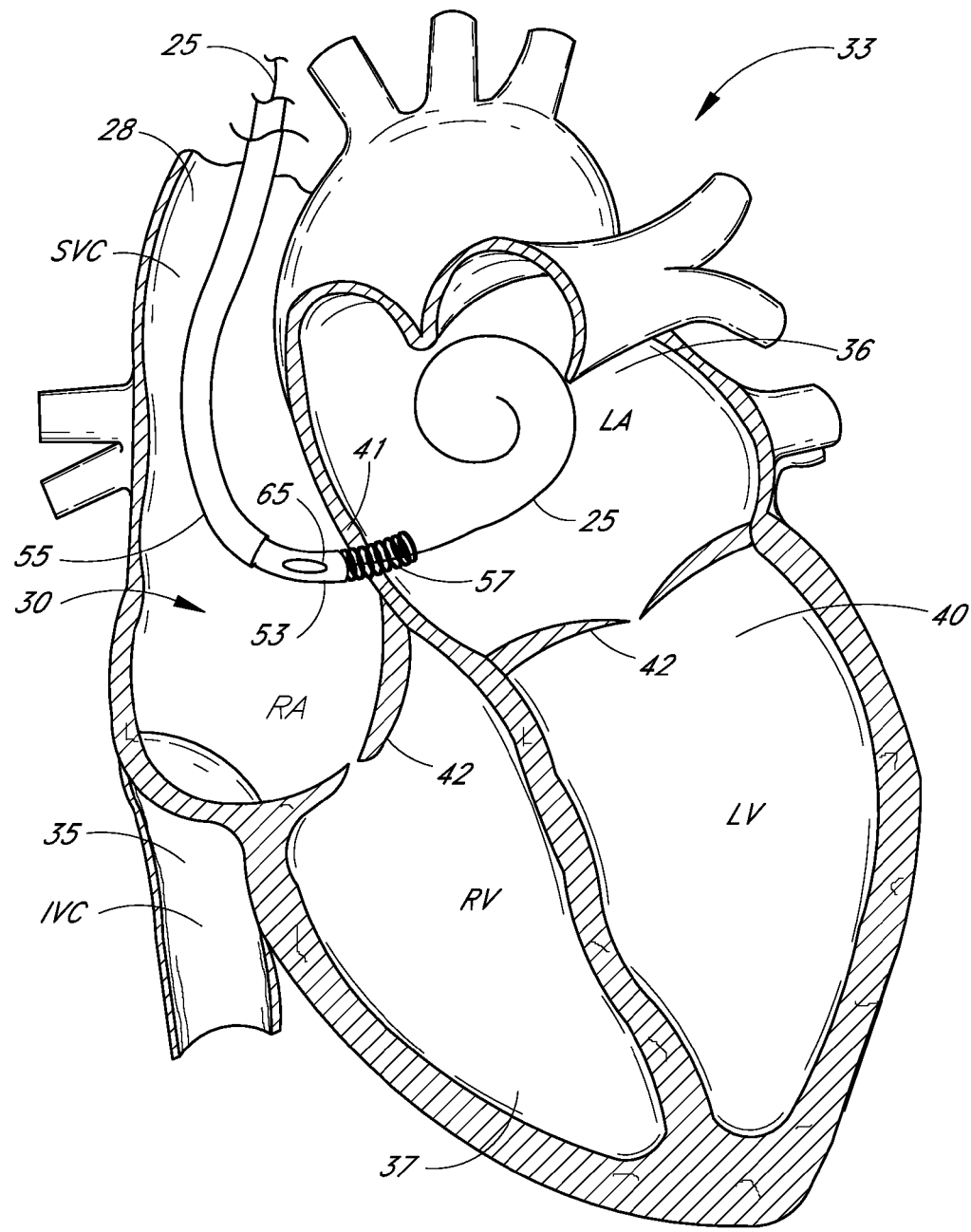
FIG. 11 shows another method for anchoring a lead within the heart, which includes a helical screw for advancement into the patient's atrial septum.

FIG. 11 and FIG. 12 show alternative methods and devices for anchoring the pressure transducer 15 in a location appropriate for measuring pressures within the left atrium 36. The lead in this embodiment includes a helical screw 57 for anchoring the lead to the atrial septum 41. Similar configurations are used in some leads for pacemakers and thus may be familiar to those skilled in the art.

iv. Two-Component Lead with Optional Second Pressure Transducer

Referring now specifically to FIG. 11, the guidewire 25 is shown positioned across the atrial septum 41 between the left atrium 36 and the right atrium 30. A first lead component 53 is delivered over the guidewire through an appropriate guiding catheter 55 or sheath. This first lead component 53 includes a helical screw 57 on its exterior surface. The helical screw 57 is advanced into the tissue of the atrial septum 41 by applying torque to the shaft of the first lead component 53. The helical screw 57 could also be coupled to a hollow or solid cylindrical mandrel (not shown), or to a spirally wound mandrel (also not shown) disposed along substantially the entire length of the first lead component. When the helical screw 57 has been turned and advanced sufficiently into the atrial septum 41, the guidewire 25 and guiding catheter may then be withdrawn leaving the first lead component 53 anchored securely in place.

In one embodiment, a second lead component 60 is advanced as shown in FIG. 12 through a central lumen in the first lead component 53. The first and second lead components 53, 60 are sized and configured so that when the second lead component 60 is fully advanced with respect to the first lead component 53, a left atrial pressure transducer 62 at the end of the second lead component 60 protrudes by an appropriate predetermined amount into the left atrium 36. In one embodiment, the second lead component 60 is then securely fixed with respect to the first lead component 53.

It should be noted that the embodiments depicted in FIG. 11 and FIG. 12 includes a second pressure transducer 65 on the exterior of the first lead component 53 that may be exposed to pressure within the right atrium 30. This illustrates, in a simplified way, the general principle, in which a pressure transducer is used to measure fluid pressure within the left atrium, but in which one or more additional transducers or sensors may also be used to detect a physiologic condition other than left atrial pressure. These physiologic conditions may include pressures in locations other than the left atrium 36, and physical parameters other than pressure.

v. Alternative Anchoring Systems and Methods

Figure 13:
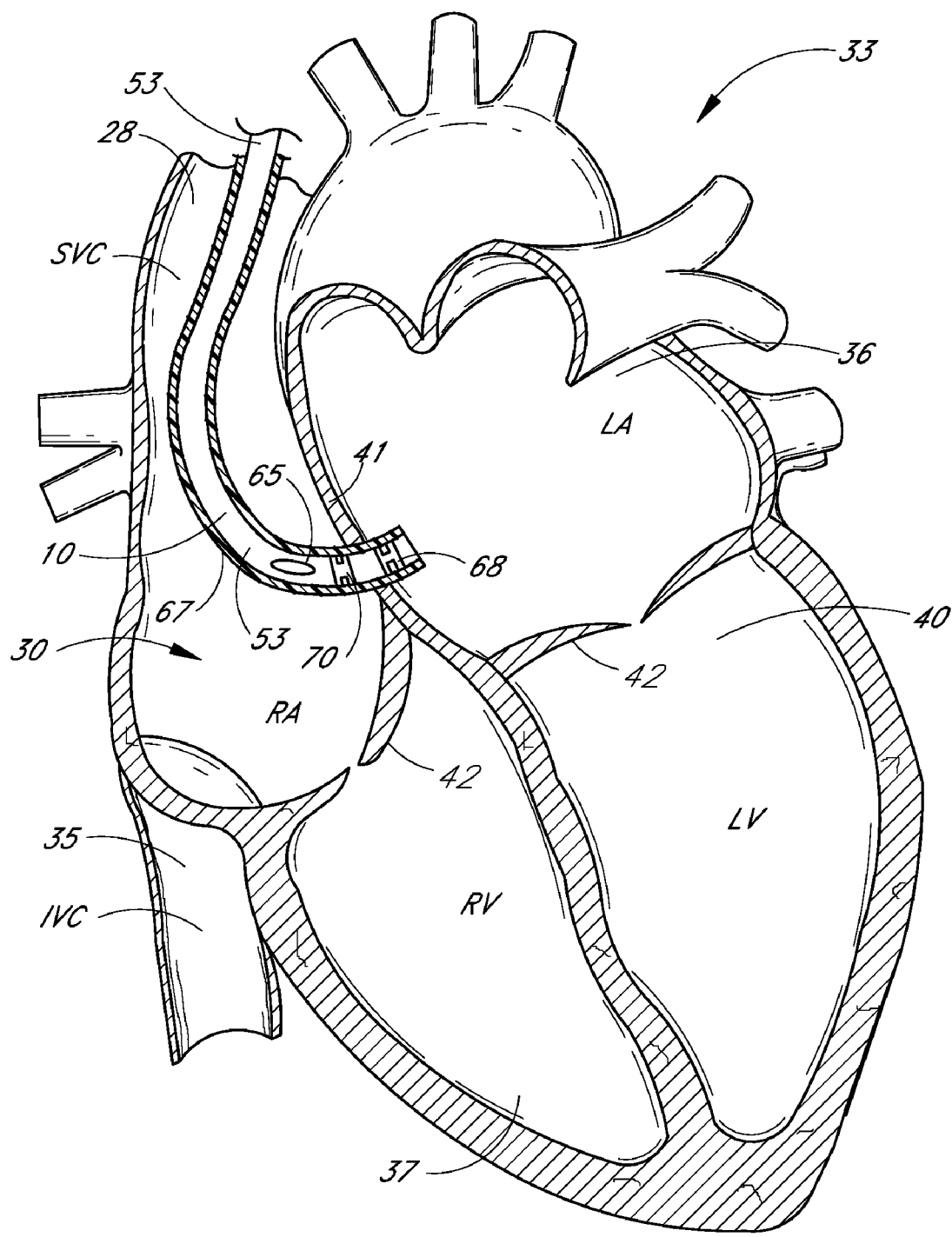
FIG. 13 is a schematic sectional view of a patient's heart showing a part of an embodiment of the invention positioned therein.

FIG. 8 and FIG. 13 through FIG. 16 show embodiments of the flexible lead 10, in which folding spring-like fins or anchors deploy to anchor the lead in place in the atrial septum 41. Referring specifically to FIG. 13, a first lead component 53 is advanced through a sheath 67, the sheath 67 having been advanced across the atrial septum 41. In this embodiment, the first lead component 53 includes distal anchors 68 and proximal anchors 70 that lie folded and are held in place inside the interior lumen of the sheath 67. When the first lead component 53 and sheath 67 are properly positioned, which will generally involve the use of fluoroscopy or an alternative technique for imaging, the operator may carefully withdraw the sheath 67 from around the first lead component 53. As the distal and proximal anchors exit the sheath 67, they deploy themselves (as depicted in FIG. 8) on either side of the atrial septum 41, thereby anchoring the first lead component 53 securely in place. Similar anchors are sometimes used with leads for pacemakers and other medical devices where permanent anchoring is desired, and the operation of these anchors thus will not be entirely unfamiliar to the knowledgeable reader.

Referring now to FIG. 14, a second lead component 60 is advanced through a central lumen of the first lead component 53 after the guidewire 25 (see FIG. 15 and FIG. 16) and sheath 67 are removed. As in the previous embodiment, a left atrial pressure transducer 62 is carried at the distal end of the second lead component 60. Again, the first and second lead components 53, 60 are sized and configured with respect to one another so that the left atrial pressure transducer 62 protrudes from the first lead component 53 an appropriate amount into the left atrium 36. In addition, as in the previous embodiment, a second pressure transducer 65 on the exterior of the first lead component 53 allows for the measurement and transmittal of pressure within the right atrium 37.

Other anchoring methods may be devised by those skilled in the relevant arts. Moreover, approaches have been described by which the lead is positioned between the left atrium and an exit site from the patient's superior venous circulation. Alternate lead routes and exit sites may find use as well.

vi. Surgical Methods of Device Implantation

As described above, percutaneous transvenous implantation methods are used in accordance with several embodiments of the current invention. One skilled in the art will understand that alternative lead routes and exit sites from the venous system may also be used. One important class of alternative implantation methods consists of surgical implantation through the wall of the heart, either directly into the left atrium through the left atrial free wall or left atrial appendage, into the left atrium via a pulmonary vein, into the left atrium through the intra-atrial septum via the right atrial free wall, or directly into a pulmonary vein.

In one embodiment, the pressure transducer is implanted in the atrial free wall or in the wall of the atrial appendage. As described above, in one embodiment, at these locations the pressure sensing surface of the transducer is exposed to left atrial pressure, and the body of the transducer extends through the wall of the atrium or atrial appendage. A flexible lead from the implanted transducer provides signal connection to a telemetry antenna coil that the surgeon implants near the surface of the skin. In another embodiment, this coil may be connected directly to the implanted pressure transducer on the outside surface of the heart, without need for a flexible lead. In yet another embodiment, the flexible lead provides signal connection to a CRM generator housing located near the surface of the skin.

c. Pulmonary Vascular Implant

Vascular stents are implants that are deployed in blood vessels to support the size of the vascular channel and maintain adequate blood flow. A stent may also be used to anchor another type of device in a fixed location within the cardiovascular system. U.S. Pat. No. 5,967,986, incorporated by reference herein, describes a stent coupled to one or more pressure transducers for the purpose of measuring blood flow in a vessel. In one embodiment of the current invention, a stent is used to support and anchor the sensor measuring a signal indicative of left atrial pressure. As mentioned above, the pressure in the pulmonary veins is substantially identical to that in the left atrium. Thus, in one embodiment of this invention, the pressure sensor is anchored in a pulmonary vein by means of a stent expanded within the vein.

In one embodiment of the current invention, a method and apparatus for continuous ambulatory detection, diagnosis and treatment of acute congestive heart failure is provided. It will be understood that the current invention may be implemented using digital signal processing methods in which various input signals are sampled and the described procedures are performed on a set of samples. Hence, a periodic determination of the physiological parameter of interest is within the definition of the term continuous. In one embodiment, a percutaneously implantable system comprises a hermetically sealed pressure transducer/communications module mounted on an unexpanded vascular stent-like member. In one embodiment, the stent-like member is a cylindrical vascular stent such as a balloon expandable or self-expanding metallic stent similar to those used to treat vascular stenosis such as atherosclerotic stenosis of a coronary or peripheral artery. The pressure transducer/communications module is mechanically coupled to the unexpanded stent and the stent/transducer module is mounted on a delivery catheter constituting a stent/transducer delivery system. The stent/transducer delivery system is percutaneously inserted into a patient's body via the venous or arterial system.

In one embodiment, the delivery system courses over a guide wire that has been positioned from proximal to distal, starting outside the patient, percutaneously entering into the venous system and into the right atrium, through the right ventricle and into a branch of the pulmonary artery. The stent/transducer module is then advanced over the guide wire into the selected branch of the pulmonary artery that is approximately the diameter of the expanded stent/transducer module.

In another embodiment, a standard transseptal catheterization procedure is performed to place a guide wire that courses from proximal to distal starting outside the patient percutaneously into the venous system into the right atrium, across the intra-atrial septum, into the left atrium and finally into one of the four pulmonary veins. The stent/transducer delivery system is then advanced over the guide wire until the unexpanded stent/transducer is positioned in the pulmonary vein that is approximately the diameter of the expanded stent/transducer module. The stent is then expanded such that the cylinder described by the stent is coaxially in contact with the vessel wall confining the transducer/communications module so that its outer surface contacts the vessel wall.

2. Pressure Transducer a. Pressure Sensor Locations

In one embodiment of the invention, the apparatus and/or method for treating cardiovascular disease includes one or more sensors, such as pressure sensors. In one embodiment, the pressure sensor is located in the atrial septum, the left atrial appendage, the left atrial free wall, one of the pulmonary veins, or any other location in pressure communication with the left atrium, for example, but not limited to, the right atrium, the central veins, or any location as known to those of skill in the art suitable for measuring a pressure related to the pressure in the pulmonary veins, the pulmonary capillary wedge pressure, the pulmonary artery diastolic pressure, the left ventricular end diastolic pressure, or the right ventricular end diastolic pressure. In one embodiment, the pressure signal includes a pulmonary vein pressure, a pulmonary capillary wedge pressure, a pulmonary artery diastolic pressure, a left ventricular end diastolic pressure, a right ventricular end diastolic pressure, right atrial pressure, or the pressure measured in the intrathoracic space, or the central veins. In another embodiment, the signal includes algorithms that estimate pulmonary artery diastolic pressure from the right ventricular waveform, the right ventricular end diastolic pressure, the right atrial pressure, or the response of the arterial blood pressure to the Valsalva maneuver. In yet another embodiment, signals indicative of left atrial pressure include spatial parameters (e.g., dimension of chambers), septal shape, position, motion, and acceleration.

b. Pressure Sensor Design

In one embodiment, the physiological sensor includes a pressure transducer. In one embodiment, the pressure transducer is contained within a hermetically sealed sensor package, or module. The sensor package may be provided in a wide range of sizes and shapes. In one embodiment, the sensor package is cylindrical, and is between about 1 mm and 5 mm long, and 3 mm in diameter. In another embodiment, the sensor package is between about 5 mm and about 15 mm long. In another embodiment the package is about 8 mm long, and about 3 mm in diameter. In one embodiment the package is less than about 1 mm in diameter. In another embodiment, the package is less than about 10 mm long. Micro electromechanical system (MEMS) pressure sensor devices may also be used. In one embodiment, the package may be rectangular, square, spherical, oval, elliptical, or any other shape suitable for implantation. In one embodiment, the sensor package is rigid, and in another embodiment, the sensor package is flexible.

In one embodiment, the sensor package includes a titanium cylindrical housing that is closed at one end by titanium foil membrane. In one embodiment, the foil membrane is between about 0.001 to 0.003 inches, between about 0.003 inches and about 0.005 inches, or less than 0.001 inches thick. In another embodiment, the foil membrane is between about 0.001 inches to about 0.002 inches (about 25 microns to about 50 microns) thick, and about 0.08 to 0.10 inches (about 2.0 to 2.5 mm) in diameter. Foil diaphragms of this type have relatively low compliance, meaning that they exhibit relatively little strain, or displacement, in response to changes in pressure. For example, in one embodiment, a 2.5 mm diameter by 50-micron thick titanium foil diaphragm has a displacement at its center of only about 4.3 nanometers per mm Hg pressure change. Higher compliance is a disadvantage for implantable pressure sensors because tissue overgrowth can limit the relatively larger motion of a high compliance diaphragm, causing errors in the sensed pressure reading.

In one embodiment, resistive strain gauges are bonded to the inside surface of the foil.

In one embodiment, the titanium cylindrical housing comprises an application specific integrated circuit (ASIC or "chip") or "measurement electronics." Measurement electronics are contained within the housing, connected to the strain gauges by fine gold wires. The other end of the housing is sealed by a ceramic feed-through that is brazed to a titanium cylinder.

In one embodiment, the pressure of the gas sealed in the cylinder is slightly lower than the lowest external pressure anticipated, so that the net force on the foil will be inward under normal conditions of operation, forming a concave membrane shape. The advantage of maintaining a concave membrane shape throughout the pressure range of operation is that it avoids potential pressure measurement artifacts that are known to sometimes occur when a pressure sensing membrane transitions between a concave and a convex shape, a phenomenon known as "oil-canning." In one embodiment, oil-canning is avoided by using a transducer diaphragm that has low compliance, with low compliance as described above, and that is nearly flat in the absence of a pressure differential. In one embodiment, the diaphragm is about 2.0 to 2.5 mm in diameter and is within about 25 microns of flat in the absence of a pressure differential. In another embodiment, the diaphragm thickness is maximized to maximize flatness and minimize compliance, consistent with the sufficient compliance to derive a useable transducer signal.

In one embodiment, the pressure sensor includes temperature compensation so that pressure measurements will not be affected by temperature change. This also provides the temperature at the site of the sensor. In one embodiment, temperature compensation or modulation is achieved by using multiple resistive strain gauges arranged in a Wheatstone bridge, such that the electrical voltage output of the bridge is proportional to the ratio of two or more resistances, as is well known in the art of electrical measurements. By selecting resistive strain gauges with substantially identical temperature coefficients, the intrinsic output of the bridge is made to be temperature independent. However, the overall response of the pressure transducer may still be temperature dependent because of imperfect matching of the resistive strain gauges, or due to other factors, such as the ideal gas law behavior of the gas sealed within the chamber, or different thermal expansions of the various components and contents of the device. Another embodiment of temperature compensation utilizes an internal thermometer consisting of, for example, a resistor whose resistance depends upon temperature in a reproducible way, and which is placed in a location isolated from the transducer diaphragm so that its resistance does not depend on pressure variations. Prior to implanting the device, calibration data is collected consisting of the output of the transducer versus pressure as a function of the reading of the internal thermometer. After implantation, the signal from the internal thermometer is used together with the transducer output and the calibration data to determine the temperature compensated pressure reading. In one embodiment, a band gap voltage reference is used to create a current proportional to absolute temperature that is then compared to the temperature-independent voltage reference. Such methods are well-known in the art of CMOS integrated circuit design.

In one embodiment, the devices described herein are configured similarly to a cardiac pacemaker, with a hermetically sealed housing implanted under the patient's skin and a flexible lead with a pressure transducer at its distal end. The housing contains a battery, microprocessor and other electronic components, including a patient signaling device and transcutaneous telemetry means for transmitting programming information into the device and for transmitting physiological data out to an external programmer/interrogator.

One skilled in the art will understand that alternative distributions of the components may be constructed in accordance with several embodiments of the present invention. In one alternative, the pressure sensing circuitry is incorporated into the pressure transducer unit implanted in the heart, reducing the number of conductors needed in the lead to as low as two.

In another embodiment, the signal processing, prescription algorithms, and patient signaling components are located in a device external to the patient's body in communication with the implanted subcutaneous housing via one of various forms of telemetry well known in the art, such as two-way radio frequency telemetry.

In another embodiment, the pressure sensor is fabricated by micro electromechanical systems (MEMS) techniques, as taught by, for example U.S. Pat. No. 6,331,163, herein incorporated by reference.

c. Sensor-Tissue Interaction Issues

In one embodiment, within several weeks after implantation, the entire device is covered with new tissue, including fibrous tissue and endothelium. A covering of endothelium is desirable because it prevents the formation of blood clots that, if formed, could break loose and cause a blocked artery elsewhere in the body, most dangerously in the brain. A covering of fibrous tissue is also a common component of the body's healing response to injury and/or foreign bodies. An excessive growth of fibrous tissue on the left atrial surface of the pressure sensor may be undesirable because it may interfere with accurate transmission of fluid pressure in the left atrium to the pressure sensitive diaphragm. In addition, contraction of fibrous tissue over time may cause progressive changes in the pressure waveform or mean value, which could confound interpretation of the data.

i. Low Compliance Sensor Membrane

In one embodiment, the pressure transducer membrane is designed to have very low compliance. In one embodiment, a low compliance pressure transducer is fabricated using titanium foil as described above. In another embodiment, a low compliance pressure transducer is fabricated from, for example, silicon, using micro electromechanical systems (MEMS) techniques. In yet another embodiment, a coating is provided on the left atrial surface of the pressure sensor.

ii. Coatings, Polishing, and Drug Eluting Surfaces

In one embodiment, a coating inhibits or minimizes the formation of undesirable fibrous tissue, while not preventing the beneficial growth of an endothelial covering. Coatings with these properties are well known in the art of implanting medical devices, particularly intravascular stents, into the blood stream. Surface coating materials include, but are not limited to, paralene, PVP, phosphoryl choline, hydrogels, albumen affinity, and PEO.

In one embodiment, at least some areas of the sensor package and diaphragm are electropolished. Electropolished surfaces are known by those skilled in the art to reduce the formation of thrombosis prior to endothelialization, which leads to a reduced burden of fibrotic tissue upon healing. Metallic intracoronary stents currently approved for clinical use are electropolished for this purpose.

Release of antiproliferative substances including radiation and certain drugs are also known to be effective in stenting. Such drugs include, but are not limited to, Sirolimus and related compounds, Taxol and other paclitaxel derivatives, steroids, other anti-inflammatory agents such as CDA, anti-sense RNA, ribozymes, and other cell cycle inhibitors, endothelial promoting agents including estradiol, antiplatelet agents such as platelet glycoprotein IIb/IIIa inhibitors (ReoPro), anti-thrombin compounds such as heparin, hirudin, hirulog etc, thrombolytics such as tissue plasminogen activator (tPA). These drugs may be released from polymeric surface coating or from chemical linkages to the external metal surface of the device. Alternatively, a plurality of small indentations or holes can be made in the surfaces of the device or its retention anchors that serve as depots for controlled release of the above mentioned antiproliferative substances, as described by Shanley et al. in U.S. Publication No. 2003/0068355, published Apr. 10, 2003, incorporated by reference herein.

d. Pressure Signal Detection

In one embodiment, the implanted portion of the device is comprised of a plurality of up to n physiologic signal detection sensors S described by the set:

$\{S_1, S_2, \ldots S_n\}$.

In one embodiment, $S_1$, the first sensor, detects a parameter that is indicative of left atrial pressure or $S_{iLAP}$, thus $\{S_{iLAP}, S_2, \ldots S_n\}$.

Figure 17:
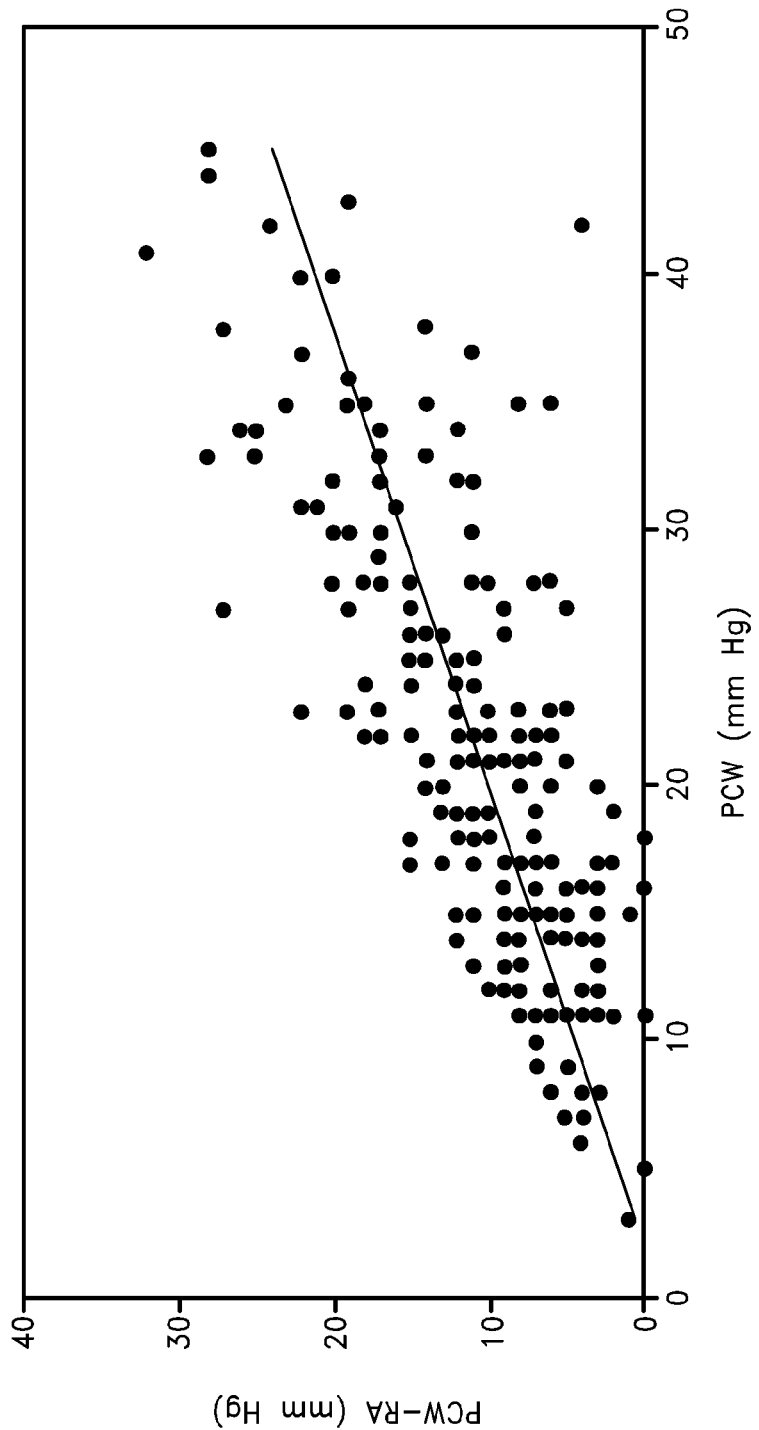
FIG. 17 shows the correlation between the pulmonary capillary wedge pressure (PCW) referenced to atmospheric pressure (abscissa) and the differential pressure between the right atrium and PCW (PCW-RA).

Signals indicative of left atrial pressure can be pressure signals measured at a variety of sites and may be detected by a variety of pressure transducer types. The signals may be obtained from locations in the cardiovascular system or adjacent to the cardiovascular system known to be similar to or highly correlated with direct pressure readings from the left atrium. Such locations for obtaining pressure signals similar to the left atrium are well known to those skilled in the art, such as Cardiologists. Locations for sensing pressure include, but are not limited to, the left atrium and its contiguous structures, the pulmonary veins, the pulmonary capillary wedge or occlusion pressure, the pulmonary artery diastolic pressure, and the left ventricular end diastolic pressures. Other pressures indicative of left atrial pressure include differential pressures such as the difference between the left atria and the right atria, or the difference between the pulmonary capillary wedge and right atrial pressures, as shown by the correlation in FIG. 17. The individual signals comprising the differential signal correlate independently with left atrial pressure.

3. Non-Pressure Sensors a. Left Atrial Dimension

In one embodiment, the system may include one or more additional sensors. In one embodiment, a non-pressure sensor is also provided to generate a signal indicative of pressure in the left atrium. Hemmingsson (U.S. Pat. No. 6,421,565), incorporated by reference herein, describes such an implantable cardiac monitoring devices as an A-mode ultrasound probe which is adapted to be positioned in the right ventricle of a heart, and which emits an ultrasound signal which is reflected from one cardiac segment of the left ventricle of the heart, and the ultrasound probe receives the resulting echo signal. The delay between the emission of the ultrasound signal and the reception of the resulting echo is measured, and from this delay a position of the cardiac segment is determined. In one embodiment, an A-mode ultrasound probe is deployed in the right atrium of a heart so that an ultrasound signal is reflected from one or more cardiac segments of the left atrium, either the atrial septal segment, the lateral wall segment, or both. Increased left atrial pressure is known to cause in increase in the volume of the left atrium by displacing the walls of the left atrium away from each other. Thus, measurement of the positions of one or more left atrial walls provides a signal indicative of left atrial pressure, as described below, that can be used to guide therapy for CHF.

Kojima (U.S. Pat. No. 4,109,644), incorporated by reference herein, describes another implantable ultrasound transducer that could be used in the manner described above to determine left atrial dimension and thus derive a signal indicative of left atrial pressure.

In one embodiment, the sensor comprises one pressure sensor, a pressure sensor package, or module, with pressure sensor and electronics, or a sensor package containing electronics, a pressure sensor, and at least one non-pressure sensor. In one embodiment, the at least one non-pressure sensor provides a signal indicative of: an internal electrocardiogram; a temperature; a physical dimension; an electrical resistance, such as, but not limited to, a thoracic electrical impedance; a respiratory tidal volume; a respiratory rate; lung acoustics; oxygen saturation; oxygen partial pressure, including oxygen partial pressure in the left chamber or the right chamber; or cardiac output. In another embodiment of the invention, the non-pressure sensor measures: left atrial dimension, cross-sectional area, or volume; left ventricular dimension, cross-sectional area or volume; atrial septum position; velocity, or acceleration. In one embodiment, a non-implanted sensor is provided. In one embodiment, the non-implanted sensor includes: an arterial pressure cuff, including an automated arterial pressure cuff; and a weight scale. In one embodiment, two sensors are provided, a first sensor and a second sensor. In one embodiment, the first sensor measure a pressure in the heart and the second sensor measures a non-pressure parameter, including, but not limited to the parameters listed above. In one embodiment, the second sensor is also a pressure sensor. In one embodiment, the first sensor is located internal to the patient and the second sensor is located external to the patient. Located "external", as used herein, shall be given its ordinary meaning and shall also mean located on the patient, in contact with the patient, or located completely independent of the patient.

b. Core Temperature

Other non-pressure physiologic parameters may be used in other embodiments. Casscells III, et al. (U.S. Pat. No. 6,454,707), incorporated by reference herein, describe a method and apparatus for predicting mortality in congestive heart failure patients by monitoring body temperature and determining whether a downward trend in temperature fits any predetermined criteria. The apparatus described by Casscells et al. determines when death is imminent and generates an alarm. In one embodiment of the present invention, the trend in body temperature is used daily to adjust the patient's therapy at an earlier point before any downward trend in temperature becomes critical. In one embodiment, core body temperature is measured at the atrial septum. In another embodiment, core body temperature is measured at the site of a measurement module located anywhere within the heart, heart chambers, great vessels, or other locations within the thorax known in the medical arts to maintain a temperature related in a predictable way to core body temperature.

Regional elevations in temperature are known to those skilled in the art of temperature physiology to occur in the presence of inflammation. Inflammation occurs in the heart in many cardiovascular diseases. Examples of such diseases include myocarditis due to infectious causes such as certain viruses, and other infectious agents, pancarditis associated with acute rheumatic fever, and the inflammation associated with immunological rejection of a transplanted heart. A temperature sensor of sufficient precision residing in proximity to the walls of the heart may detect regional elevations in temperature due to local tissue inflammation. Inflammatory cardiac conditions may also be associated with a rise in left atrial pressure. In one embodiment of the present invention, an implanted monitoring system that measures both local tissue temperature with a precision of approximately 0.1° C. and a parameter indicative of left atrial pressure can be used to diagnose active cardiac inflammation and concomitant cardiac dysfunction.

4. Signals a. Left Atrial Pressure Signals

Figure 18:
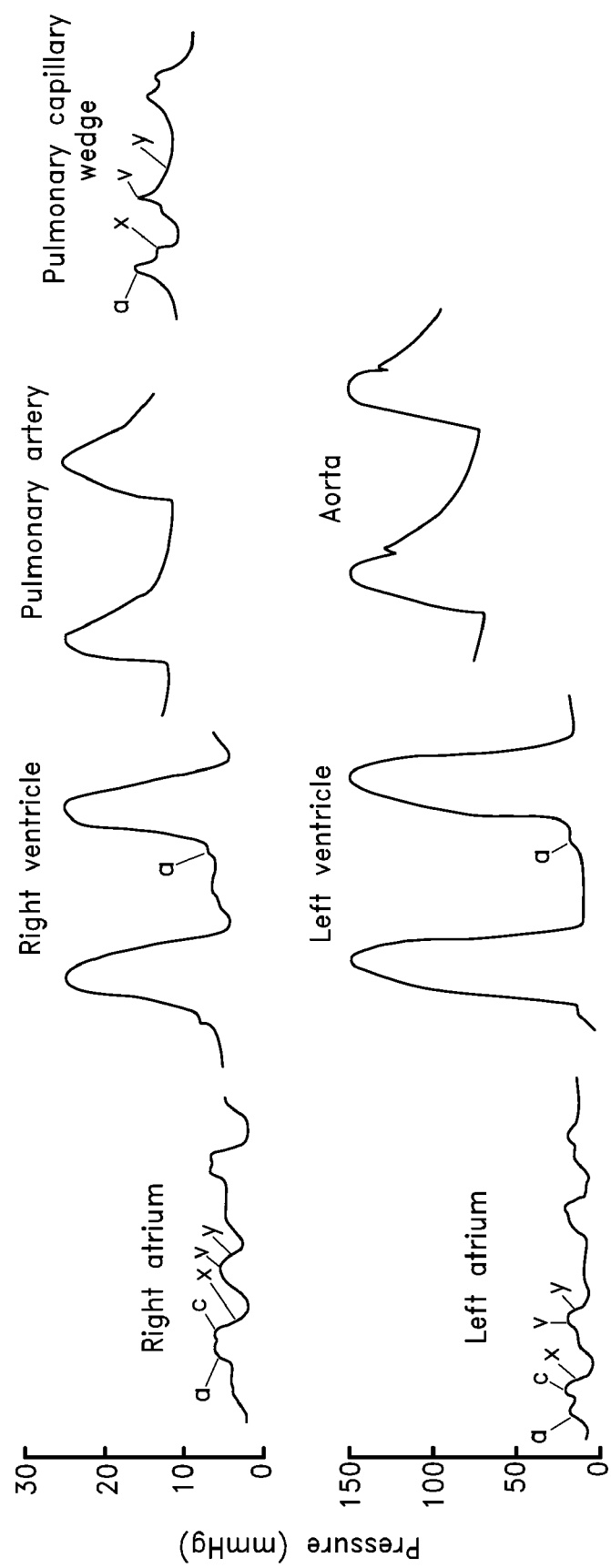
FIG. 18 illustrates typical normal pressure tracings.

In one embodiment, one of the physiological sensors is a pressure transducer that is used to generate a signal indicative of pressure in the left atrial chamber of the patient's heart (the "left atrial pressure," or LAP). In one embodiment, a LAP versus time signal is processed to obtain one or more medically useful parameters. These parameters include, but are not limited to, mean LAP, temporally filtered LAP (including low-pass, high-pass, or band-pass filtering), heart rate, respiratory variations of LAP, respiration rate, and parameters related to specific features of the LAP waveform such as the so-called a, v, and c waves, and the x, x', and y descents. All these parameters are well known to those skilled in the art. Examples of such features in normal cardiac pressure tracings are illustrated in FIG. 18. Examples of parameters derived from specific LAP waveform features include the mechanical A-V delay interval, as defined below (as distinct from the electrical A-V interval derived from the electrocardiogram); the relative peak pressures of the a and v waves, normal values of which are given in the table in FIG. 19; and the pressure values at specific times in the LAP waveform, as are understood by those skilled in the art.

In another embodiment, the parameter is determined based upon at least one wave selected from the group including, but not limited to, one or more of the following: an a wave, a v wave, and a c wave. In yet another embodiment, the parameter is determined based upon a parameter signal selected from the group including, but not limited to one or more of the following: a wave amplitude, a waveform rate of ascent, a waveform rate of descent, timing of a wave feature with respect to a cardiac cycle, timing of a wave feature with respect to another wave feature, time difference between an a wave and a c wave, time difference between an a wave and a v wave, and time difference between a v wave and a c wave. In one embodiment, the parameter is determined based upon at least one descent selected from the group including, but not limited to one or more of the following: an x descent, an x' descent, and a y descent. In another embodiment, the parameter is determined based upon a parameter signal selected from the group including, but not limited to one or more of the following: a descent amplitude, a descent rate of ascent, a descent rate of descent, timing of a descent feature with respect to a cardiac cycle, timing of a descent feature with respect to another wave feature, time difference between an x descent and an x' descent, time difference between an x descent and a y descent, and time difference between an x' descent and a y descent. In another embodiment, the parameter is determined based upon the width of a wave feature, such as the width of the a wave or the v wave. In yet another embodiment, the parameter is determined based upon the difference between the mean pressure and the minimum of the respiratory component of the pressure. It is well known to the skilled artisan that several of these parameters are independent of ambient atmospheric pressure and independent of pressure transducer calibration.

In one embodiment, signals indicative of left atrial pressure are periodic signals that repeat with a period the length of which is equal to the period in between heartbeats. Any portion of the signal or a summary statistic of that periodic signal may be indicative of left atrial pressure and provide diagnostic information about the state of the heart. For example, the a, c, v waves and the x, x', and y descents, described above, correlate with mechanical events such as heart valves closing and opening. Any one of these elements can yield useful information about the heart's condition. Each discrete element represents an individual signal indicative of left atrial pressure. A summary statistic such as the arithmetic mean left atrial pressure also represents a signal indicative of left atrial pressure. One skilled in the art will appreciate that there are additional discrete elements and summary statistics that are valuable indicators of left atrial pressure. Advantageously these components of left atrial pressure are relative to each other and therefore do not have to be compensated for atmospheric pressure and are not subject to offset drift inherent in most pressure transducers.

In one embodiment, the relative heights and/or shapes of the left atrial a, v, and v waves are monitored to detect and diagnose changes in severity of cardiovascular disease. This information permits differentiation between worsening symptoms of CHF due to volume overload versus impaired left ventricular pump function (such as decrease left ventricular compliance, or acute mitral regurgitation), allowing medical therapy to be appropriately targeted. For example, pure volume overload is usually manifest with a progressive elevation of the mean left atrial pressure and generally responds to fluid removal by taking a diuretic medication, natriuretic peptide, or and invasive technique known as ultrafiltration of the blood. Decreased left ventricular compliance is the diagnosis when the a wave increases without shortening of the atrioventricular (AV) delay or in the presence of mitral stenosis. Acutely decreased compliance may be indicative of left ventricular (LV) ischemia, while chronically decreased compliance may be indicative of LV wall thickening know as hypertrophy. The former may respond to nitrates or coronary artery interventions, while the latter may respond to beta or calcium antagonist drugs, or chemical septal ablation. Increases in the v wave amplitude and merging with the c wave to produce a cv wave is usually indicative of acute mitral valve regurgitation. This may be due to a sudden mechanical failure of the valve or its supporting apparatus, or it may be due to acute ischemia of the supporting papillary muscles as part of an acute coronary artery syndrome. Sudden mechanical failure requires surgical repair or replacement, while ischemia may require anti-ischemic medications such as nitroglycerin or coronary artery interventions such as angioplasty or bypass surgery. FIGS. 6A-6C list these and other parameters derivable from cardiac pressure tracings that may be interpreted to facilitate diagnosis of cardiovascular disease states.

In another embodiment, atrial fibrillation and atrial flutter are detected by analysis of the LAP waveform. In another embodiment, spectral analysis of the LAP versus time signal is performed.

i. Measurement of Absolute Pressure

In one embodiment, an apparatus for measuring absolute pressure at a location within the body is provided. In one embodiment, the apparatus includes a transducer/communications module for making measurements, and communicating the measurement to another device, as described above. The transducer/communications module can include transducers or sensors suitable for measuring pressure, as are well known to those of skill in the art, temperature, or other physiological parameters. In one embodiment, the transducer/communications module measures an absolute pressure. In another embodiment, the transducer/communications module measures the pressure difference between a location in the body and a reference pressure within the implanted transducer/communications module.

ii. Measurement of Relative Pressure (Gauge Pressure)

In one embodiment, the system contains the necessary components to obtain a signal indicative of pressure relative to atmospheric pressure. An implanted apparatus for measuring absolute pressure at a location within the body is provided as above, which further communicates this information, as either an analog or digital signal, to an external signal analyzer/communications device. The external signal analyzer/communications device further contains a second pressure transducer configured to measure the atmospheric (barometric) pressure. The analyzer/communications device performs a calculation using the absolute pressure from the implanted module and the atmospheric pressure to obtain the internal pressure relative to atmospheric pressure, that is, difference between the absolute pressure at the location within the body and the absolute barometric pressure outside the body. This pressure, also known as the gauge pressure, is known to those skilled in the art to be the most physiologically relevant pressure measure.

In one embodiment, gauge pressure measurements are performed only when the implanted apparatus is queried by the external analyzer/communications device, advantageously assuring that the atmospheric pressure at the time and patient's location is available and correctly matched with the absolute internal pressure reading. It will be clear to those skilled in the art that unmatched internal and barometric pressure readings would render the gauge pressure measurement inaccurate or useless. In this embodiment, internal absolute measurements are made only when the external analyzer/communications device is physically present. In one embodiment, this is accomplished by having the external device supply operating power to the implant module to make the measurement. In another embodiment, such as when the implanted module contains an internal power source such as a battery, this is accomplished by requiring a proximity RF link to be present between the external and implantable modules, either immediately before and/or after and/or during the measurement.

iii. Measurement of Differential Pressure

In another embodiment, an apparatus for measuring differential pressure is provided. In one embodiment, the apparatus includes a transducer/communications module for making measurements, and communicating the measurement to another device, such as a processor, or patient advisory module. The transducer/communications module can include transducers or sensors (these terms are used synonymously herein), suitable for measuring pressure as are well known to those of skill in the art, temperature, or other physiological parameters. In one embodiment, the transducer/communications module measures a differential pressure that includes the pressure difference between two locations inside of the body. For example, the transducer/communications module measures the difference between the fluid pressure of the blood in an artery, and the intrathoracic pressure, detected through the artery's wall. In another example, the transducer/communications module measures the difference between the fluid pressure in the left atrium and the right atrium of the heart, detected by a module In one embodiment, the transducer/communications module includes a plurality of pressure sensing membranes, each with an outer surface and an inner surface. In one embodiment, there are two pressure sensing membranes in the module so that when the device is implanted, for example in the atrial septum, one pressure sensing membrane's outer surface is in contact with the blood of the left atrium and the other pressure sensing membrane's surface is in contact with the blood of the right atrium. The inner surfaces of both pressure-sensing membranes are exposed to the same internal space within the device. Each membrane has an associated strain gauge, each strain gauge creating a signal indicative of the pressure difference between the outer and the inner surfaces of the respective membrane. Since the two membranes share the internal space, the pressures on their inner surfaces are equal. Thus, the differential pressure, determined by subtracting the pressure of one transducer from the other, is proportional to the left atrial pressure in reference to the right atrial pressure. The baseline-offset calibration of the differential transducer can be determined by having the patient perform a Valsalva maneuver, which is known by those skilled in physiology to equalize the pressure within the chambers of the heart.

In one embodiment, the module contains the necessary components to obtain from the transducers a signal indicative of differential pressure, and to communicate this information either as an analog or digital signal, indicative of the severity of a condition, such as congestive heart failure, to an external signal analyzer/communications device. The implanted module may contain an internal power source such as a battery, or it can be powered transcutaneously by induction of radio frequency current in an implanted wire coil connected to the module to charge an internal power storage device such as a capacitor.

b. Other Measures Indicative of Left Atrial Pressure

In one embodiment, pulmonary artery diastolic pressure (PADP) is estimated from an analysis of the right ventricular pressure waveform, as taught by Carney in U.S. Pat. No. 5,368,040, incorporated by reference in its entirety herein. In one embodiment, the pressure module is placed in the right ventricle. In other embodiments, the pressure module is placed in the right atrium or a pulmonary artery. It is known to those skilled in the art that under many circumstances, PADP approximates the pulmonary capillary wedge pressure (PCWP), which is a clinically useful measure of mean left atrial pressure. In this case, the right ventricular pressure waveform provides a signal indicative of left atrial pressure. Right ventricular end diastolic pressure, right atrial pressure, and central venous pressure have been shown to linearly correlate with LAP or PCWP but do so with a slope less than 1.0, that is, they generally underestimate LAP/PCWP. An inverse linear transformation of any of these right-sided cardiac pressures will therefore yield a pressure that is indicative of LAP. Similarly, the arterial blood pressure response to forced exhalation against a blocked airway outflow, known as the Valsalva maneuver, is linearly correlated with PCWP (as described by Finkelstein in U.S. Pat. No. 4,899,758, incorporated by reference in its entirety herein) and is therefore also indicative of LAP.

In several embodiments, non-pressure physiologic signals are used to indicate left atrial pressure. In most cases, these non-pressure physiologic signals correlate to left atrial pressure through straightforward mathematical relationships. For example, for periodic signals of left atrial pressure and volume, a periodic pressure-volume relationship may be used. One well-known example of a pressure-volume relationship occurs during atrial diastole, when the ratio AV/AP, known as the diastolic compliance, is generally stable. Thus, a given left atrial volume, cross-sectional area or any dimension indicative of that volume is also a signal indicative of left atrial pressure, and a sensor capable of measuring a left atrial dimension or area may be used to determine left atrial pressure. Thus, in one embodiment of the invention, one or more physiological sensors are provided to directly or indirectly sense one or more of the following physiological parameters: left atrial dimension, cross-sectional area, and/or volume; left ventricular dimension, cross-sectional area or volume; atrial septum position; heart chamber wall velocity, and/or acceleration.

Examples of sensors capable of measuring such dimensions or areas include, but are not limited to an intracardiac ultrasonic imaging system operating in M-mode, 2-dimensional, or 3-dimensional modes, as well as paired ultrasonic crystals. It is well known in the art that heart chamber dimensions or cross-sectional areas may be measured and volumes estimated by the use of ultrasound, as described, for example, by Kojima (U.S. Pat. No. 4,109,644) and by Hemmingsson (U.S. Pat. No. 6,421,565), both incorporated by reference herein. Such ultrasonic systems may have additional diagnostic value in that Doppler analysis can detect changes in atrial flow patterns due, for example, to mitral regurgitation.

It is also known in the art that electrical impedance changes may be indicative of changes in heart chamber dimensions. An example of a physiological sensor suitable for use in one embodiment of the current invention is described by Alt (U.S. Pat. No. 5,003,976), incorporated by reference herein. Alt describes how analyzing the impedance between two intracardiac electrodes may be used to determine changes in cardiac chamber volumes, which under certain circumstances as described above are indicative of changes in chamber pressures, and thus may be used to detect worsening heart failure and guide therapy according to the present invention.

In accordance with the above description, an embodiment of the present invention comprises a physiologic signal detection sensors set which may be alternately described as:
- $\{S_{iLAV}, S_2, \ldots S_n\}$, where $S_{iLAV}$ is a sensor indicative of left atrial volume;
- $\{S_{iLAA}, S_2, \ldots S_n\}$, where $S_{iLAA}$ is a sensor indicative of left atrial cross-sectional area; or
- $\{S_{iLAD}, S_2, \ldots S_n\}$, where $S_{iLAD}$ is a sensor indicative of left atrial dimension; where the first sensor in all sets detects a signal that is indicative of left atrial pressure. Additional sensors in the implanted portion of the device may include detectors for any other physiologic signal. For example:
- $\{S_{iLAP}, S_{iLAD}, S_{iECG}, S_{iCT}, S_{iO2}, \ldots, S_n\}$, where sensors denoted by subscripts iECG, iCT, iO$_2$ are detectors or signals indicative of the electrogram, core temperature, and oxygen saturation, respectively. One skilled in the art will appreciate that there are numerous sensor configurations and sensor types that may be used in accordance with various embodiment of the present invention.

In one embodiment of the invention, multiple physiologic sensors are contained in a single package. In another embodiment, a plurality of packages is spatially distributed. Some of the packaging may place a particular sensor outside of the body. For example, in one embodiment, signal detection sensor packages P$_1$, P$_2$, and P$_3$ may be located internally or external to the body and consist of the following sets:
- P$_1$={S$_{iLAP}$, S$_{iCT}$}, located in the intra-atrial septum;
- P$_2$={S$_{iECG}$}, located in the superior vena cava; and
- P$_3$={S$_{iABP}$}, where iABP is a signal indicative of arterial blood pressure.

One skilled in the art will appreciate that several embodiments of the current invention include the detection of various signals indicative of left atrial pressure. Such signals include, but are not limited to: a, c, v, x, x', and y of LAP, mean LAP, the respiratory portion of LAP, the total cardiac portion of LAP, and filtered LAP between frequencies. In several embodiments, non-LAP signals are used. These non-LAP signals include, but are not limited to, the detection of left atrial dimension, left atrial cross-sectional area, left atrial volume, left ventricular volume, atrial fibrillation, atrial flutter, respiratory tidal volume, respiratory rate, weight change, blood pressure or change in blood pressure, core temperature, oxygen saturation, oxygen partial pressure, cardiac output, LA to RA temperature differential, lung acoustic signal, and EEG.

One skilled in the art will understand that numerous configurations of sensors and sensor packaging and locations may be used in accordance with various embodiments of the current invention.

c. Other Blood Pressure Signals

In another embodiment, one or more physiological sensors measure central venous blood pressure.

In one embodiment of the invention, one or more of the physiological sensors measure peripheral arterial blood pressure. Analysis of peripheral artery blood pressure to obtain a parameter indicative of congestive heart failure status has been described, by Finkelstein (U.S. Pat. No. 4,899,758), incorporated by reference herein. In one such embodiment, the peripheral artery blood pressure sensor may be a cuff sphygmomanometer, and the patient's systolic and diastolic blood pressures are entered into the signal processing apparatus by the user. In a further embodiment, the blood pressures may be sent by direct signal communication to the signal processor.

Other arrangements of pressure transducers will be apparent to one skilled in the art. The transducer/communications module may contain other types of sensing apparatus. In one embodiment, in addition to the implanted pressure sensor, electrocardiographic and temperature sensors are provided.

d. Other Physiological Parameters

In one embodiment, the internal electrocardiogram (known as the IEGM) is sensed at one or more locations. In a further embodiment, the IEGM is processed to obtain one or more medically useful parameters. These parameters include, but are not limited to, heart rate, the timing of atrial and ventricular depolarization, the time interval between atrial and ventricular depolarization (known in the art as the A-V interval), the duration of ventricular depolarization (known in the art as the Q-T interval), ST segment changes to detect acute ischemia, and spectral analysis to detect t-wave alternans (a known harbinger of life threatening arrhythmias), all of which are familiar to those skilled in the art.

In one embodiment, one of the physiological sensors is a thermometer measuring core body temperature, as described above.

In one embodiment of the present invention, Doppler ultrasound provides a signal that is proportional to the relative velocity of the ultrasound probe and a structure, such as a heart chamber wall, producing an ultrasound echo. A velocity signal can be differentiated to obtain acceleration, as is well known to those skilled in the art. Conversely, implantable accelerometers are sensors known in the art that provide a signal that is proportional to the acceleration of the implanted sensor. An acceleration signal can be integrated to obtain a velocity plus an arbitrary constant velocity. Because it is known that the average velocity of any structure in the body, relative to the body, is necessarily zero, the arbitrary constant velocity is determined, and the relative velocity signal can be uniquely recovered from the acceleration signal. Thus, velocity and acceleration measurements of structures in the heart are essentially equivalent, the one being derivable from the other. As is well known in the art, a velocity signal may be integrated to obtain a position or displacement signal plus an arbitrary constant displacement. Thus, the motion and displacement of a structure in the heart, or the range of variation of the dimension of a chamber of the heart, may be recovered from the velocity or acceleration signal of the structure or of the chamber walls, respectively.

Vallana and Garberoclio (U.S. Pat. No. 5,454,838, incorporated by reference herein) teach that components of the velocity or acceleration signal are indicative of aspects of cardiac activity, such as opening of the mitral valve, closure of the mitral valve, opening of the aortic valve, closure of the aortic valve, an amount of ventricular ejection, rapid ventricular filling, delayed ventricular filling during atrial systole, and cardiac flow rate. As these aspects of cardiac activity may be indicative of changes in the patient's condition, and may be responsive to changes in the patient's prescription, they are within the scope of parameters contemplated to be used with embodiments of the present invention.

In another embodiment of the present invention, a physiological sensor measures respiratory tidal volume, respiratory rate, lung acoustic signal, and/or thoracic electrical impedance.

In one embodiment of the invention, one of the physiological sensors measures total body weight. In one embodiment, the sensor is a scale. In another embodiment, the patient's weight is entered into the signal processing apparatus by the user. In another embodiment, the weight sensor is a scale that communicates a signal indicative of the patient's weight to the signal processing apparatus without requiring a user to enter the value. Lloyd et al. (U.S. Pat. No. 6,080,106), incorporated by reference herein, describe a digital scale suitable for use in one embodiment of this invention.

In yet another embodiment of the invention, one or more sensors measure: oxygen saturation; oxygen partial pressure in the left, right, both left and right-sided cardiac chambers, or adjacent great blood vessels; or cardiac output.

5. Signal Processing Apparatus

In one embodiment, the signal processing apparatus of the present invention receives signals from the one or more sensors, and processes them together with stored parameters relevant to the patient's medical management. In one embodiment, the result of this processing is a signal indicative of the appropriate therapeutic treatment or course of action the patient or an immediate personal care giver can take to manage or correct, as much as possible, the patient's condition. In one embodiment, the signal processing apparatus is located outside the patient's body. In one embodiment, signals from one or more permanently implanted physiological sensors are received by the external signal processing apparatus by wireless telemetry. In one embodiment, certain signal processing is performed within the one or more individual sensor devices prior to the signal being sent to the signal processing apparatus. In one embodiment one signal received by the signal processing apparatus is the LAP versus time waveform sampled at over 20 Hz for a duration of several respiratory cycles (for example, but not limited to, 10 to 30 seconds). In one embodiment, the signal processing apparatus also receives a signal from a temperature sensor located at substantially the same position as the LAP sensor and uses this temperature to apply a temperature compensation correction to the LAP signal using calibration data stored in the signal processing apparatus. In one embodiment, the processor also receives ambient temperature and atmospheric pressure, performs temperature compensation, and subtracts the atmospheric pressure from the LAP to obtain the relative or "gauge" LAP. In one embodiment, the signal processing apparatus then computes the mean LAP from the relative LAP versus time waveform. In one embodiment the signal processing apparatus then compares the mean LAP with patient-specific treatment ranges for mean LAP that have been programmed into the signal processing apparatus by the patient's physician. In one embodiment, for each patient-specific programmed treatment range the patient's physician stores in the signal processing apparatus an indication of the appropriate therapeutic treatment or action the patient should take to manage or correct, as much as possible, the patient's condition. A signal indicative of the physician-prescribed therapeutic action corresponding to the patient-specific range into which the measured physiologic parameter falls is then sent to a patient signaling device.

In another embodiment of the invention, the signal processing apparatus is essentially permanently implanted within the body, in either the same or a different location as the one or more physiological sensors. In one embodiment, the sensors may be in signal communication with the signal processing apparatus by means of one or more connective leads that may carry electrical, optical, hydraulic, ultrasonic or other forms of signaling energy. The conductive lead(s) may vary in length up to and exceeding about 100 cm. In another embodiment, the sensors may be in wireless communication with the signal processing apparatus. The lead can be coupled to an antenna for wireless transmission or to additional implanted signal processing or storage apparatus.

6. Interpretation of Signals

In one embodiment of the present invention, patients are diagnosed based upon the interpretation of signals generated by one or more sensors. For example, a signal indicating low mean right atrial pressure may suggest hypovolemia or improper zeroing of the transducer. FIGS. 6A-6C provide other examples by which signals may be interpreted to facilitate diagnosis, prevention and treatment of cardiovascular disease according to various embodiments of the present invention.

One skilled in the art will understand that other interpretations may be used in accordance with various embodiments of the current invention. Further, one skilled in the art will understand that normal ranges of the various physiologic parameters measured in several embodiments of the current invention can be found in cardiology textbooks or reference books. Additionally, it may be useful to compare patient parameters within the same patient by ascertaining initial baseline values and comparing these baseline numbers to values generated at some later desired time. This may be particularly useful in determining progression of disease and response to treatment.

In several embodiments, sensors in addition to the left atrial pressure sensor are used. Additional sensors provide further refined diagnostic modes capable of distinguishing between different potential causes of worsening cardiovascular illness, and then of signaling an appropriate therapeutic treatment depending upon the particular cause for any particular occurrence.

For example, increased left atrial pressure is commonly caused by improper administration of medication, patient non-compliance, or dietary indiscretion, e.g., salt binging. These causes will be generally well-handled by changes in the patient's drug regimen like those described above. However, there are other causes of increased left atrial pressure that are less common, but by no means rare, and which require different therapies for adequate treatment. For example, one such potential cause is cardiac arrhythmia, and especially atrial fibrillation with a rapid ventricular response. Other arrhythmias may contribute as well to worsening heart failure. A system including an ECG electrode in addition to the left atrial pressure sensor would allow the system to diagnose arrhythmias and determine whether the arrhythmia preceded or came after the increase in left atrial pressure. Depending on the unit's programming, as specified by the patient's physician, specific therapies could be signaled tailored to treat the specific causes and conditions associated with particular adverse events.

In another example of the usefulness of additional physiological signals is to distinguish between pulmonary congestion caused by worsening CHF and that caused by a respiratory infection. In a further embodiment, core body temperature is used together with left atrial pressure to allow the early detection of fever associated with infection. It is well known that core body temperature often becomes elevated hours to days prior to symptomatic fever associated with infection-related pulmonary congestion. In one embodiment, increased core temperature in the presence of stable left atrial pressure would trigger a message to the patient not to increase the dosage of oral diuretic despite symptoms of increasing congestion, and to consult with the physician.

7. Patient Signaling Devices

In one embodiment, the signal processing apparatus and the patient signaling device are permanently implanted, and the patient is signaled using at least two distinguishable stimuli, such as distinguishable sequences of vibrations, acoustic signals, or mild electrical shocks, perceptible by the patient.

According to one embodiment of the invention, one or more physiological sensors is implanted within the body, the signal processing apparatus and the patient signaling device are located outside the body, and the signal indicative of a physiological parameter is communicated by wireless telemetry through the patient's skin. In one embodiment, an external telemetry system is combined with the signal processing apparatus and the patient signaling device. In one embodiment, a hand-held personal data assistant (PDA) such as the PALM PILOT™ (Palm Computing, Inc.) and/or HANDSPRING VISOR® (Handspring, Inc.) is used for the signal processing and patient signaling apparatus. In one embodiment, patient signaling is accomplished using sound, text, and/or images.

B. Combination with Other Devices

It will be clear to those skilled in the art that many patients who would benefit from several embodiments of the present invention would also benefit from an implantable CRM apparatus such as a cardiac pacemaker. In one embodiment, the present invention is combined with an implantable CRM apparatus generator. In one embodiment, the flexible lead on which the physiological sensor is disposed also serves as the sensing or pacing lead of an implantable rhythm management apparatus. In this case, conductors within the lead provide for EKG sensing, powering of the physiological sensor, data communication for the physiological sensor, and pacing stimulus.

In another embodiment, the present invention is functionally integrated with another implantable device, such as, for example, a pacemaker or a defibrillator. In one embodiment of this invention, one or more parameters indicative of a physiological condition produced by the present invention are used by the integrated device to control its therapeutic function, as described below.

In yet another embodiment, the sensor and lead of the Stand-Alone device may be connected without modification either to a subcutaneous coil antenna as described above, or to a combination CRM generator housing containing a battery power supply and other components as described below. In one embodiment, the device may be upgraded after permanent implantation by replacing the coil antenna assembly with an implantable CRM apparatus.

1. Combination with Cardiac Rhythm Management (CRM) Apparatus

Many patients who might benefit from several embodiments of the present invention described above would also be likely to benefit from an implantable CRM apparatus for therapy of brady- or tachy-arrhythmia in the setting of CHF. Examples of such CRM devices include single or multichamber cardiac pacemakers; automatic implanted cardiac defibrillators; combined pacemaker/defibrillators; biventricular pacemakers; and three-chamber pacemakers, all well known to those skilled in the art. In these patients, it would be beneficial to combine several embodiments of the present invention with such a CRM device. This combination would have the advantage that certain components of both systems could be shared, reducing cost, simplifying implantation, minimizing the number of implanted devices or leads. As described in detail below, in some embodiments a combination with a CRM apparatus includes adding pacing and/or defibrillation to the therapeutic actions included in the dynamic prescription of several embodiments of the present invention.

In one embodiment, a flexible lead serves also as an atrial septal pacing lead. It will be recognized by those skilled in the art, such as cardiologists, that pacing the atrial septum provides certain advantages for patients with congestive heart failure. These advantages may include more direct control over left atrial/left ventricular synchrony, inhibition of atrial fibrillation, and it requires one less lead to be inserted in patients that are in need of a rhythm management device that includes atrial pacing and a hemodynamic monitoring/therapy device, etc.

Figure 20:
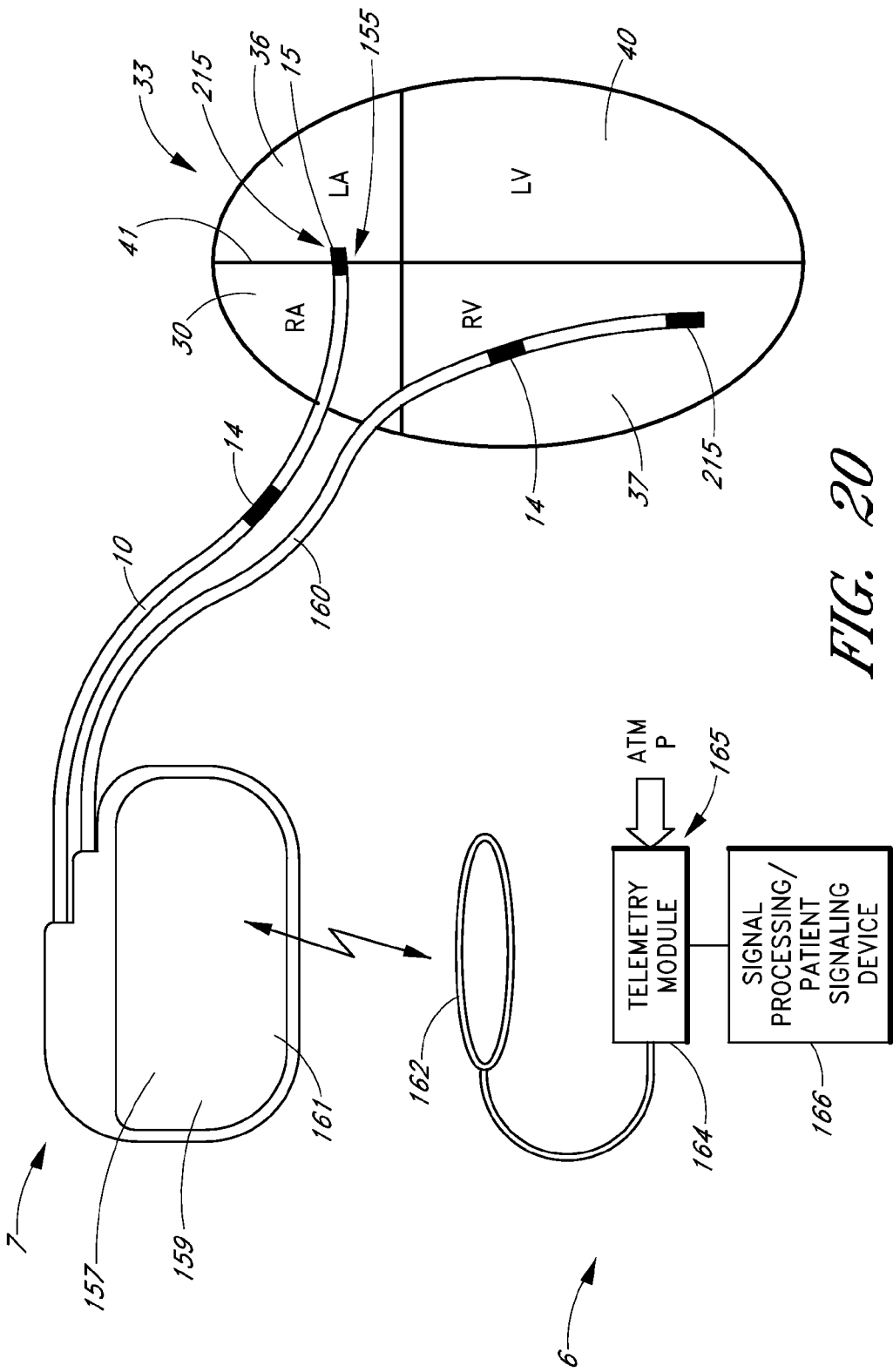
FIG. 20 shows a combination of one embodiment of the present invention with an implantable cardiac pacemaker, in which the sensor is a left atrial pressure sensor implanted in the intra-atrial septum, and the sensor lead also serves as the atrial lead of the pacemaker. A separate ventricular pacing lead is also provided.

It will also be known to those skilled in the art that pacing multichamber sites in appropriate sequence in addition to the atria, such as the right ventricle and the lateral wall of the left ventricle in combination, or the lateral wall of the left ventricle alone, has specific advantages for some patients with congestive heart failure due to enhanced synchrony of left ventriclar contraction. FIG. 20 illustrates one embodiment of the present invention in which a sensor package 15 at the end of flexible lead 10 is implanted across the atrial septum 41 of a patient's heart 33. The sensor package 15 measures the left atrial pressure and also serves as the atrial septal pacing electrode 215 of a CRM device, which may be located within an implanted housing 7. A second flexible lead 160 is placed via the right atrium 30 into the right ventricle 37. Each lead is shown with an indifferent electrode 14 proximal to its respective distal electrode 215, although those skilled in the art will recognize one of these could be eliminated. The housing 7 contains the CRM device (not shown), which in one embodiment includes a battery and electrical circuitry for pacing the heart 33, and components of a physiological monitoring system. It will be clear to the skilled artisan that a variety of configurations may be used to combine the CRM and physiological monitoring functions of such a combined device, examples of which are described below.

Referring to FIG. 20, in one embodiment the housing 7 includes a coil antenna 161 for communicating the one or more physiological signals from sensor package 15 to an external patient advisory module 6. In one embodiment, the external patient advisory module 6 includes a telemetry module 164 and antenna 162, a barometer 165 for measuring atmospheric pressure, and a signal processing/patient signaling device 166, such as described above with reference to FIG. 5.

In one embodiment, components are housed within the implantable housing of an implantable CRM apparatus, including but not limited to the power source, signal processing apparatus, telemetry apparatus, or patient alarm. Alternatively, in another embodiment, components of a CRM may be shared with other implantable devices, such as the apparatus for treating congestive heart failure described in greater detail above. Components that may be shared include, but are not limited to, a power source, telemetry module, data memory, etc. For example, the flexible physiological sensing lead of any of the apparatus for treating congestive heart failure described above may be use as a pacing and/or sensing lead of a CRM. In other embodiments, separate pacemaker and sensing leads are provided.

In one embodiment of the present invention, components of the apparatus for treating congestive heart failure are shared with the components of a CRM apparatus in such a way that, while sharing components, the two systems function essentially independently. In one embodiment, the implantable CRM apparatus generator has a housing that also serves as the housing for at least some components of the apparatus described in greater detail above. In a further embodiment, the power supply of the CRM apparatus, typically comprising a long lifetime battery and power management circuitry, also supplies power for one or more components of the apparatus for treating congestive heart failure. In yet another embodiment, the flexible lead or leads connecting the sensors of the apparatus of FIG. 1, FIG. 2, and FIG. 4, to a shared housing/generator are also coupled to sensing and/or pacing electrodes of the CRM apparatus.

In one embodiment, one or more separate leads coupled to the physiological sensor described above, such as a pressure transducer, is also coupled to the CRM apparatus. In this embodiment, the CRM apparatus shares its generator housing with components of the implantable heart monitor apparatus described above, but the CRM apparatus leads are separate from the physiological sensor leads. In another embodiment, the pressure sensing lead may be combined with a pacing lead, as described for example by Pohndorf (U.S. Pat. No. 4,967,755) or Lubin (U.S. Pat. No. 5,324,326), herein incorporated by reference.

a. Integration of Sensor and Pacing Lead

In one embodiment of the present invention, a system and method is provided for combining a CRM apparatus, implantable heart monitor, and patient communication device. The system provides the following functionality via a single pacing/sensing lead which in one embodiment includes only two conductors: (1) provides power to the physiological measurement module(s); (2) provides signaling for atrial pacing and sensing; (3) provides for programming of the physiological sensor package(s); and (4) provides measurement data from the physiological sensor package(s) to the monitor/defibrillator housing for immediate or delayed use by the patient, doctor or other caregiver via the patient signaling module. Additional pacing and/or sensing leads may be added.

In one embodiment, an external telemetry device (such as described above with reference to FIG. 4 and FIG. 5) is used to communicate with and query a CRM/heart monitor system. The external device analyzes the data with respect to the doctor's prescription, and then indicates to the patient which and what dose of medications or other actions he or she should take. In one embodiment, the data is also provided to the logic within the CRM system for improving pacing or defibrillation therapy.

Figure 21:
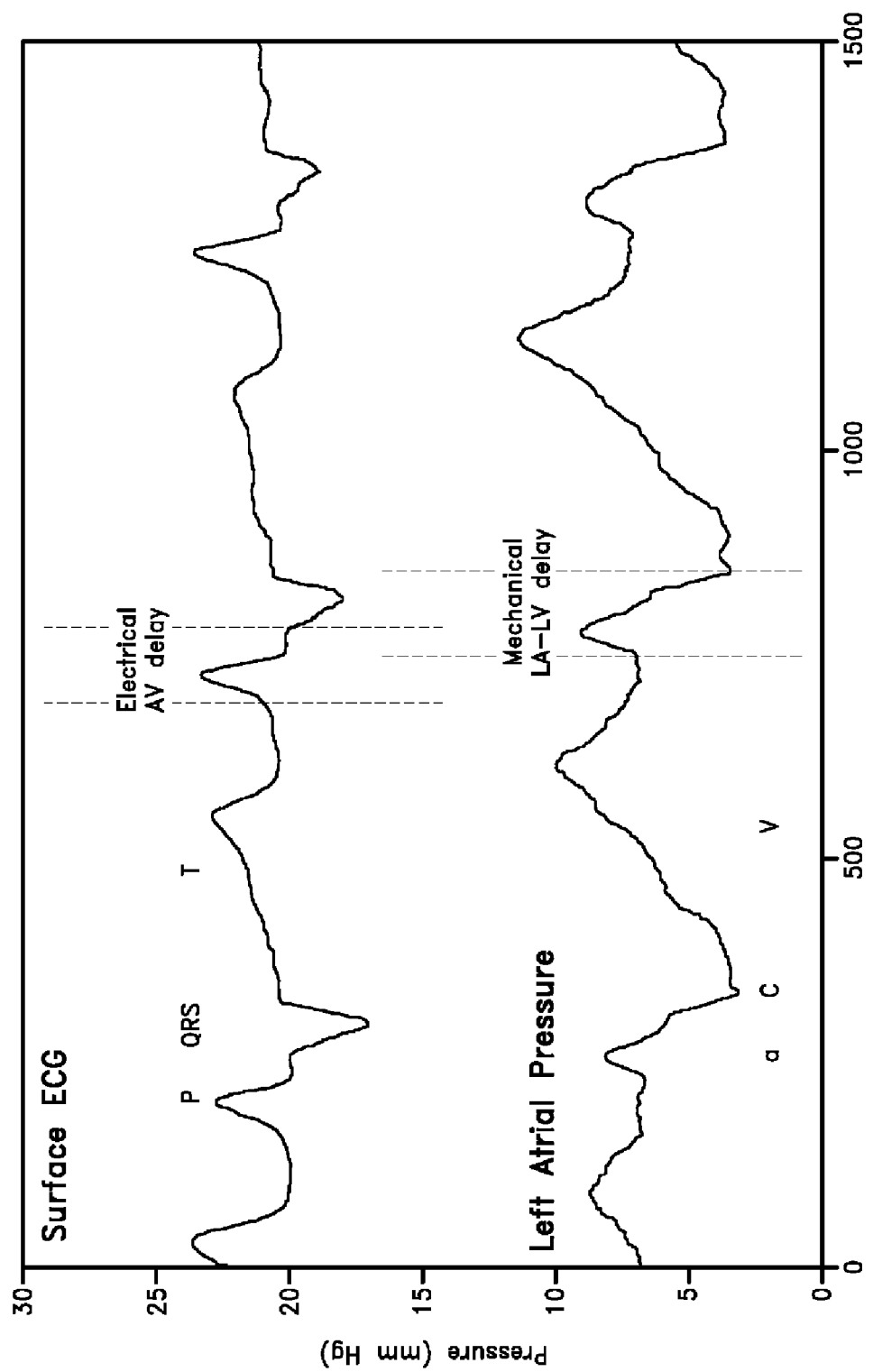
FIG. 21 shows the relationships between the electrocardiogram and the left atrial pressure tracing.

For example, in one embodiment, the pressure waveform from the left atrial chamber contains information pertinent to adjusting atrioventricular dual chamber or atrio-biventricular triple chamber pacing for optimizing the synchrony between left atrial and left ventricular mechanical contraction. FIG. 21 shows why it is difficult for pacemakers to automatically control the optimal delay between the left atrium (LA) and left ventricle (LV). The electrical atrioventricular delay (AV delay), which a conventional CRM system can sense, may be substantially different that the mechanical AV delay, which the conventional CRM cannot sense, but which is the relevant interval for optimizing cardiac function. The relationship between the electrical AV delay and the mechanical AV delay is dependent on several, difficult to measure variables, including intra-atrial conduction time, sub-AV node/HIS bundle conduction delays, volume/pressure preloading of the atria and ventricles and ventricular contractility, among other things, as is known to cardiologists and electrophysiologists. The mechanical AV delay is clinically important because if the delay is too long, usually greater than about 250 msec, then atrial contraction does not have an effective pressure boosting/volume priming effect on the left ventricle, thus adversely effecting LV contractility, stroke volume, and cardiac output. If the mechanical AV delay is too short, usually less than about 120 msec, atrial contraction occurs against a closed or closing mitral valve, again adversely affecting atrial emptying, and pressure/volume boosting of the LV pump. Both a too long and a too short LA-LV mechanical delay can potentially worsen heart failure by further raising the LA pressure. These conditions are potentially extractable from an LA pressure tracing in the following ways. Too long an LA-LV mechanical delay will manifest as an increase in the amplitude of the LA pressure "v" wave relative to the "a" wave and an exaggeration of the "x" descent. Too short an LA-LV mechanical delay will manifest as an increase in the LA pressure "a" wave relative to the "v" wave and a reduction in the "x" descent. As illustrated in FIG. 21, the actual mechanical LA-LV delay can be directly measured from the LA pressure waveform as the interval from the onset of LA contraction represent by the LA pressure "a" wave, to mitral valve closure represented by the "c" wave. In one embodiment, the measured mechanical AV delay is used to adjust the electrical AV delay by a feedback control system or an algorithm to achieve a preset ideal AV delay, or alternatively by minimizing LA mean pressure. In another embodiment, the frequency response of the left atrial pressure transducer is sufficiently high to detect the acoustic energy or sound of mitral valve closure or of other cardiovascular acoustic energy generating phenomena. These frequencies are well known to those skilled in the art of phonocardiography. In one embodiment, this allows for even more precise timing of the AV mechanical interval or other mechanical intervals that are useful in regulating pacing and/or other therapeutic measures. In another embodiment, a sensor is provided that includes an intracardiac microphone. For example, the sensor is operated with a sampling rate sufficient to capture the desired acoustic waveforms, including but not limited to about 200 Hz, or about 2000 Hz, etc., to capture acoustic waveforms with relevant frequency components below about 100 Hz or about 1 kHz, respectively. It is well known in the art of digital signal processing to sample at a rate at least twice the highest frequency component of interest within the signal. It is further well known to limit aliasing artifacts by low pass filtering a signal to a maximum frequency of half the sampling rate prior to sampling.

There are other features in the LA pressure waveform that can be used to modify pacing parameters such as backup atrial pacing rate and rate-responsive algorithms that will be apparent to one skilled in the art. For example, to increase cardiac output, and potentially lower the left atrial pressure, the resting heart rate may be raised from the typical backup atrial pacing rate in the range of 60 to 70 beats per minute when the patient is in compensated heart failure (mean LAP <16-20 mm Hg), to a faster backup atrial rate when the patient is decompensated with an elevation of LAP. Similarly, the mean left atrial pressure can be used to modify rate response algorithms, normally based on activity, minute ventilation, or other physiologic parameters, so that the rate response is also specific to the state of congestive heart failure.

In another embodiment, the signal processor, dynamic prescription, and patient signaling device are completely contained within the implanted CRM apparatus housing. Several methods of patient signaling from an implanted device are well known in the art, including the use of mild electrical stimulation (e.g., U.S. Pat. Nos. 4,140,131, 4,619,653 and 5,076,272), or audible sounds (e.g., U.S. Pat. Nos. 4,345,603 and 4,488,555), including intelligible speech (e.g., U.S. Pat. No. 6,247,474), all herein incorporated by reference.

In another embodiment, the measurement of pressure or other physiological parameters may be multiplexed with the pacing signal (as described in greater detail below) so that pressure sensing and telemetry would occur between pacing signals, for example as taught by Barcel (U.S. Pat. No. 5,275,171) or Weijand et al. (U.S. Pat. No. 5,843,135), both incorporated by reference herein.

In one embodiment, pressure sensor electronics are integrated within a miniature hermetically sealed sensor package implanted in the heart, minimizing the number of conductors required in the lead between the sensor and the CRM apparatus generator housing. In this embodiment, the pressure sensor lead may also be used for pacing, with the sensor package, or portion thereof, used to include one of the electrodes of the CRM apparatus. In addition, in one embodiment, some of the pacing electronics are integrated within the sensor package that is implanted within the heart. This has the advantage that the lead conductors are isolated from the pacing electrode, providing immunity from induced currents when, for example, the patient is placed in the rapidly changing strong magnetic fields of a magnetic resonance imaging machine.

In clinical use, conventional cardiac pacemakers use analog voltages on the lead between the pacemaker generator and the heart for pacing, sensing and physiological measurements. As such, the sensing signals in particular are subject to noise due to muscular activity, radio frequency (RF) interference, and potential cross-talk between physiological and electrical sensing signals. Lead conductors carrying analog signals act as antennas for RF noise and for induced voltages due to RF energy used in magnetic resonance imaging (MRI) scanners. RF noise on a sense conductor may cause erroneous pacing, even with sophisticated filtering algorithms that are commonly used in pacemaker sensing systems. Voltages induced by RF and changing magnetic fields are a primary reason why MRI scanning is contraindicated for patients with implantable cardiac pacemakers.

In one embodiment, a pacemaker is provided in which the electronics for producing the pacing pulse output and for sensing the ECG are integrated within a sensor package at the site of the pacing electrode, which is generally implanted within the heart. This allows the lead conductors to be substantially isolated from the pacing electrode, thereby providing increased immunity from induced currents when, for example, the patient is placed in the rapidly changing, strong magnetic fields of a magnetic resonance imaging machine. The lead may incorporate one or more sensors without requiring additional lead conductors.

In one embodiment, the electronics in the proximal housing, for example, a housing implanted near the shoulder, operate at lower voltage than voltages required for pacing, and as a result are fabricated using smaller feature size CMOS technology. This allows for a smaller package and lower power consumption. The distal pacemaker components, for example, those located in the heart, are fabricated using larger feature size CMOS technology to handle the higher pacing voltage.

In one embodiment, the system allows sensing signals to be processed within the heart, thereby eliminating the risk of picking up noise with lead conductors. Separate sensing and pacing electrodes may be provided, with no additional lead conductors. This allows the sensing and pacing electrodes to be individually optimized. Pacing electrodes are optimally small in area to minimize required voltage for pacing, while sensing electrodes are optimally of large area to minimize impedance.

Figure 22:
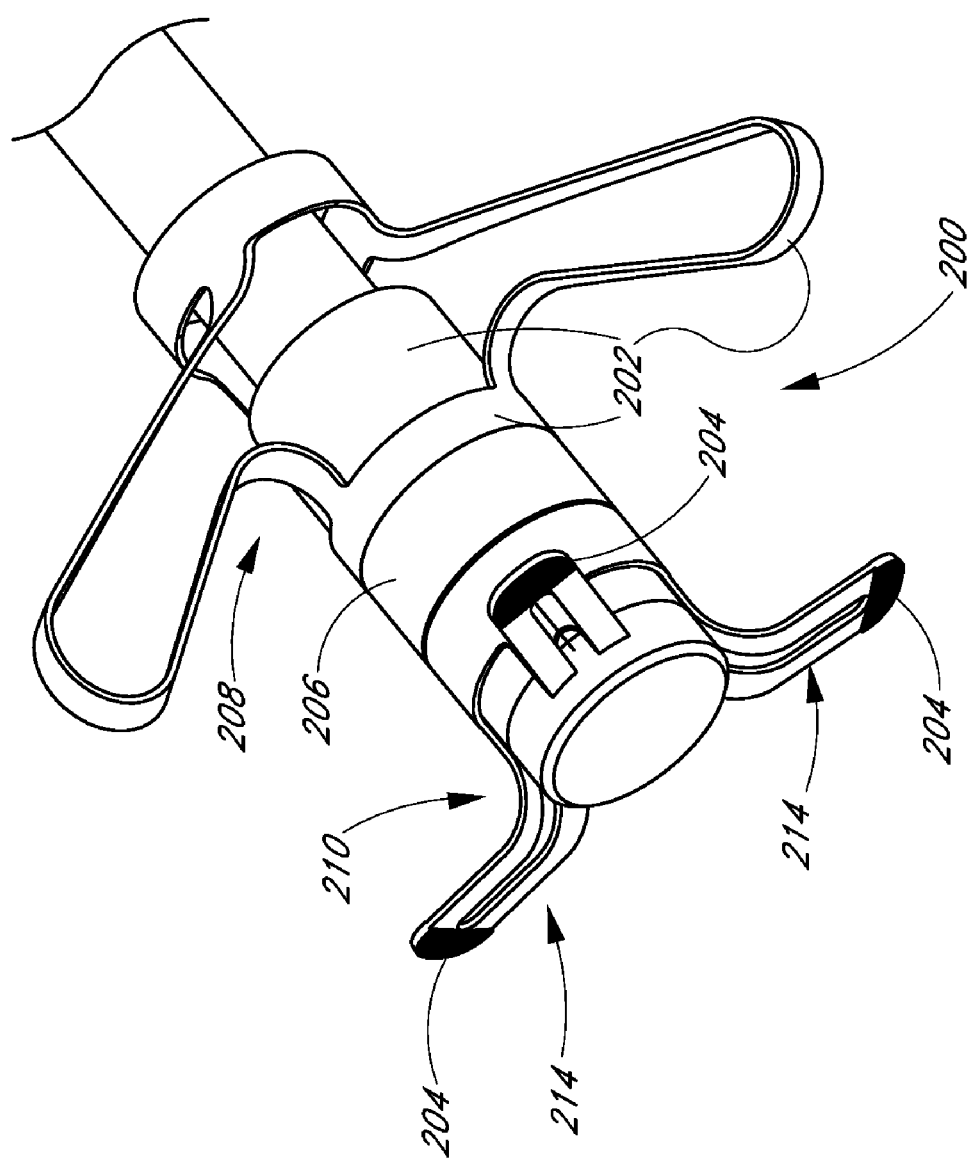
FIG. 22 is a sensor package or module in accordance with one embodiment of the present invention.
Figure 23:
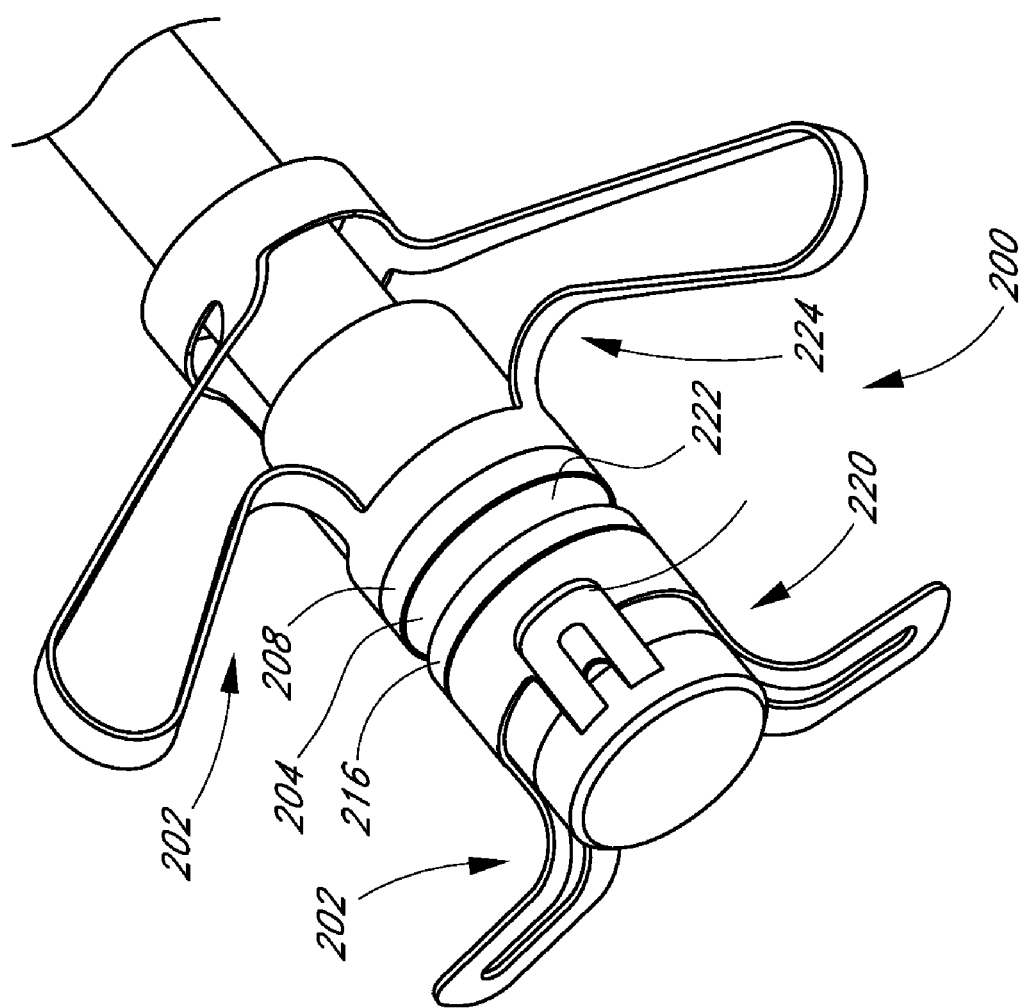
FIG. 23 is another sensor package or module in accordance with another embodiment of the present invention.

Referring now to FIG. 22 and FIG. 23, two embodiments of a sensor package 200 are shown in which separate electrodes for sensing 202 and pacing 204 are included. In the embodiment of FIG. 22, the sensing electrode 202 is located at the proximal portion or segment 208 of the sensor package 200, while the pacing electrode 204 is located at the package distal portion or segment 210. The sensing and pacing electrodes 202, 204 are electrically separated by an insulating segment or ring 206. In one embodiment, the insulating ring 206 is a cylindrical ceramic segment to which metallic proximal and distal segments 208, 210 of the sensor package 200 are hermetically fastened. Hermetic fastening may be achieved by using methods that are well known to those skilled in the art, such as, for example, braising.

In one embodiment, the surface area of the pacing electrode 204 is reduced by coating selected areas of the metallic distal segment 210 with an insulating material. In one embodiment, the insulating material is a tenacious thin coating such as, for example, parylene. One or more selected small areas may be masked off prior to coating to provide for one or more electrically conducting pacing electrodes 204. Referring now to FIG. 23, in one embodiment, the pacing electrode 204 includes an insulated band 222. In another embodiment, the pacing electrodes 204 include areas on the distal anchor members 214 such that the pacing current is applied preferentially to the left atrial wall of the septum. In one embodiment, the pacing electrodes 204 include metallic electrodes fastened to tips of one or more of the distal anchor members 214. In one embodiment, the metallic tip electrodes are made of tantalum, which has the desirable property that it can be made as a porous, high surface area material. It will be familiar to the skilled artisan that such materials reduce contact impedance with tissue. Other materials known in the art to make effective pacing electrodes include titanium nitride and a coating of finely divided platinum called "platinum black." Tantalum has the additional property of high x-ray density, which allows the anchor tips to be visualized under fluoroscopy for verifying the positioning and deployment of the anchor 214.

Referring now to FIG. 23, in another embodiment, two insulating ceramic segments 216, 218 are provided, which divide the sensor package housing 200 into distal, middle, and proximal metallic segments 220, 222, and 224. In one embodiment, the distal and proximal metal segments 220, 224 are substantially uncoated and serve as a sensing electrode 202, while the middle metallic segment 222 includes the pacing electrode 204. In a further embodiment, portions of the middle segment 204 are coated with a material such as, for example, parylene, to produce one or more smaller area pacing electrodes.

In one embodiment, the pacing and sensing electrodes 202, 204 of FIG. 22 and FIG. 23 are electrically coupled to pacing electronics located within the sensor package 200. In another embodiment, the sensor package pacing electronics are configured to detect a specific electrical event within the heart, such as the p-wave of the internal electrogram, as is well known to those skilled in the art of electrophysiology, cardiology and cardiac pacing. In one embodiment, the sensor package pacing electronics are further configured to send a digital signal indicating a sensed event, such as detection of the p-wave, to the pacing electronics in the proximal housing, as described further below.

In one embodiment of the present invention, a defibrillator and an implantable heart monitor (such as described above with reference to FIG. 1 through FIG. 5) are combined to provide the following functionality via an essentially standard pacing/defibrillator lead with only two conductors: (1) provide power to a physiologically optimized dosimeter (POD) measurement module(s); (2) provide signaling for atrial and/or ventricular pacing and sensing, (3) provide for atrial and/or ventricular defibrillation through a third lead attached to a defibrillation electrode; (4) provide for programming of the physiological sensor package; and (5) provide measurement data from the physiological sensor package(s) to the monitor/defibrillator housing for storage and recovery by, e.g., a doctor or the patient via the patient signaling module.

Figure 24:
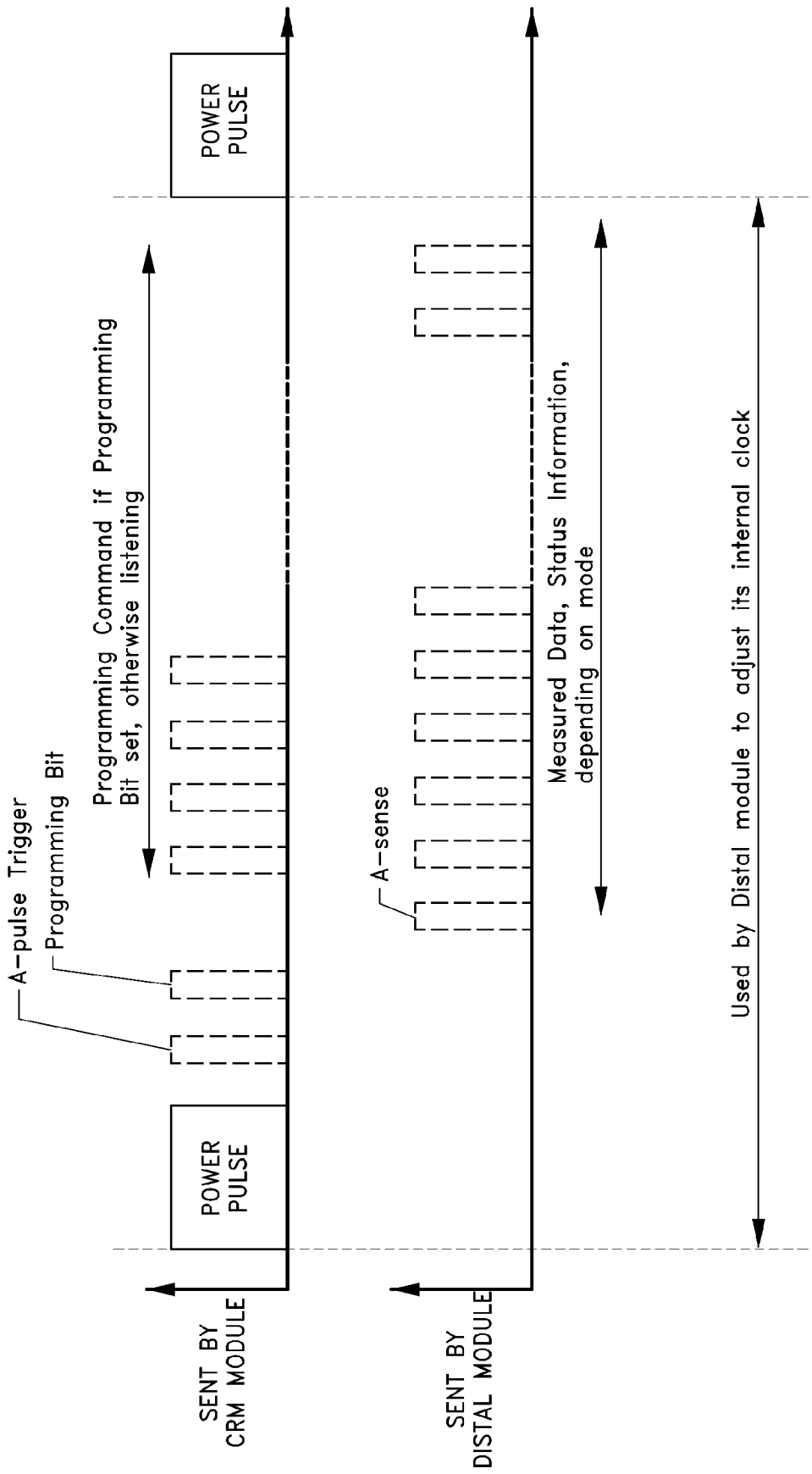
FIG. 24 is a pulse timing diagram showing one embodiment for sensing one or more physiological parameters and performing cardiac pacing using a two-conductor digital sensor/pacemaker lead.

In one embodiment, digital signaling is used to provide for power, two-way data communication, and pacing over a two-wire lead. In one embodiment, digital signaling consists of dividing a "frame" of a defined duration into a number of distinct sub-frame intervals, each with a defined function, as shown in the pulse timing diagram in FIG. 24. In one interval, a power pulse may be provided to charge the power supply of the sensor/pacing module. In one embodiment, the power pulse is provided during the first interval of every frame, so that the power pulse defines the end of one frame and the beginning of the next frame. In one embodiment, power pulses are generated at a precisely timed frequency within the generator module and this timing is used within the sensor/pacing module(s) to adjust an internal RC or current source clock for better synchronization between the distal sensor/pacing module and the generator module at the proximal end of the lead. Between one power pulse interval and the next, other intervals may be defined as needed for the transmission of data and signals over the lead. In one embodiment, the amplitude or magnitude of the power pulse is the same as the amplitude or magnitude of the data pulses, such as shown in FIG. 24. However, in other embodiments, the amplitude or magnitude of the power pulse is greater than, or less than the amplitude or magnitude of the data pulses. In one embodiment, the amplitude of the power pulse does not vary between pulses, and in another embodiment, the amplitude of the power pulse varies between pulses, or within pulses.

In the embodiment described in FIG. 24, the next two intervals are provided for signaling from the CRM module to the sensor/pacing module(s). In one embodiment, these two intervals are called the "download interval." The first interval is asserted by the CRM module to command that a pacing stimulation pulse be applied (e.g., A-pulse Trigger). The second interval is asserted by the CRM module to indicate that commands producing a change in the mode of operation of the sensor/pacing module are to follow (e.g., Programming Bit set). Following the download interval, an "upload interval" may be provided for communication of information from the sensor/pacing module back to the generator module. As shown in FIG. 24, this information may include a bit that, if asserted, indicates an atrial and/or ventricular sensed event, and/or measurement data, and/or status information about the current mode of operation of the sensor/pacing module.

In one embodiment, the type of data following the A-sense upload interval may be either upload or download data depending, for example, on whether a programming or pacing command had been asserted. In the embodiment of FIG. 24, if neither of the two download bits has been asserted in the current or the previous frame, the time intervals following the A-sense interval are used by the sensor/pacing module to upload measured data, such as pressure, temperature and electrogram (IEGM) waveform data. In order to conserve power, the pressure, temperature and IEGM data could be measured and output at a low duty cycle. If the Programming Bit is asserted in the current frame, the sensor/pacing module is set to listen for programming command bits sent by the CRM module. If either the A-pulse trigger or the Programming Bit was set in the previous frame, the sensor/pacer module provides status information indicating whether the command was successful.

In one embodiment, the download and upload intervals are subdivided into data words, each containing a predefined number of bits, so that multiple pieces of information are communicated. For example, the download interval may consist of a pacing command pulse followed by one or more programming bits. The upload interval may consist of a sensing bit (set if P- or R-wave of internal electrocardiogram is sensed by the measurement module), followed by a predetermined number of bits of pressure data, followed by a second predetermined number of bits of temperature data. All signals, including pressure, IEGM, and temperature, may be "alternated" in some fashion rather than being included in any single frame, to allow for shorter frames and therefore more frequent power supply support and synchronization. It will be clear to one skilled in the art that data from additional sensors may be appended in the same way. In one embodiment, additional checksum bit(s) are added to guard against data transmission errors.

In one embodiment, the power and signaling pulses described above are carried between the CRM module and the measurement module(s) via a two-conductor lead. Each conductor is internally connected within both modules. The first conductor may also be attached to the "indifferent" electrode (as shown, for example, in FIG. 31), which defines the baseline potential for sensing and pacing. In one embodiment, a low impedance common conductor such as drawn-filled-titanium (DFT) wire extends between the indifferent electrode and the measurement module in order to prevent the signaling pulses from affecting the sensing of the electrogram.

Figure 32:
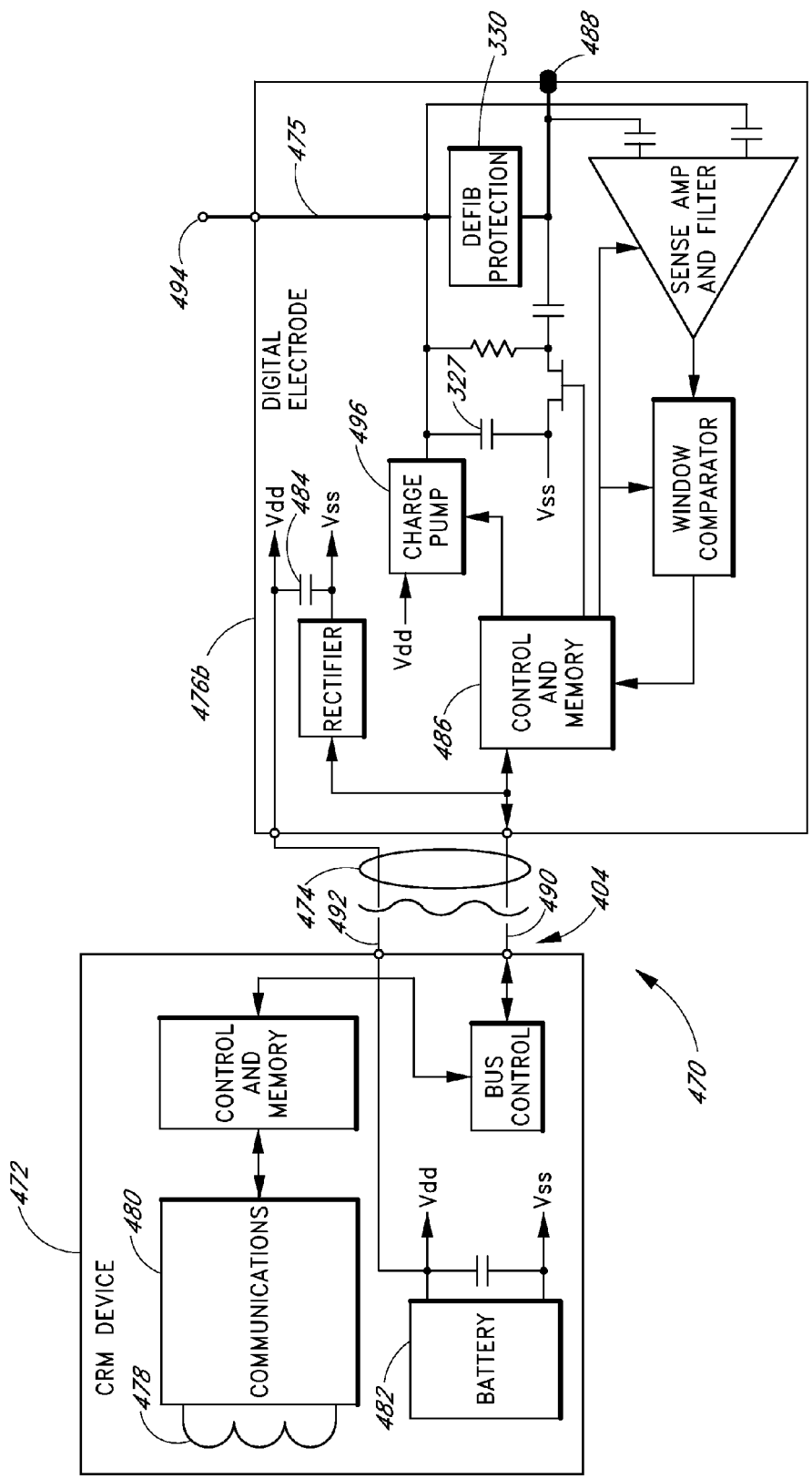
FIG. 32 is a pacemaker with a digital electrode as in FIG. 31, wherein the electrode module additionally comprises the charge pump and pacing pulse capacitor in accordance with one embodiment of the present invention.

In another embodiment, the indifferent electrode 494 is connected to the internal circuitry of the sensing/pacing module 476 (sometimes referred to as a distal housing, a digital electrode housing, a distal module, a distal electrode module, or a housing) by a third conductor 475 (as shown, for example, in FIG. 32). The first conductor 490 is electrically isolated from the body. Advantageously, this conductor 490 is physically contained by the outer coaxial second conductor 492 and the housings 472, 476 at each end. The housing 472 is sometimes referred to as a CRM package or proximal housing. To ensure electrical isolation at the CRM package 472, a spring contact (without a setscrew and seal) is provided on the first, inner conductor 490 rather than on the outer conductor 492. By providing a set screw to the outer conductor 492 only, electrical isolation of the inner conductor 490 is preserved along the entire lead length, from the proximal housing 472 to the distal housing 476. In one embodiment, the outer conductor 492 extends all the way from the proximal housing 472 to the distal housing 476, thereby shielding the inner conductor 490 over its entire length, including the portion or lead segment that extends between the indifferent electrode 494 to the distal housing 476. The indifferent electrode 494 is sometimes referred to as the indifferent electrode 14 or the indifferent electrode 458.

The measurement module stores electrical energy from one or more power pulses and applies an appropriate pacing pulse to a pacing electrode when a pacing command is received from the CRM module during the download interval. Importantly, the distance between the pacing electrode and the indifferent is substantially reduced, thereby greatly reducing any induced voltages during magnetic resonance imaging (MRI) or electrocautery procedures. In one embodiment, the sensor/pacing module stores electrical energy from one or more power pulses and applies an appropriate pacing pulse to the pacing electrode when a pacing command is received from the CRM module, for example, during the download interval. In an alternative embodiment, pacemaker voltage and/or timing are provided by circuitry within the sensor/pacing module, autonomous from the CRM module. In both embodiments, the sensor/pacing module may generate or store electrical energy for application of an appropriate pacing pulse to the pacing electrode at intervals defined by either the CRM module or the circuitry within the sensor/pacing/measurement module itself. In another embodiment, the pacing interval is modified or synchronized with a second digital electrode in another location by the generator module by downloading the appropriate command to the sensor/pacing/measurement module.

In one embodiment, the circuitry includes current and voltage limiting features known to those skilled in the art to provide protection from defibrillator discharges, either from an external or implantable defibrillator. In one embodiment, series-connected oppositely oriented zener diodes are provided for defibrillation protection as described, for example, by Langer (U.S. Pat. No. 4,440,172, incorporated by reference herein).

Figure 25:
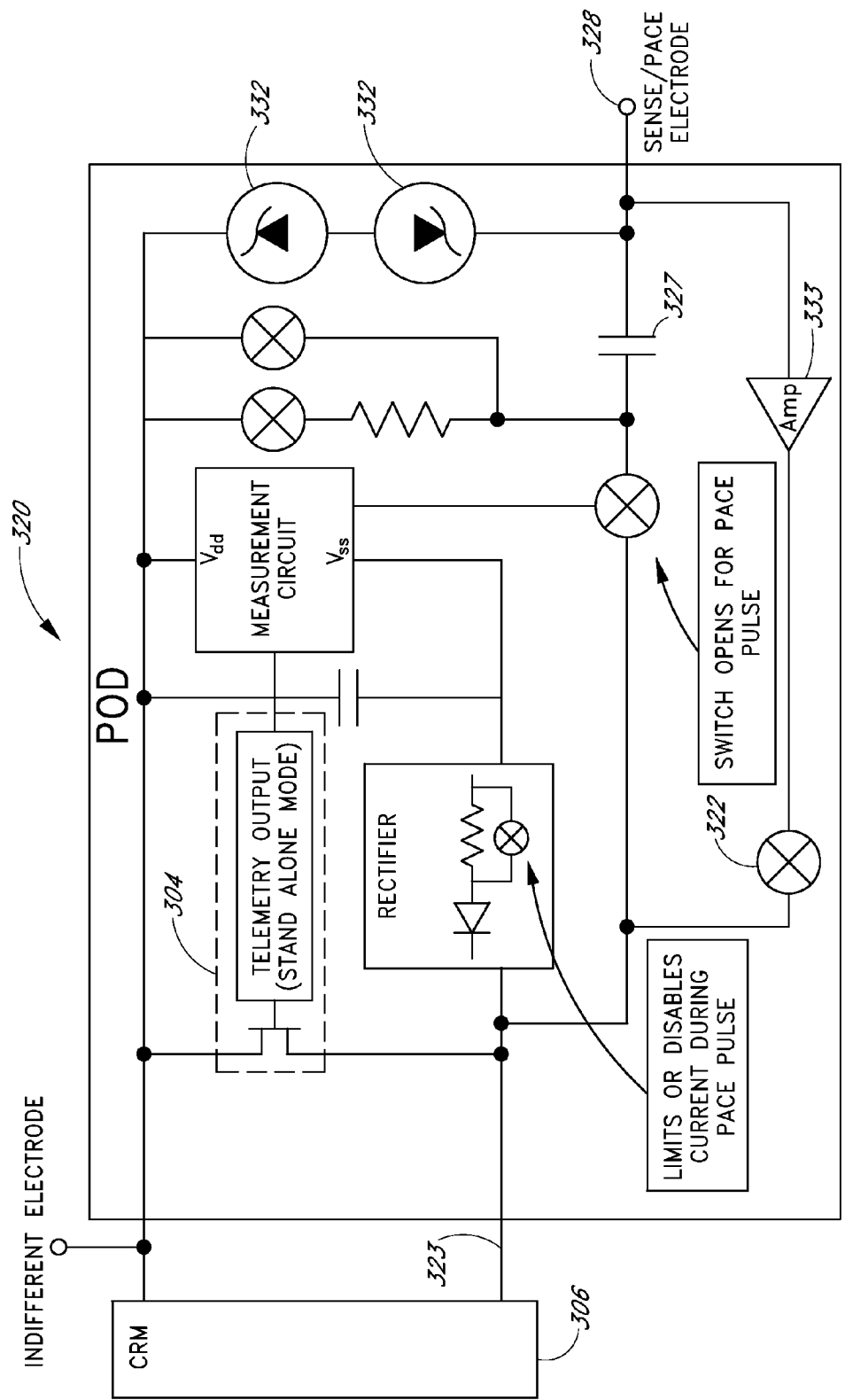
FIG. 25 is a schematic showing one embodiment of circuitry that provides both pacing and physiological monitoring over a two-conductor pacemaker lead.

Referring to FIG. 25, three embodiments are described to implement a hybrid approach for performing pacing and physiological sensing using the same lead.

In the first embodiment, the output voltage during the pacer pulse is provided by a CRM device 306. Alternatively, in another embodiment, an output voltage storage capacitor and a charge pump are provided by a device contained within the intracardiac module 320.

Sensing may be performed according to at least two different embodiments. In one embodiment, the circuitry is located in the intracardiac module 320, and a digital signal is provided back to the CRM 306 when a p-wave is detected. In the second embodiment, an IEGM signal detected at the sense/pace electrode 328 is amplified by an amplifier 333 and applied via switch 322 to the lead 323. For both of these options, IEGM sampling is time-multiplexed in the frame sequence.

Either on-chip or back-to-back Zener diodes 332 are provided in the device 320, thereby keeping the RF path (during MRI) small in order to improve immunity.

2. Upgrade from Stand-Alone to Combination System

Figure 26A:
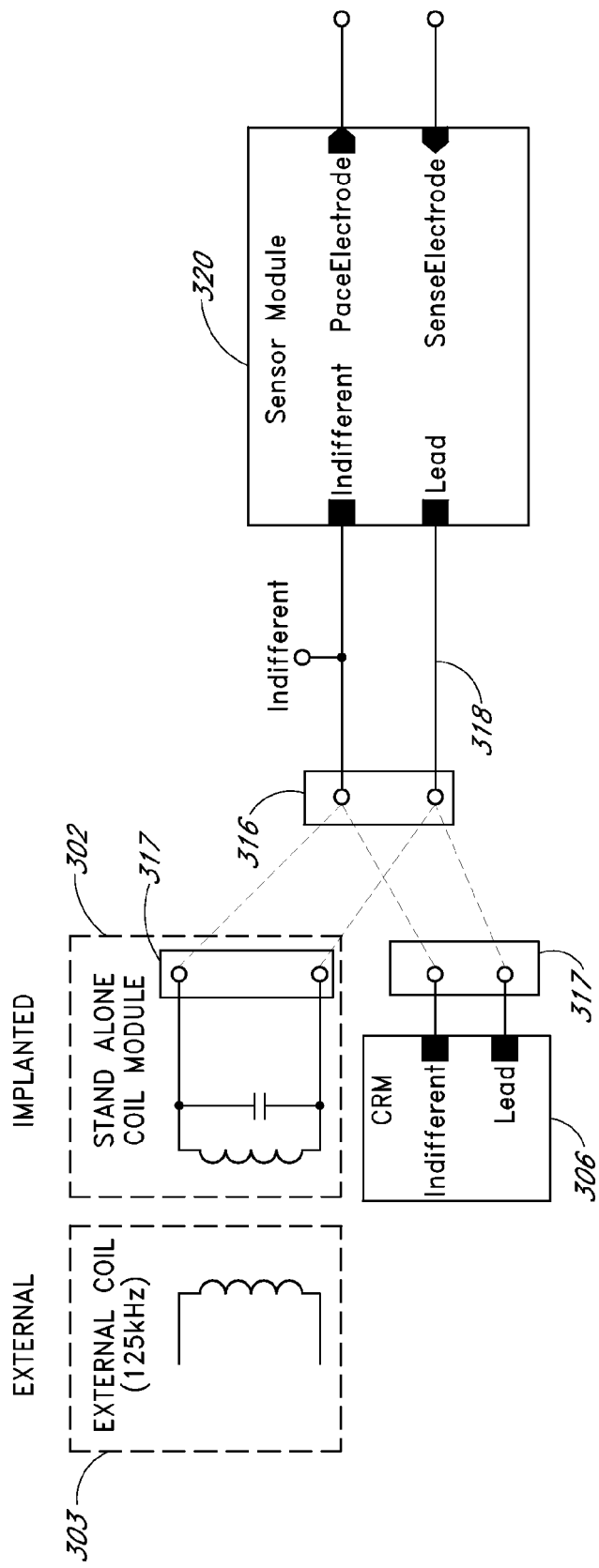
FIGS. 26A-D are schematics showing circuitry within a sensor module in accordance with another embodiment of the present invention.

Referring now to FIG. 26A, in one embodiment, the same sensor and lead 318 can be used either as part of a Stand-Alone system (such as a heart monitoring system, pressure monitoring and feedback system, HeartPOD™, POD, or apparatus for treating congestive heart failure, as described above) or as part of a combination system that includes a CRM or automated therapy system. This flexibility allows for the implantation of a Stand-Alone intracardiac module 320 that can be "upgraded" to include pacing and/or defibrillation therapy if the need arises without having to implant an additional lead. The combination system also allows the communication coil module 302 of the apparatus for treating congestive heart failure (such as that described above with reference to FIG. 4) to be removed and replaced with a CRM 306. Furthermore, in one embodiment, the sensor electronics (which in one embodiment are located in a distal sensor package 320 implanted within the patient's heart, as schematically illustrated in FIG. 26B) include the pace/sense circuitry that allows it to be used as a smart "digital" electrode in conjunction with a CRM device, as described below.

In an alternate embodiment, an additional lead conductor is included to allow operation with pacing and sensing electronics located within the CRM housing 306 of a CRM device. In one embodiment, a sensor or sensor module 320 is coupled to the distal end of a lead 318, which has a proximal IS1 connector 316, as is familiar to those of skill in the art. In one embodiment, an upgrade is performed by surgically opening the subcutaneous pocket, unplugging the IS1 connector 316 from the RF coil antenna 302, or pressure monitoring and feedback implanted module, and plugging the lead 318 into an IS1 port 317 of a CRM housing 306, as described in greater detail below.

In one embodiment, the intracardiac module (ICM) containing the sensor is powered either by a pair of tuned coils, 302 and 303, (Stand-Alone configuration) at 125 kHz (although any other suitable frequency could be used) or "power" pulses from the implanted CRM at a frame frequency (CRM configuration). In the Stand-Alone configuration, data from the sensor is telemetered to a patient advisory module (not shown) using reflected impedance. Other telemetry schemes may also be employed, such as disclosed, for example, in U.S. Pat. Nos. 4,681,111 and 5,058,581 to Silvian, both incorporated herein by reference. Electronics provided within the intracardiac module comprises circuitry that detects whether an incoming signal is a 125 kHz signal (as may be provided by the external patient advisory module, in one embodiment) or a frame power pulse at a frequency between about 50 Hz and 20 kHz. (as may be provided from a CRM device, in one embodiment). In one embodiment, a frame rate between about 600 and 800 Hz is used. This autosensing functionality allows the pressure monitoring and feedback system described herein to be "upgraded," whereby the additional functionality of a CRM system, such as a pacemaker or defibrillator or other such device, is able to be provided by merely changing, or swapping one implanted component, or module, with another. At least two methods are provided for determining which configuration (Stand-Alone or combination) is operable, as described below with reference to FIGS. 26A-D. One method is based on frequency discrimination and the other is based amplitude discrimination. In both cases, the signals are half-wave rectified by rectifier 300 to provide power for the sensor (and pace/sense) electronics. As is recognized by the skilled artisan, full-wave rectification could be employed as an alternative. Two embodiments of rectifier 300 are provided in FIGS. 26C-D.

Figure 26B:
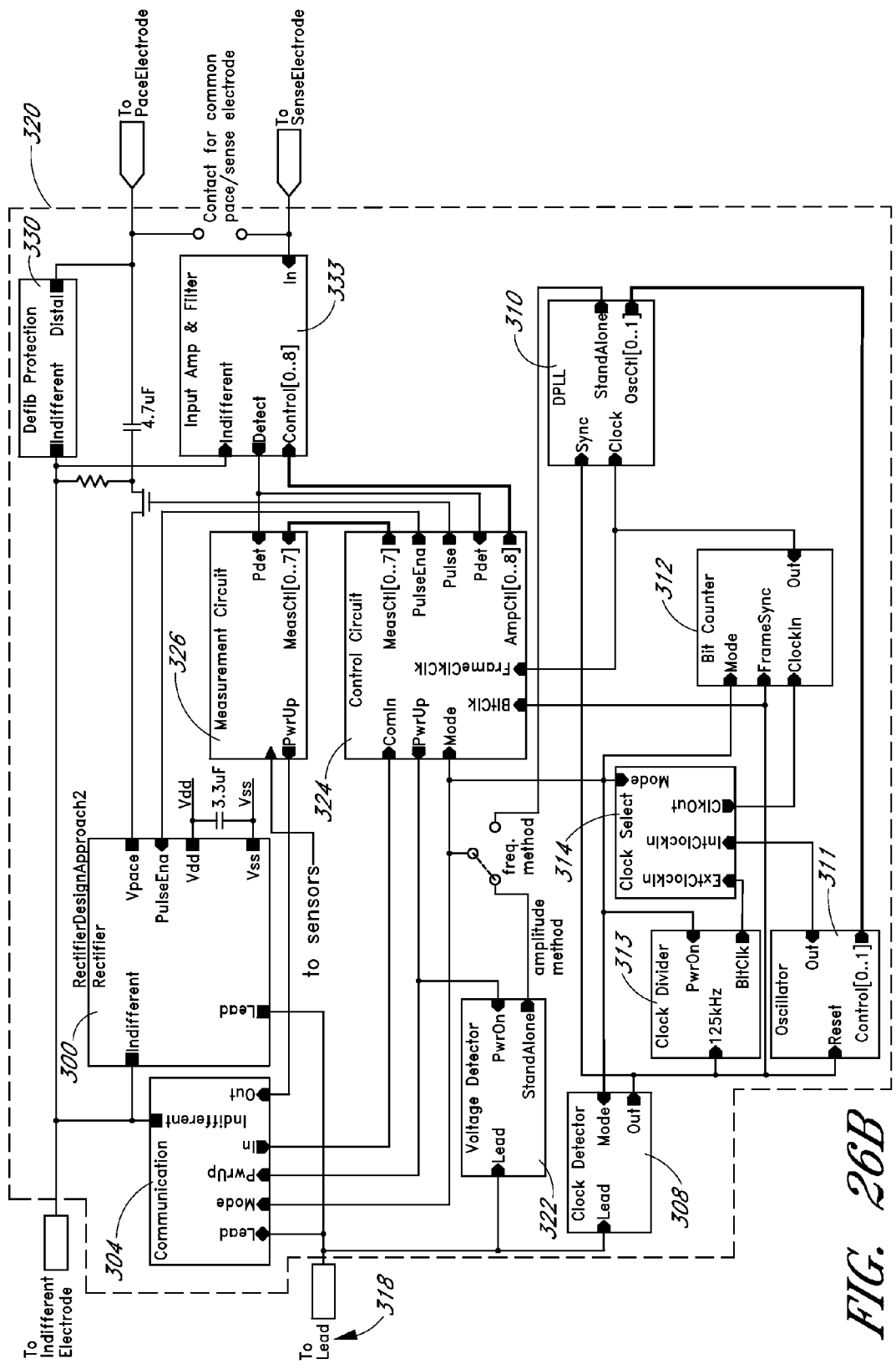

Referring now to FIG. 25 and FIG. 26B, in one embodiment, in the Stand-Alone configuration (e.g., when a CRM 306 is not present), the 125 kHz signal is output from a tuned coil 302 that resides in a subcutaneous pocket. The 125 kHz signal is rectified to provide DC power for the sensor electronics of the sensor module 320 and a 125 kHz clock for operation and timing. A shorting FET, which in one embodiment is located within communications module 304, is placed across the 125 kHz input to provide a reflected impedance signal that can be detected by the external device for telemetry of the sensor(s) output. The FET is disabled after power up until the POD has determined that the Stand-Alone configuration is operable. Although full wave rectification could be used, in one embodiment, half wave rectification is employed. Detection of the unused half cycle is one of the methods used to differentiate between the two modes of operation. In one embodiment, power is turned off to the pacing and sensing electronics in the Stand-Alone configuration to conserve power.

In one embodiment, in the CRM configuration, the sensor lead is attached or coupled to a CRM device 306 that provides a power pulse at a fixed frame rate, a pace trigger signal, and apparatus for changing memory registers in the intracardiac module (ICM). The power pulse is rectified to provide DC power for the ICM electronics. The reflected impedance shorting FET used in the Stand-Alone configuration is disabled at power up and in CRM mode. As shown in FIG. 26B, a frame clock detector 308 is employed to obtain the frame clock that is input to a DPLL 310 (digital phase lock loop). The DPLL 310, by way of example, includes or is coupled to an oscillator 311 with electronic frequency adjustment with its output used for operation and timing for the ICM electronics. This clock is fed into a divide by N counter, or bit counter, 312 through a clock select switch 314. The output of the bit counter 312 is coupled to the other input the DPLL 310 whose output is connected to the frequency adjustment of the oscillator 311. This provides for an internal clock, which is N times the frame clock and is synchronized to the frame clock. In the Stand-Alone configuration, the divide by N counter 312 receives its clock signal from the 125 kHz clock divider 313. In another embodiment, an analog PLL is used instead of a digital PLL. The DPLL 310 also provides a signal to indicate the mode of operation (the frequency discrimination method). If the DPLL 310 is locked at its limit (no sync), then Stand-Alone operation is indicated. In the CRM mode, the CRM device 306 goes to high impedance between power pulses during the upload period, thereby allowing the ICM to send sensor output(s) and a sense-detect signal to the CRM device 306. In one embodiment, the output of the frame clock detector 308 is also used to reset oscillator 311 and divide by N counter 312.

Since the physical connection is different between the two modes of operation, the detection mechanisms for mode determination can be optionally latched at power up and then disabled to conserve power.

One embodiment of the present invention provides for a novel variation of a standard IS1 header. In conventional IS1 headers, typically a spring connector is employed for the outer conductor and a setscrew is used for the inner conductor. Both the 125 kHz for the Stand-Alone device and the digital power/signaling signals of the combination device are isolated from the body, and especially the heart, for patient safety. Advantageously, in one embodiment of the present invention, the active conductor is the inner conductor of a coaxial lead and a spring connector is used for the inner conductor in the IS1 header, while the setscrew is used to secure the outer conductor. This assures that, even in a damaged lead or leaking setscrew seal, all leakage paths to the body are completely surrounded by the common coax outer conductor, and therefore isolated from the body.

In one embodiment, the system is designed to operate in at least two different configurations, and in at least two modes of operation. A first mode is the "Stand-Alone Configuration." A second mode is "the CRM Combination" (or "Combination Configuration"). One advantage of a multi-configuration system is that it allows the device to be implanted as a Stand-Alone system for CHF therapy and later to be upgraded for use with a CRM device if the patient's condition changes. In the Combination Configuration, in one embodiment, the sensor module 320 acts as a pace/sense electrode for the CRM device.

In one embodiment, there are three modes of operation based on the configuration: (1) A "Power-Up Mode" which is used to automatically detect whether the Stand-Alone Configuration or the Combination Configuration is present. This mode is entered into when the power is applied to the sensor module 320. As described below by way of example, at least two alternative methods are described for detecting the configuration. Alternative methods will be apparent to one skilled in the art; (2) A Stand-Alone Configuration; and (3) A Combination configuration.

In one embodiment, the CRM module logic includes logic to detect any problems with the sensor module 320. Should any unrecoverable problem be detected, the CRM module stops the power pulses to the sensor module 320 and restarts, thus allowing for a new power-up sequence. In another embodiment, restart can be limited to be under physician supervision.

The following paragraphs describe the functional components of one embodiment of the upgradeable intracardiac module 320, with reference to FIG. 26B:

Communication block: In one embodiment, a communication block 304 is provided. In one embodiment, the communication block 304 is responsible for the bidirectional communication. The Mode and PwrUp inputs define how the device operates. Incoming communication in a preferred embodiment is by FSK on the 125 kHz carrier for the Stand-Alone Configuration and by digital command signals between power pulses for the Combination Configuration. Outgoing communication in one embodiment is by reflected impedance for the Stand-Alone Configuration and by digital signals between power pulses for the Combination Configuration. During the power-up mode, all outgoing communication is suppressed. The figure for Combination Configuration signals depicts a RZ code. One skilled in the art will understand that other encoding methods, such as NRZ, Manchester, etc., can also be used in accordance with several embodiments of the current invention.

Voltage Detector Block: In one embodiment, a voltage detector block 322 is provided. In one embodiment, the voltage detector block 322 detects the operating configuration after power is applied (during the power-up mode). In one embodiment, it only needs to be powered during this brief time and can be disabled to conserve power. In one embodiment, the voltage detector block 322 detects whether or not there are 125 kHz excursions above Vdd, which will occur in the Stand-Alone Configuration, but not in the Combination Configuration.

Clock Detector Block: In one embodiment, a clock detector block 308 is provided. In one embodiment, this block 308 is a comparator with two thresholds that outputs a digital clock signal from the signal on the lead. In the Stand-Alone Configuration, the threshold is set to Vdd and the output is a 125 kHz square wave. In both the Combination Configuration and Power-Up Mode, the threshold is set to approximately 0.5 V below Vdd (although other thresholds may be used) and the output is used to recover the frame sync which are the power pulses in the combination mode and 125 kHz during the power-up mode in the Stand-Alone Configuration. One reason for the 0.5 V threshold is to allow signaling pulses to have lower amplitude than the power pulses and will not be erroneously detected as clock pulses (and will also dissipate less power). Alternatively, the midpoint supply voltage may be used as a threshold, with equal amplitude power and signaling pulses, provided that the DPLL 310 and related timing provides for a defined gap between the last signaling pulse and the next power pulse.

Clock Divider Block: In one embodiment, this block 314 is provided. In one embodiment, this block 314 divides down the 125 kHz to provide a bit clock in the Stand-Alone configuration. It is disabled in the CRM configuration.

Oscillator block: In one embodiment, an oscillator block 311 is provided. In one embodiment, this block 311 contains a capacitor that is charged up from Vss to a settable threshold voltage. A short reset pulse is provided to fully discharge the capacitor after the threshold reached and if a reset pulse is provided. The threshold is determined by the oscillator control lines that specify to either to increase or to decrease the threshold by a small delta V. In an alternative embodiment, the capacitor is arranged in a binary array and the DPLL 310 is an up/down counter.

Clock Select Block: In one embodiment, a clock select block 314 is provided. In one embodiment, this block 314 switches the bit clock to the sensor module's internal oscillator output for the CRM Combination Configuration and during the power-up mode. For the Stand-Alone Configuration, the bit clock 314 is switched to the output of the 125 kHz clock divider.

Bit Counter Block: In one embodiment, a bit counter block 312 is provided. In one embodiment, this block 312 is a divide by N counter that is reset by the Frame sync in the CRM configuration and during power-up. It provides the bit timing sequence for each frame. During power-up, in the Stand-Alone Configuration, it is substantially held reset by the 125 kHz "frame sync" pulses.

DPLL Block: In one embodiment, a DPLL block 310 is provided. In one embodiment, the DPLL 310 provides the feedback to control the internal oscillator frequency to be N times the frame sync. In one embodiment, it also determines the configuration during power-up mode by detecting that the Bit counter 312 is stuck reset.

Figure 26C:
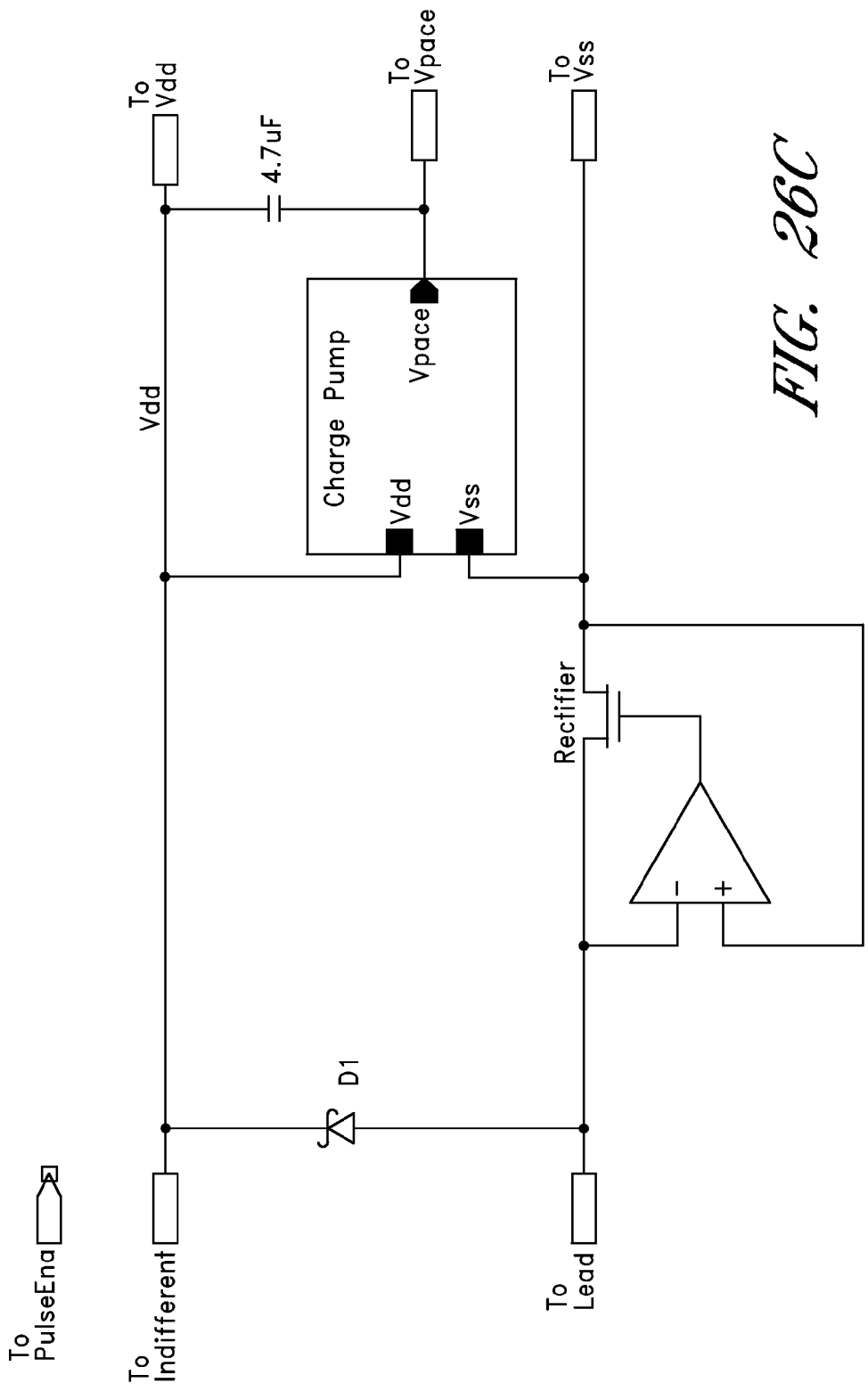
Figure 26D:
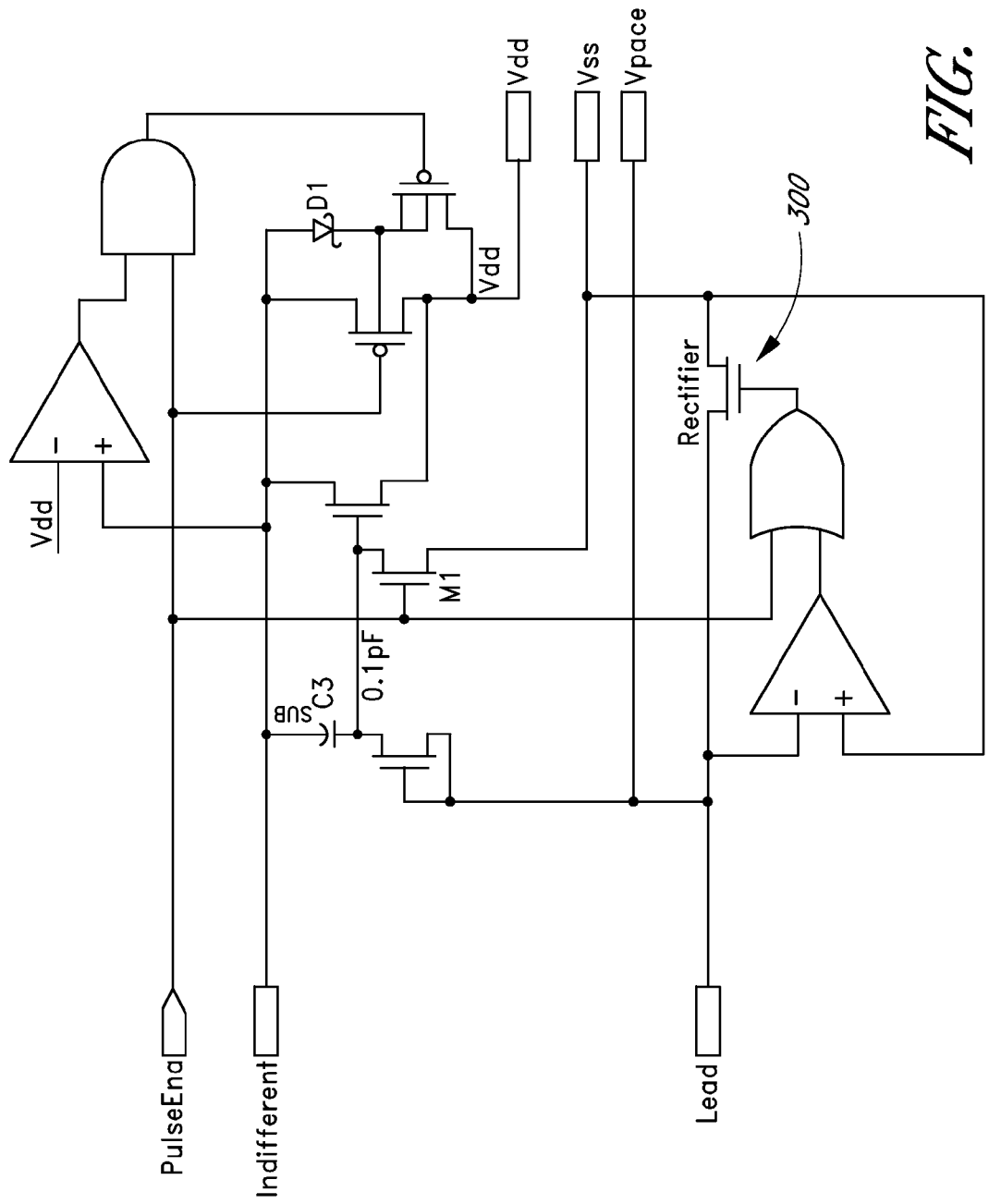

Rectifier Block: In one embodiment, a rectifier block 300 is provided. Two alternative embodiments are shown in greater detail in FIGS. 26C-D. In the embodiment of FIG. 26C, Vdd is tied to the outer lead winding which is tied to the Indifferent Electrode. A schottky diode is provided to protect the CMOS from the positive swing on the inner "Lead" winding in the Stand-Alone configuration. Alternatively, a full wave rectifier could be used. A separate charge pump and pacing output voltage storage cap is provided to generate and store the pace voltage. In the second rectifier embodiment, which is illustrated in FIG. 26D, the charge pump and storage cap are omitted from the sensor module. Instead, a MOS switch is provided between Vdd and the Indifferent. This switch is normally ON but is switched OFF during a pacer pulse so that the pace voltage is stored in the CRM device and switched out to the distal electrode. Additional circuitry is provided to handle start-up and well switching issues.

Control Circuit Block: Referring back to FIG. 26B, in one embodiment, a control circuit block 324 is provided. In one embodiment, this block 324 provides substantially all the memory storage, logic and timing required for operation.

Measurement Circuit Block: In one embodiment, a measurement circuit block 326 is provided. In one embodiment, this block 326 provides substantially all the measurement circuitry to measure pressure, temperature, etc.

Input Amp & Filter Block: In one embodiment, an input amp & filter block 328 is provided. In one embodiment, this block 328 contains an AC coupled amplifier, filter and window comparator for the detection of heart depolarization signals (P-wave and/or R-wave). The circuits for this function are well known in the art. This block 328 is shown connected to a separate sensing electrode. Normally the pacing and sensing electrode are the same, which is still possible in this invention by merely shorting these points together. Advantageously, one embodiment provides for the possibility of separate pacing and sensing electrodes without having to have a separate lead conductor and extra connector pin. This allows each electrode to be optimized independently for each electrode. In addition, the recovery discharge voltage is eliminated on the sensing electrode, allowing for sensing of the induced P or R-wave for capture verification and/or threshold tracking. This advantage is due to the inclusion of the pacing & sensing electronics remotely in the sensor module. If two distinct electrodes are employed, additional defibrillator protection may be needed for the sense amplifier. This protection is relatively easy because the impedances can be much higher and the induced currents are easily handled.

Defibrillation Protection Block: In one embodiment, a defibrillation protection block 330 is provided. In one embodiment, this block 330 is composed of two back-to-back zener diodes or other method as is known in the art.

Figure 28:
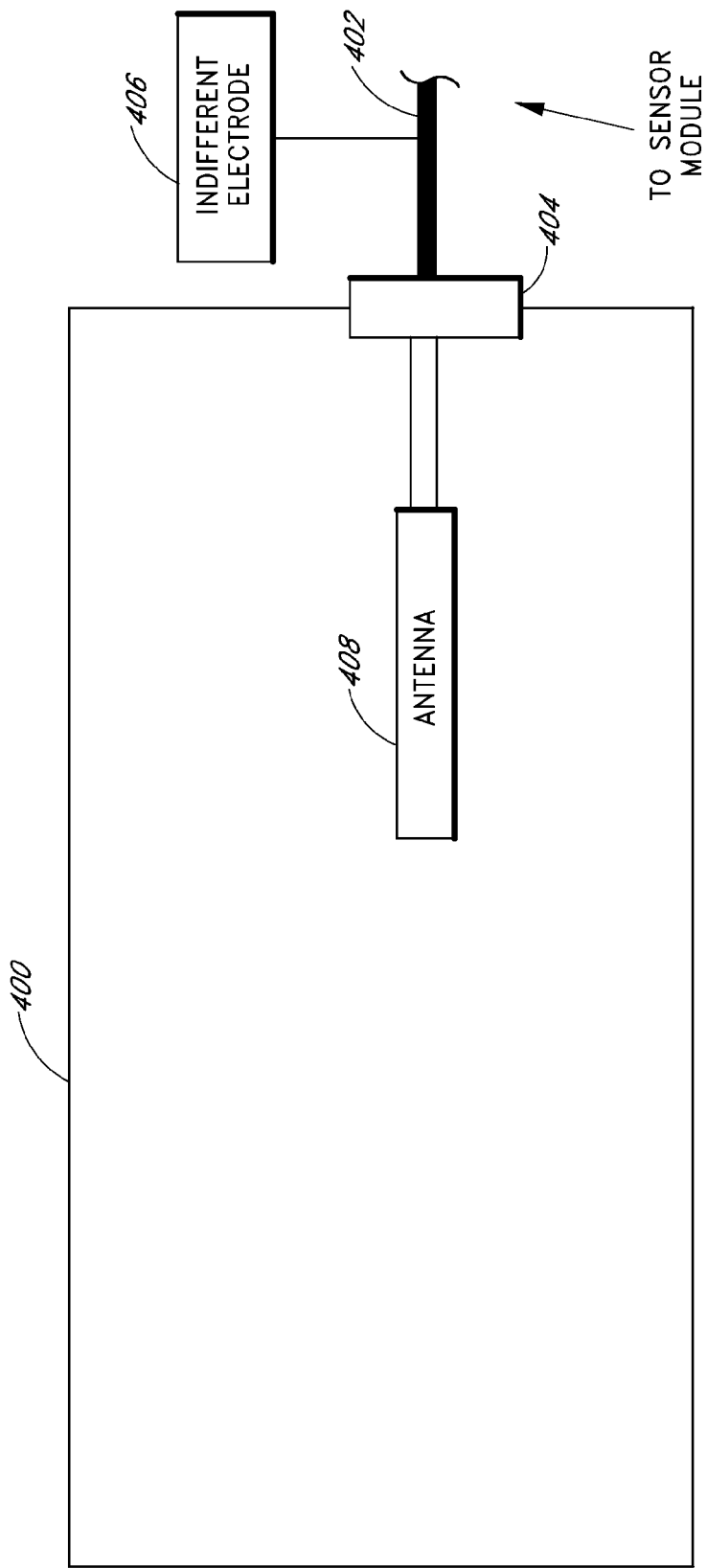
FIG. 28 is an implantable housing in accordance with one "Stand-Alone" embodiment of the invention.
Figure 29:
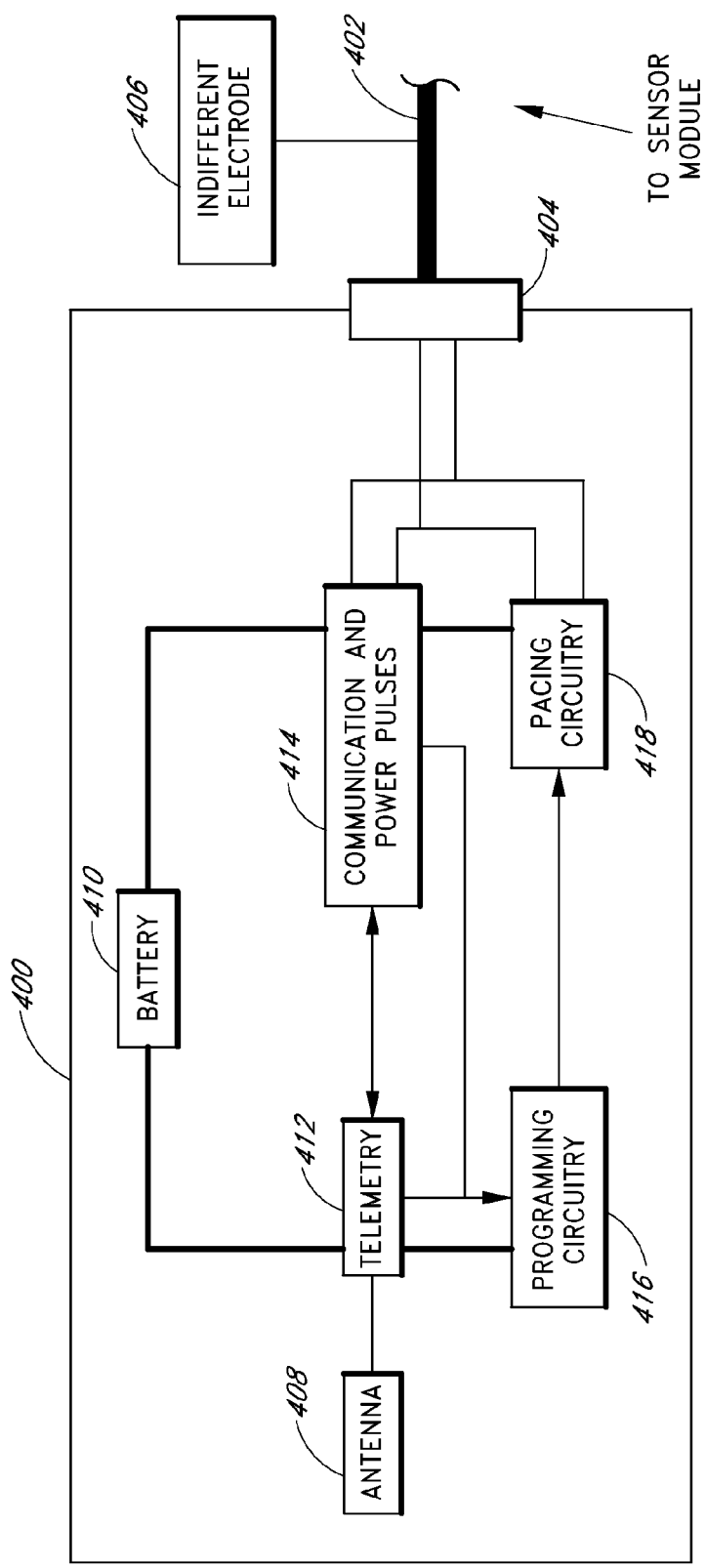
FIG. 29 is an implantable housing in accordance with one "CRM Combination" embodiment of the invention.

One embodiment of an upgradeable system is illustrated in FIG. 28 and FIG. 29. The system of FIG. 28 illustrates a "Stand-Alone" embodiment, and includes an implantable housing 400 coupled to an implantable lead 402 with a connector 404. In one embodiment, the housing 400 is the housing 7 as described above. In another embodiment, the lead 402 is the lead 318 or lead 10 as described above. In one embodiment, connector 404 is the IS1 header 316, IS1 port 317, or connector 10, as described above. The connector 404 may be any connector known to those of skill in the art used to couple an implantable lead to an implantable housing.

The lead 402 is connected to a sensor module (not shown) as described in greater detail above. The lead 402 also has an indifferent electrode 406, which provides a non-stimulatory electrical return path from the patient, as is well known to those of skill in the art. The implantable housing 400 of the Stand-Alone embodiment includes an antenna 408. In one embodiment, the antenna 408 is the antenna 162 or coil 302 as described in greater detail above. The antenna 408 may be any coil of wire as is known to those of skill in the art, which may be used for telemetry communications with an external device, such as a patient advisory module (not shown), as described in greater detail above with reference to FIGS. 4 and 5. In one embodiment, the antenna 408 is coupled to the lead 402 via the connector 404, and functions as described above.

One embodiment of a "combination" unit is described with reference to FIG. 29. As described above, in one embodiment, when the Stand-Alone unit is upgraded to provide CRM functionality in addition to left atrial pressure sensing and patient feedback, the housing of the Stand-Alone system may be exchanged with the housing of a combination system without having to provide an additional lead for cardiac rhythm management.

As illustrated in FIG. 29, in one embodiment, the housing 400 of the combination unit is coupled to a lead 402 via a connector 404 as described above. In one embodiment, the lead is coupled to an indifferent electrode 406, also as described above. In one embodiment, the housing 400 of the combination unit is the same as the housing 400 of a Stand-Alone unit, or CRM housing 306, as described in greater detail above.

The housing 400 of the combination unit includes an antenna 408, battery 410, telemetry module 412, communication and power pulses module 414, programming module 416, and pacing circuitry 418. The battery 410 provides power to the components within the housing 410, as well as those within the sensor module (not shown), as describe above. The telemetry module 412 provides communication between the combination unit and the patient advisory module (not shown). The communication and power pulses module 414 control communication between the sensor module (not shown) and the housing 400 components as well as power distribution to the sensor module from the battery 410. Programming module 416 provides programming control over the system, including the pacing module 418, which controls the transmission of electrical pulses or stimuli as required by the CRM device.

FIG. 29 illustrates one embodiment of a CRM Combination configuration. In this configuration, the housing 400 contains a battery 410 that powers both the CRM device and the sensor module (not shown). The communication and power pulse circuit 414 provides power to and communicates with the sensor module via the lead conductor 402 using, in one embodiment, for example, the coding scheme described with respect to FIG. 24. The communication circuit 414 also decodes physiological sensor signals, such as pressure signals, a-wave and/or p-wave sense signals received from the sensor module via the lead 402. Sense signals received by the communication circuitry 414 are passed to the pacing circuitry 418 where they are used to determine if and when to provide a pacing stimulus.

In one embodiment, the pacing circuitry 418 triggers a pacing stimulus by sending a signal to the communication circuitry 414, which sets the appropriate pulse trigger bit to the sensor module as described above with respect to FIG. 24. In one embodiment, the pacing circuitry 418 delivers the pacing stimulus to the lead 402 a predetermined interval after setting the pulse trigger bit, and commanding the sensor module to allow the pacing stimulus to pass from the lead 402 through the sensor module electronics to the pacing electrode. In another embodiment, the pacing stimulus is applied to the pacing electrode from a storage capacitor within the sensor module when a pulse trigger bit is received by the sensor module from the communication circuitry 414.

In one embodiment, various operational modes and parameters are programmed using an external programming device (not shown) that communicates with the implanted pacemaker transcutaneously using telemetry system 412, which decodes programming commands from a programmer and passes them to the programming circuitry 416. In one embodiment, physiological sensor signals, such as but not limited to pressure, temperature, or internal electrocardiogram signals, are passed from the communication circuitry 414 to the telemetry circuitry 412 for telemetry to the external patient advisory module, such as the patient advisory module illustrated and described above with reference to FIG. 4. In one embodiment, physiological sensor signals are also communicated from the communication circuitry 414 to the programming circuitry 416, where they are used to at least partially to control the operation of the pacemaker in response to the patient's condition.

3. Automated Therapy

According to one embodiment of the current invention, a method for treating cardiovascular disease in a medical patient includes implanting a physiological sensor package and a therapy delivery unit (e.g., the "treatment system") within the patient's body, operating the physiological sensor package to generate a signal indicative of a physiological parameter, communicating the signals indicative of the physiological parameters to a signal processing apparatus, operating the signal processing apparatus to generate a signal indicative of an appropriate therapeutic treatment, and communicating to the patient the signal indicative of the appropriate therapeutic treatment. The patient may then administer to him or herself the prescribed therapeutic treatment indicated by the signal or instructions. In another embodiment, the signal indicative of the appropriate therapeutic treatment is communicated to an automated therapy unit to generate an automatic therapy regime.

a. Dynamic Prescription

In one embodiment, the automatic therapy regime is based upon a programmed dynamic prescription. "Dynamic prescription," as used herein, shall mean the information that is provided to the patient for therapy, including instructions on how to alter therapy based on changes in the patient's physiologic parameters. The instructions may be provided by a physician, practitioner, pharmacist, caregiver, automated server, database, etc. The information communicated to the patient includes authorizing new prescriptions for the patient and modifying the patient's medicinal dosage and schedule. The "dynamic prescription" information also includes communicating information which is not "prescribed" in its traditional sense, such as instructions to the patient to take bed rest, modify fluid intake, modify physical activity, modify nutrient intake, modify alcohol intake, perform a "pill count," measure additional physiological parameters, make a doctor's appointment, rush to the emergency room, call the paramedics, etc. One skilled in the art will understand that numerous other instructions may be beneficially provided to the patient predicated at least in part upon measurement of one or more physiological parameters in accordance with various embodiments of the present invention.

b. Therapy Delivery Units

According to another embodiment, a therapy delivery unit is provided, including but not limited to a system for releasing bioactive substances from implanted reservoir(s), a system for controlling electrical pacing of the heart, and cardiac assist devices including pumps, oxygenators, artificial hearts, cardiac restraining devices, ultrafiltration devices, intravascular and external counterpulsation devices, continuous positive airway pressure devices, and a host of related devices for treating cardiovascular conditions where knowledge of the left atrial pressure would be beneficial for optimal therapy delivery. Cardiac electrical pacing may be controlled in response to changes in physiological parameters in accordance with the present invention by, for example, AV delay optimization or any number of other methods, as are well known to one skilled in the art of cardiology.

According to one embodiment of the invention, the therapy delivery unit is implanted according to the methods described herein for the pressure transducer.

i. Drug Infusion

In one embodiment of the invention, a drug delivery unit is provided. In this embodiment, intravenous or subcutaneous, bolus or continuous infusion of drug from an implantable drug delivery unit can be triggered or regulated by the signal processing apparatus when certain predefined conditions are met. In one embodiment, automatic drug delivery or other therapeutic measure is used as a last resort "rescue mode" when the monitored physiological parameters indicate the patient's condition requires urgent therapeutic response. Typically, in "rescue mode", the patient's condition is not amenable to a change in oral medication dose (see "Dynamic Prescription"). Thus, in one embodiment, this invention includes both the dynamic prescription with patient signaling, and automated therapy via electrical stimulation, drug infusion, or other therapy delivery unit. Drugs that may be so administered include but are not limited to natriuretic peptides (e.g., Natricor), diuretics (e.g., furosimide), and inotropes (e.g., epinephrine, norepinephrine, dopamine, dobutamine, milrinone). In one embodiment, rescue mode emergency drug infusion, defibrillation, or other therapy is performed automatically based at least in part on signals indicative of the patient's condition derived from the one or more sensors of the invention. In another embodiment, rescue mode therapy is initiated by the present invention only after receiving doctor authorization to deliver the therapy. In one embodiment, doctor authorization is given by entering a password into the external patient signaling/communication module. This permits potentially dangerous emergency therapy to be delivered only after consultation with and authorization by a qualified healthcare professional.

In one embodiment, dosimetry for multiple drugs or other associated therapeutic devices is relayed based on parameter values as input to a parameter-driven prescription. In one embodiment, the system essentially replicates, in the home setting, the way inpatients are managed based on their doctor's standing orders in the Intensive Care Unit (ICU) of a hospital. In the ICU, nurses periodically look at real-time physiologic values from diagnostic catheters, and administer medications based on predetermined orders by the patient's attending physician. One embodiment of the present invention accomplishes the same thing. In one embodiment, wireless communications technology is integrated with diagnostic and treatment methods that are well established in cardiology. As such, the system is designed to be convenient and time-efficient for both the patient and his physician. The combination of monitoring key physiologic parameters and the patient's own physician's prescription drive a real-time feedback loop control system for maintaining homeostasis. Thus, in one embodiment, the system comprises an integrated patient management system tightly and directly linking implantable sensor diagnostics with pharmacologic and other therapies. As a result, this therapeutic approach enables better, more cost effective care, improves out-of-hospital time, and empowers patients to play a larger and more effective role in their own healthcare.

In one embodiment, a portable system for continuously or routinely monitoring one or more parameters indicative of the condition of a patient is provided. Depending upon changes in the indicated condition, the system determines, based on parameter-driven instructions from the patient's physician, a particular course of therapy. The course of therapy is designed to manage or correct, as much as possible, the patient's chronic condition. In one embodiment, the system communicates the course of therapy directly to the patient or to someone who assists the patient in the patient's daily care, such as, for example, but not limited to, a spouse, an aid, a visiting nurse, etc.

C. Telemetry

In one embodiment of the invention, one or more signals are communicated between the permanently implanted components of the system and a component of the system external to the patient's body. In one embodiment, signaling from the implanted to the external components is achieved by reflected impedance using radio frequency energy originating from the external device, and signaling from the external components to the internal components is achieved by frequency or amplitude shifting of radio frequency energy originating from the external device. Thus, in this embodiment, the current invention allows for telemetry of data from within the heart without transmitting radio frequency energy from the implanted device, advantageously resulting in significantly reduced power consumption compared to implants that perform telemetry by transmitting signals from within the body.

In another embodiment, signaling from the implanted to the external components is achieved through the metal housing of the implanted device using the method of Silvian (U.S. Pat. No. 6,301,504) incorporated by reference in its entirety herein.

In yet another embodiment, signaling from the implanted housing containing components of a CRM device is achieved via an antenna embedded within a dielectric around the periphery of the housing, as taught, for example, by Amundson et al. in U.S. Pat. No. 6,614,406, included herein by reference.

D. Power

In one embodiment of the invention, the implanted apparatus is powered by a battery located within an implanted housing, similar to that of a cardiac pacemaker, as is well known in the art of cardiac pacing. In another embodiment, the implanted apparatus is powered by an external power source through inductive, acoustical or RF coupling. In one embodiment, power is provided to the implanted device using 125 kHz emissions emitted from an electrical coil placed outside the body. In one embodiment power and data telemetry are provided by the same energy signal. In one embodiment of the system a second electrical coil is implanted inside the body at a location under the skin near the patient's collarbone, similar to the placement of the generator housing of an implantable pacemaker. In one embodiment, the implanted module includes an internal power source such as a battery, or it can be powered transcutaneously by induction of radio frequency current in an implanted wire coil connected to the module to charge an internal power storage device such as a capacitor.

E. Physical Location of System Components

In one embodiment of the present invention, the apparatus for diagnosing and treating cardiovascular disease is modular and consists of a plurality of modules. Each module contains hardware, and may contain one or more software programs. The component modules can be physically located in different places and their functions can differ dependent on the particular design of the modules. FIG. 4 shows one embodiment of the current invention, in which the first implantable module 5 of the apparatus is implanted within the patient. A patient advisory module 6 is located external to the patient's body and generally resides with the patient or his direct caregivers. A third module (not shown in FIG. 4) may reside with the physician. Each module performs multiple functions and some of the functions may be performed on multiple modules. In one embodiment, the modules consist of component sub-modules that perform a particular function, such as described above.

1. Leads

Although the pressure transducer in the embodiment produces an electrical signal indicative of pressures in its vicinity and, accordingly, an electrical lead is used to transmit the signals to the electronic circuitry, other types of pressure transducers may be used as well. For example, the pressure transducer and lead might comprise a tube filled with an incompressible fluid leading from the site in the body where the pressure is to be measured back to a transducer in another location. Signals in the form of pressures in the incompressible fluid indicate pressures at the site of interest, and those pressures are sensed by the transducer and utilized by the electronic circuitry in generating signals indicative of appropriate therapeutic treatments. Signals in other forms may be used as well and may be transmitted, for example, by fiber optic means, or by any other suitable electrical, electro-mechanical, mechanical, chemical, or other mode of signal transmission.

Moreover, although the signal lead in one embodiment is of an appropriate length so that the housing containing the electronic circuitry can be implanted in the region of the patient's shoulder, in alternative embodiments the lead may be of virtually any useful length, including zero. In one embodiment, an integrated unit is used in which the pressure transducer is disposed directly on the housing and the entire device is implanted inside or very near to the site at which pressure measurement is desired, for example the left atrium of the patient's heart.

II. SYSTEM OPERATION

A. Signal Processing

Figure 27:
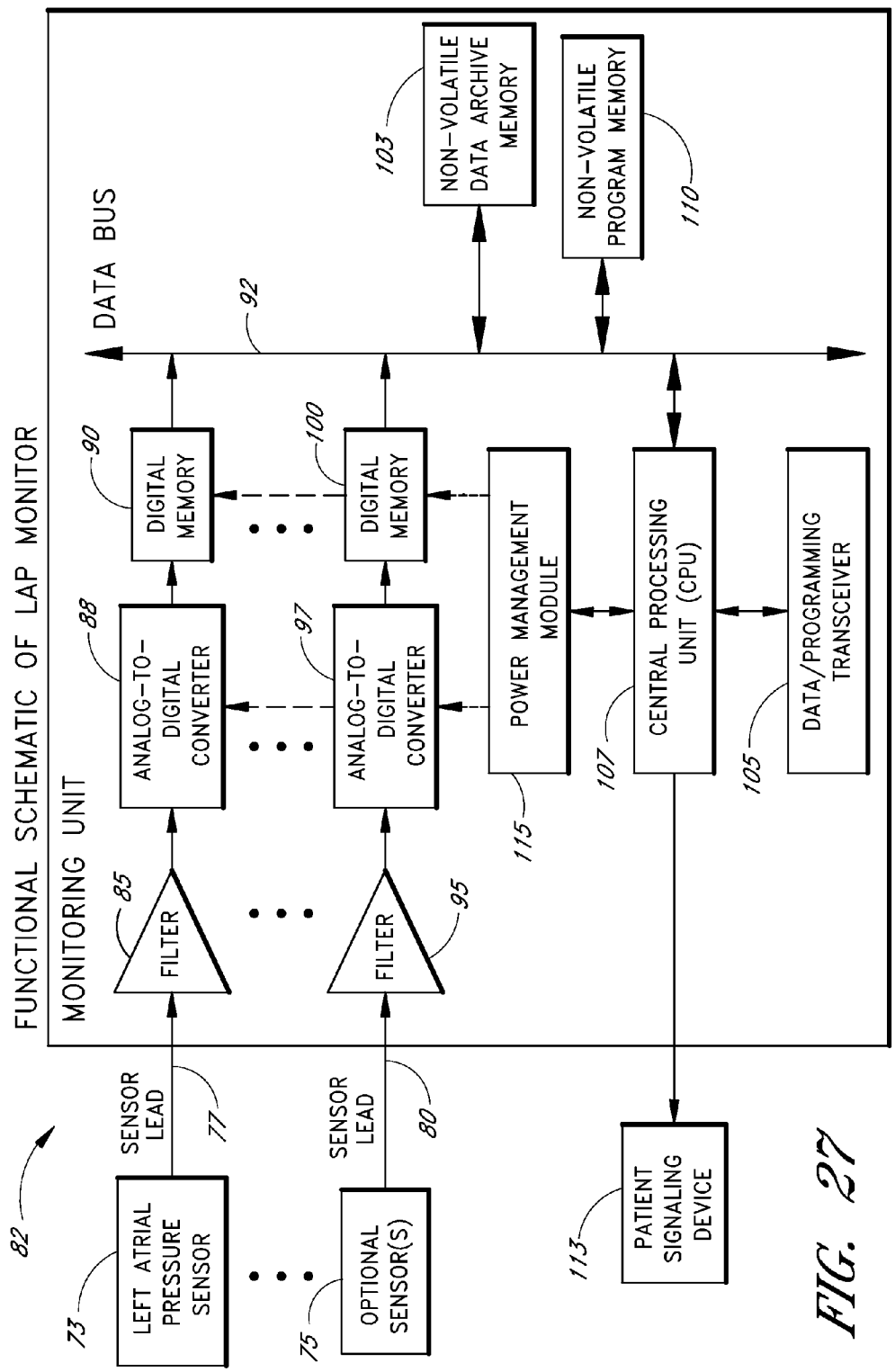
FIG. 27 is a schematic diagram depicting digital circuitry suitable for use in one embodiment of the invention.

FIG. 27 is a schematic diagram of operational circuitry that in one embodiment is located inside the housing 7 (not shown) and is suitable for use in accordance with one embodiment of the present invention. The apparatus depicted in FIG. 27 includes digital processors, but the same concept could also be implemented with analog circuitry, as is well known to those of skill in the art.

As described above, in one embodiment, the system of the invention includes a pressure transducer 73 permanently implanted to monitor fluid pressure within the left atrium of the patient's heart. Moreover, the system may include one or more additional sensors 75 configured to monitor pressure at a location outside the left atrium, or a different physical parameter inside the left atrium or elsewhere. For each sensor 73, 75, a sensor lead 77, 80 conveys signals from the sensor 73, 75 to a monitoring unit 82 disposed inside the housing of the unit. Alternatively, several sensors may be located in a compact sensor package or sensor module as, for example, illustrated in FIGS. 1, 2, 4, 22 and 23. In this case, the several sensors may share a single sensor lead for conveying signals from the sensors to the monitoring unit or a telemetry antenna. It should also be noted that the sensor lead connecting the pressure transducer to the monitoring apparatus might also be combined with or run parallel to another lead such as an electrical EKG sensor lead or a cardiac pacing lead, either of which might be placed in or near the left atrium.

In one embodiment, when the signal from the left atrial pressure transducer 73 enters the monitoring unit 82, the signal is first passed through a low-pass filter 85 to smooth the signal and reduce noise. The signal is then transmitted to an analog-to-digital converter 88, which transforms the signals into a stream of digital data values, which are in turn stored in digital memory 90. From the memory 90, the data values are transmitted to a data bus 92, along which they are transmitted to other components of the circuitry to be processed and archived. The stream of binary digital values may be immediately transmitted to a telemetry device external to the patient one bit at a time as they are generated from the most significant bit to the least significant bit by a successive approximation analog-to-digital converter. An additional filter 95, analog-to-digital converter 97, and digital memory area 100 may be provided as shown for each optional sensor 75 whenever such a sensor 75 is present. In another embodiment, several sensors share one analog-to-digital converter.

In one embodiment, the digital data on the data bus 92, are stored in a non-volatile data archive memory area 103. The archive 103 stores the data for later retrieval, for example, by a physician at the patient's next regularly scheduled office visit. The data may be retrieved, for example, by transcutaneous telemetry through a transceiver 105 incorporated into the unit. The same transceiver may serve as a route for transmission of signals into the unit, for example, for reprogramming the unit without explanting it from the patient. The physician may thereby develop, adjust, or refine operation of the unit, for example, as new therapies are developed or depending on the history and condition of any individual patient. By way of an additional example, reprogramming the implanted device could include changing the sampling frequency for digitizing the pressure, IEGM or other waveforms, or selecting which sensor data is to be monitored. Devices for transcutaneous signal transmission are known in the art in connection with pacemakers and implantable cardiac defibrillators (collectively known as cardiac rhythm management apparatus), and the transceiver used in the present invention may be generally similar to such known apparatus.

In one embodiment of the present invention, the digital data indicative of the pressure detected in the left atrium, as well as data corresponding to the other conditions detected by other sensors, where such are included, are transferred via the data bus 92 into a central processing unit 107, which processes the data based in part on algorithms and other data stored in non-volatile program memory 110. The central processing unit 107 then, based on the data and the results of the processing, sends an appropriate command to a patient signaling device 113, which sends a signal understandable by the patient and based upon which the patient may take appropriate action such as maintaining or changing the patient's drug regimen or contacting his or her physician.

Circuits or software for extracting relevant components from a pressure waveform are familiar to those skilled in the art. For example, a low pass filter element may be used to extract the long-term average, or "DC" component. In one embodiment, the outputs of overlapping low pass filters, one designed to include only frequencies lower than respiratory cycle frequencies, and the other designed to include respiratory but not cardiac cycle frequencies, are sampled at a fixed time in each cardiac cycle and subtracted to derive the respiratory component. In general, the respiratory contribution to the waveform is negative during inspiration and positive during expiration, with a mean contribution of zero. Thus, the long-term average of the pressure waveform is equal to the average of the cardiac component. The term of the long-term average is chosen to be long compared to the respiration rate but short compared to the rate of mean pressure change due to changes in a change in the patient's condition, so that slowly changing physiological information relevant to managing the patient's condition is not lost.

B. Signal Communication

In several embodiments of the invention, the patient signaling device 113 comprises a mechanical vibrator housed inside the housing of the system. In one embodiment, the vibrator delivers a small, harmless, but readily noticeable electrical shock to the patient. In some embodiments, a low power transmitter configured to transmit information transcutaneously to a remote receiver, which could include a display screen or other means for communicating instructions to the patient. In one embodiment, the system includes communication devices for communicating information back to a base location. These telecommunication devices and methods include, but are not limited to cellular or land-line telephone equipment or a device connected to the Internet, for communicating information back to a base location. In one embodiment, these telecommunication devices and methods are used to transmit information concerning the patient's condition back to a hospital or doctor's office, or to transmit information concerning the patient's prescription usage back to a pharmacy. In another embodiment, these telecommunication devices and methods may be used bidirectionally such that the physician, clinic, hospital, pharmacy, disease management service, database, etc., may modify patient instructions and dynamic prescriptions based on the information communicated from apparatus coupled to the patient.

In one embodiment, the signal processing and patient signaling components of the invention are combined into a patient advisory module, external to the patient's body. The patient advisory module further comprises a telemetry module to receive pressure and other physiological data from the implanted sensor system via wireless telemetry. This configuration has the advantage that the external device may be based in part on a general purpose computer such as a personal data assistant (PDA), allowing increased flexibility and complexity in signal processing, prescription algorithm processing, as well as providing telecommunications or other wire-based or wireless communications capability. Wireless communication platforms include, but are not limited to devices supporting 802.11b Wireless Networking (Wi-Fi) or the Bluetooth short range digital radio standard for wireless personal area networking.

An additional advantage of this configuration is that it provides essentially unlimited storage for digital physiological data from the patient, as well as for information on medications and other relevant information to help the patient and physician manage congestive heart failure.

Yet a further advantage of the externalized patient signaling device component is that a much richer and easier to use interface with the patient is facilitated using a display screen and/or audio communication with the patient. In one embodiment, a reminder function is incorporated in the external device such that the patient is prompted to initiate measurement just prior to scheduled medications or other therapy. The patient is then advised of the appropriate doses of medications and/or other therapies based on the measurements and his physician's dynamic prescription.

In one embodiment, the patient advisory module is external and serves as a treatment and medications record. In this use, the patient will be asked to verify which of the prescribed medications were taken and which were, for whatever reason, were skipped, thus creating a record of compliance with the dynamic management program. This function will permit the physician to better manage the patient and, additionally, will improve patient compliance. Yet another advantage of the externalized patient advisory module is that it can be easily integrated with a cellular telephone or PDA/cell phone combination, allowing automated telemetry of alerts and/or physiological data to a remote health care provider such as the patient's physician, hospital, nursing clinic, or monitoring service.

Apparatus as described herein may also be useful in helping patients comply with their medication schedule. In that case, the patient advisory module could be programmed to signal the patient each time the patient is to take medication, e.g., four times daily. This might be done via an audio or vibratory signal as described above. In versions of the apparatus where the patient signaling device includes apparatus for transmitting messages to a hand held device, tabletop display, or another remote device, written or visual instructions could be provided.

In one embodiment, apparatus generates spoken instructions, for example, synthesized speech or the actual recorded voice of the physician, to instruct the patient regarding exactly what medication is to be taken and when.

Where the system includes apparatus for communicating information back to a base location, e.g., the hospital, doctor's office, or a pharmacy, the system in one embodiment, tracks the doses remaining in each prescription and to reorder automatically as the remaining supply of any particular drug becomes low.

In one embodiment of this invention, the external device communicates with a personal computer (PC) in the doctor's office either directly when the patient is present for an office visit, or via electronic communications, including, but not limited to, a telephone modem or the internet. During this communication, data is uploaded from the external device to the PC, including the records of physiological measurements, symptoms, and medication compliance, as well as information regarding the operation and calibration of the implanted device. Software on the PC displays the patient information, and the doctor enters a new dynamic prescription or edits the existing one. The PC then downloads the new or edited dynamic prescription to the external device. Re-calibration of the pressure transducer in the external device may be performed relative to a reference manometer in the physician's office.

In one embodiment, the physician's PC maintains a database of all the patients under medical management by the physician using the device of this invention. The database includes the patients identifying, demographic, and medical information, the implantable device's unique identification number. For each patient, the database maintains a record of all data uploaded from the external device, device calibration records, patient dynamic prescription records, and compliance records.

In one embodiment, data stored in the external patient advisory module is uploaded to the physician's PC at the time of the patient's regular office visit. The external device is placed in a data interface cradle connected to the PC, and the data is transferred. In one embodiment of the data transfer, the external device is a modified personal data assistant such as a PALM PILOT™ (Palm Computing, Inc.), and the data interface cradle is the cradle used by such PDA devices for data synchronization with a personal computer.

In another embodiment, the data from the external device is uploaded to the physician PC via the Internet, telephone, or cellular telephone network. In this case, the data may be uploaded at regular intervals, or whenever the patient or physician determines there is a need for physician review of the patient's management.

The prescription editor is a software program on the physician's PC that allows the physician to create, view, and modify the dynamic prescription for each patient. The dynamic prescription may consist of sets of prescribed treatments depending on the values of one or more physiological measurements, and/or patient symptoms, and/or changes and/or rates of change of measurements or symptoms (collectively, input parameters). A prescription editor allows the physician to define thresholds for each input parameter and to define the combination of treatments to be administered for each possible combination of input parameters. In one embodiment, the prescription editor has a graphical user interface that displays the possible combinations of input parameter ranges and the corresponding treatments in a way that the physician can clearly see that all possibilities have been defined according to his intended management of the patient. In another embodiment, the prescription editor provides for the entry and/or editing by the physician of a set of rules relating data collected from the patient and treatments to be administered or instructions to be followed by the patient.

In one embodiment, the revised dynamic prescription and/or calibration data is downloaded from the physician's PC to the external device in the same way that data is uploaded from the external device to the physician's PC. Such downloading and/or uploading may occur, for example, by connecting the patient's external device to the physician's PC by direct hardwire connection (e.g. serial interface), by wireless connection, or via the Internet. In one embodiment, a unique identification number from the external device is used to verify the correct match between the prescription and the patient. This unique identification number is obtained by the external device from the implanted device, which has a unique identification number programmed into its integrated processor chip at the time of manufacture. In one embodiment, a 27-bit unique identification code is permanently programmed into the implanted device at the time of manufacture. This identification number is sent along with data communicated from the implanted device to the external device to uniquely identify the implanted device to the external device software.

C. Power Management

In one embodiment, the circuitry of the invention may also include a power management module 115 configured to power down certain components of the system between times when those components are in use. Such components include, but are not limited to, analog-to-digital converters 88, 97, digital memories 90, 100, and central processing unit 107, as shown in FIG. 27. This helps to conserve battery power and thereby extend the useful life of the device so that it can remain operational inside the patient's body for extended periods between maintenance or replacement. Other circuitry and signaling modes may be devised by one skilled in the art.

In one embodiment, the implanted pressure monitor operates on transmitted power from outside the body, eliminating the need for an implanted battery. This approach is particularly well suited when periodic, as opposed to continuous, monitoring is required. In one embodiment, 125-kHz radio-frequency energy is transmitted from an external coil, through the patient's skin, and received by an implanted antenna coil connected to the electronics package of the implantable pressure monitor, as described above. The signal in the antenna coil is rectified and used to charge a capacitor, which in turn powers the measurement electronics. Low power telemetry of the measured data is performed by varying the impedance of the antenna coil circuit. In still another embodiment, the coil antenna is incorporated into or immediately adjacent to the pressure sensor within the heart.

III. DIGITAL PACEMAKER LEAD AND ELECTRODE

A. Overview of Pacemaker Technology

Figure 30:
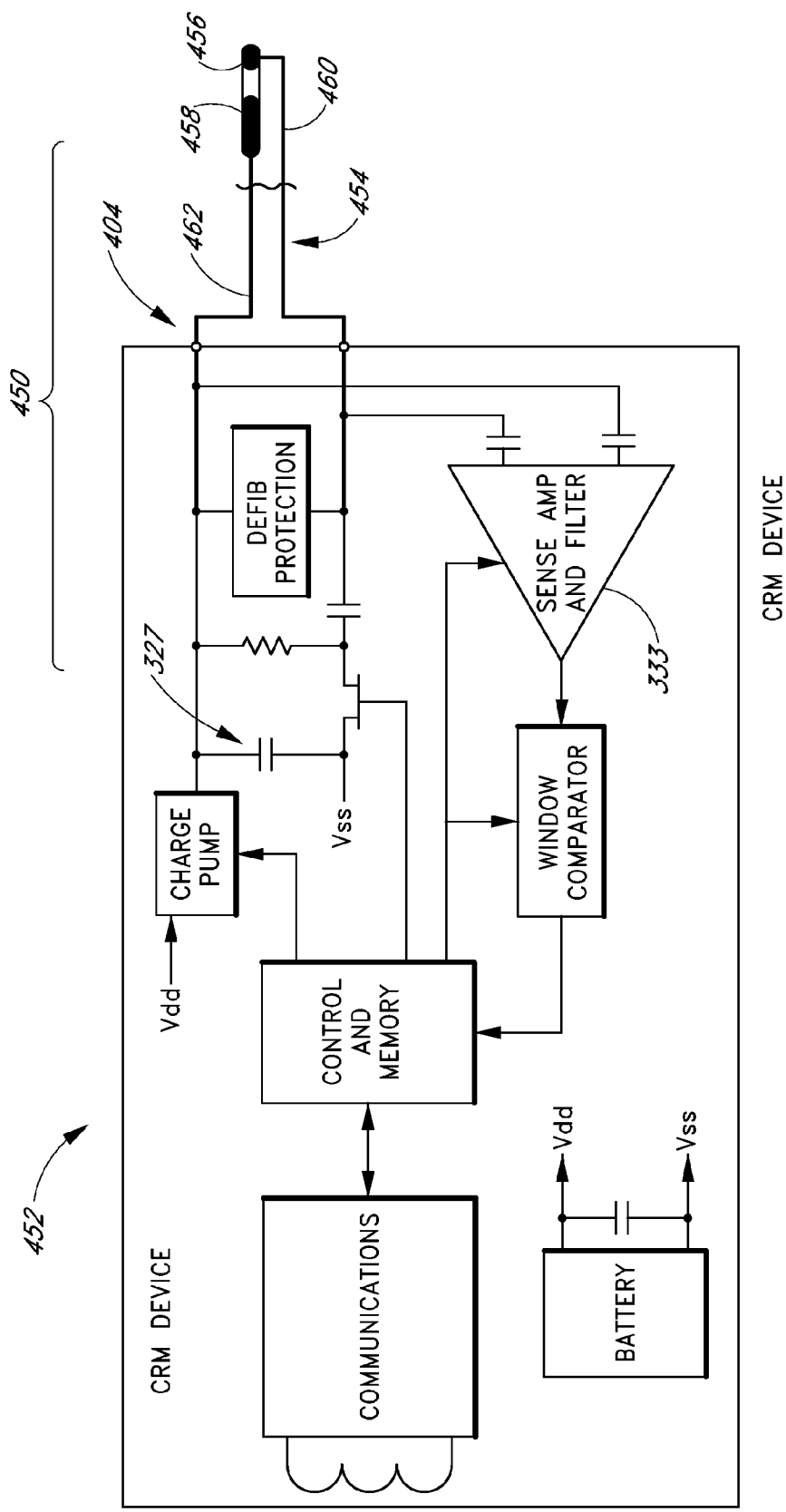
FIG. 30 is a pacemaker using an analog lead.

As described above, in several embodiments a cardiac rhythm management apparatus includes a pacemaker. In one embodiment, the cardiac rhythm management apparatus includes a conventional "analog electrode." A conventional pacemaker is a pacemaker where an electrical stimulus is generated in a proximally located housing, or generator unit (which in one embodiment is implanted subcutaneously near the patient's shoulder), and travels through an electrical conductor in a pacemaker lead to a distal electrode, where it is delivered to a location within the patient's heart, as described in greater detail above. In addition, in a conventional pacemaker, sensed signals from the electrode are conducted in analog form from the heart to the proximal housing, where they are amplified and used to control pacing. FIG. 30, described in detail below, illustrates one embodiment of an analog pacemaker.

Alternatively, in another embodiment, the cardiac rhythm management apparatus includes a "digital electrode." In one embodiment, as used herein, a digital pacemaker shall be given its ordinary meaning and shall also mean a pacemaker in which digital signals, including energy pulses, are communicated between the proximal housing, or generator unit, and a distal module. In one embodiment, the distal module comprises a digital electrode module, as described below. In another embodiment, the distal module comprises both a digital electrode and a sensor package or module as described above with reference to FIG. 22 and FIG. 23. In one digital pacemaker embodiment, the digital signals include control signals to control the transfer of energy stored in the proximal housing to an energy storage device in the distal module. Energy pulses are transmitted from the proximal housing to the distal module, where the energy is stored in the distal module until delivery to the patient's heart. In another embodiment, the digital signals include sensor signals that are transmitted from the distal module to the proximal housing, from which they may be telemetered to an external device, such as a patient signaling device, as described in greater detail above. As described in greater detail below with respect to FIG. 31, the distal module may comprise a sensor housing that includes electrodes, sensors, and electronic circuits. In other embodiments, as described in greater detail below, the distal electrode may include only a single electrode and electronic circuits.

B. Conventional Pacemaker Technology

FIG. 30 illustrates one embodiment of a conventional pacemaker 450 (sometimes referred to herein as an analog pacemaker) in accordance with one embodiment of the present invention. The conventional pacemaker 450 includes a generator 452, lead 454, first and second electrodes 456, 458. The first and second electrodes 456, 458 are electrically coupled to the generator 452 with first and second conductors 460, 462, which travel at least partially within the lead 454.

As described above, the generator 452 is generally implanted subcutaneously near a patient's shoulder, and provides an electrical stimulus across the electrodes 456, 458, which is in contact with the medical patient's heart. The electrode in contact with the heart, e.g., the first electrode 456, which provides such stimulation, is also referred to as a pacing electrode 456. The second electrode 458 may or may not be in contact with the patient's heart, and is also referred to as the indifferent electrode 458. In one embodiment, the indifferent electrode 458 is not located within the patient's heart.

In one embodiment, a stimulating electrical pulse is produced by the generator 452 and travels through a conductor 460 located within the electrically insulated lead 454, to the pacing electrode 456, where the stimulating pulse is delivered to a location within the patient's heart. In one embodiment, the pacing electrode 456 is placed in the apex of the right ventricle of the patient's heart.

In one embodiment, the lead 454 is a bipolar lead, such as illustrated in FIG. 30. As shown in FIG. 30, the bipolar lead 454 includes two conductors 460, 462. One conductor is connected to a pacing electrode 456 located at the lead's 454 distal end. The other conductor 462 is connected to an indifferent electrode 458, located proximal the distal end of the lead 454. In one embodiment, the indifferent electrode 458 is a ring electrode, although other types of electrodes may be used, as is well known to those of skill in the art.

In another embodiment (not illustrated), the lead is a unipolar lead, which includes only one electrode, that is located at the lead's distal end. In such embodiment, the indifferent electrode is provided at some other portion of the lead, as part of the metallic housing of the generator, or coupled to a second lead. In one embodiment, the unipolar lead has a single conductor which couples the generator to a single pacing electrode located at the lead's distal end.

a. Sensing Functionality

Referring again to FIG. 30, the pacemaker 450 is able to measure or sense the natural electrical activity within the heart through a sensing electrode. The sensing electrode is incorporated with the lead 454. As illustrated, the pacing electrode 456 is also able to operate as a sensing electrode 456. By sensing the electrical activity within the heart, the pacemaker 450 is able to adjust, withhold, or apply a stimulation in response to the sensed electrophysiological condition.

There are limitations, however, to using the same electrode for pacemaker sensing and pacing. For example, sensed electrical signals are generally smaller in magnitude than pacing pulses, and are generally amplified by an amplifier 330 before being processed by the pacemaker generator. In addition, an ideal sensing electrode should have a large surface area, while an ideal pacing electrode should have a small surface area to minimize power requirements. In addition, after pacing pulses are delivered, there is a time interval, such as a delay interval, that occurs before sensing may be performed with the single electrode. Such a time interval is provided generally because the relatively high pacing pulse voltage persists for some time on the lead and conductor due to lead capacitance. Potentially important electrophysiological data may be lost during this time interval. One example of such data is the tissue's response to a pacing pulse, known as the "evoked response." Detection of evoked responses can be used by the pacemaker to determine whether capture has or has not occurred, allowing the pacemaker to adjust to changing threshold levels.

The limitations and disadvantages of a single electrode pacemaker may be overcome by providing a lead with separate sensing and pacing electrodes. However, such lead would generally require separate sensing and pacing conductors as well, which disadvantageously increases lead diameter, and increases the number of connectors required.

b. Multiple Conductor Leads

In one embodiment, the pacemaker lead also includes one or more physiological sensors in addition to the electrode or electrodes. In such embodiment, the lead provides the electrical conductors and connections required to power the sensor(s), and to conduct the sensor signal(s) to the pacemaker generator. However, increasing the number of electrical conductors within the lead disadvantageously increases the diameter and decreases the flexibility of the lead, and/or requires the conductor diameters to become smaller. Smaller conductors are generally weaker, break more frequently over time, and are less reliable. Smaller diameter conductors also generally have higher electrical resistance, which results in an undesirable voltage drop between the generator and pacing electrode(s). Increasing the number of conductors within the lead also increases the complexity of the connector that couples the lead to the pacemaker generator.

Multiplexing may be used to switch the function of conductors between pacing and sensing, in order to reduce the number of conductors within the pacemaker lead. Such techniques are taught by Barcel in U.S. Pat. No. 5,275,171 and Weijand, et al. in U.S. Pat. No. 5,843,135, both incorporated by reference herein. Although such methods may reduce the number of connectors within a pacemaker lead, they do so by sharing the remaining conductors between several analog signals, including the pacing stimulus. Such analog signals may contain electrical noise due to muscular activity, radiofrequency (RF) interference, and potential cross-talk between physiological and electrical sensing signals. In addition, lead conductors that carry analog signals act as antennas for RF noise and for induced voltages from RF energy sources, such as magnetic resonance imaging (MRI) scanners. RF noise on the sense conductor may cause erroneous pacing, even with sophisticated digitally filtering algorithms as are commonly used by and known to those of skill in the art. In addition, MRI scanning is contra-indicated for patients with implantable cardiac pacemakers because of the risks of inducing voltages from such procedures.

The digital electrode embodiments of the present invention solve these and other problems, as described in greater detail below.

C. Digital Electrode Technology

Figure 31:
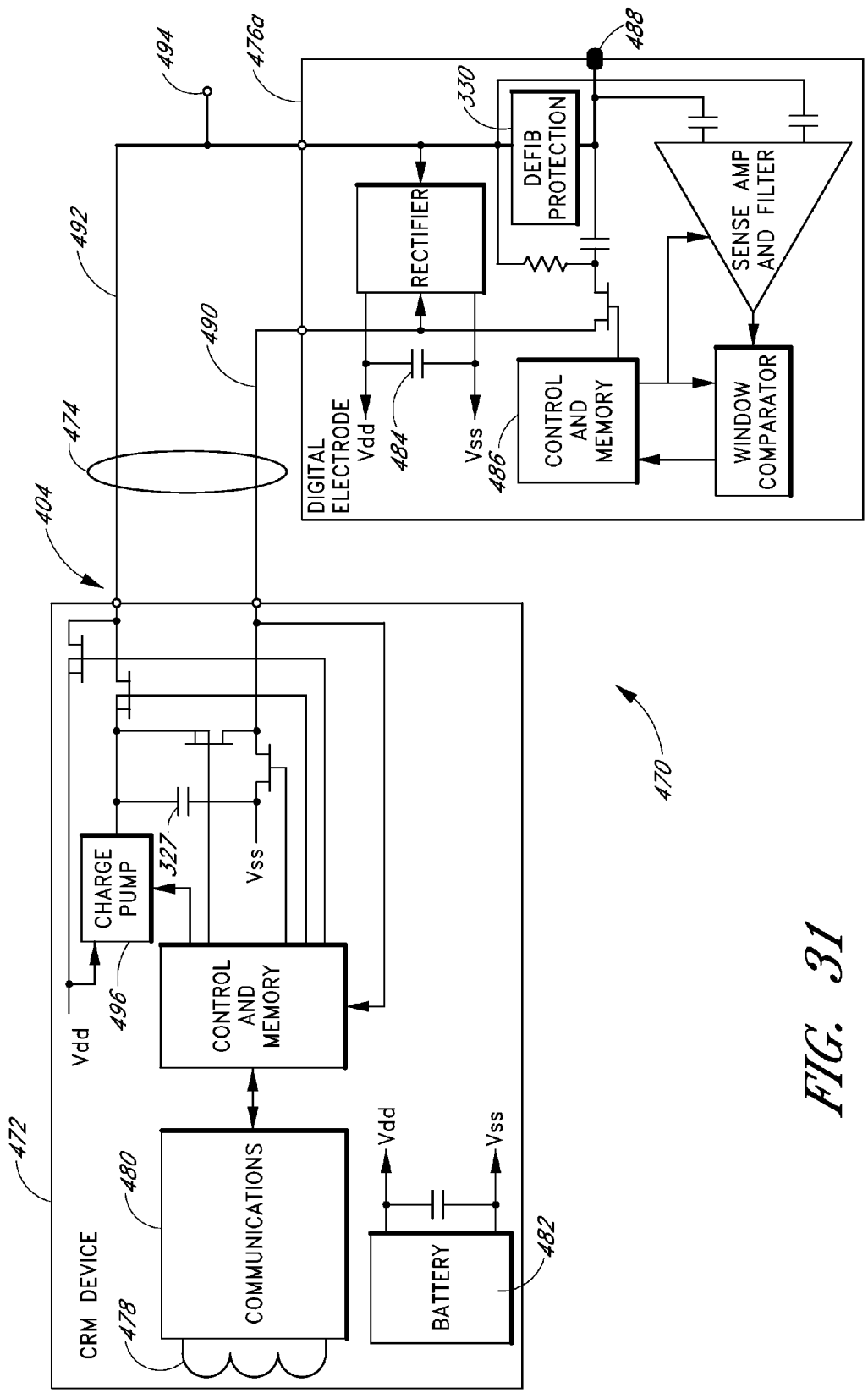
FIG. 31 is a pacemaker with a digital electrode comprising sense amplifier, pacing/sensing electrode, and defibrillation protection in accordance with one embodiment of the present invention.

FIG. 31 illustrates a digital pacemaker in accordance with one embodiment of the present invention. Digital pacemaker 470 includes a proximal housing 472, a lead 474, and a distal module 476. In one embodiment, the proximal housing 472 is approximately the same size and shape of the analog pacemaker 450 generator 452, as illustrated in FIG. 30. In another embodiment, the proximal housing 472 is smaller than the generator 452.

In one embodiment, the proximal housing 472 includes an antenna 478, telemetry module 480, and energy storage device 482, charge pump 496 and pacing capacitor 327. In one embodiment, the distal housing 476 includes an energy storage device 484, a control module 486, and an electrode and sensor module 488. (In one embodiment, the distal housing 476 is the sensor package or module 200 shown in FIG. 22 and FIG. 23.) A lead 474 couples the proximal housing 472 to the distal housing 476, and includes first and second conductors 490, 492 to facilitate communication therebetween. In one embodiment, the lead 474 comprises an indifferent electrode 494 in electrical communication with lead conductor 492.

The antenna 478 and telemetry module 480 are used to communicate with an external device, such as a programmer, or patient advisory module, as described in greater detail above. In addition, in another embodiment, the antenna 478 and telemetry module 480 are used to receive energy from an external device and store that energy within energy storage device 482. In another embodiment, energy received from an external device is delivered through the antenna 478 and telemetry module 480 directly to the distal module 476, where it is stored in energy storage device 484. Energy storage device 482, 484 may include a battery, capacitor, or other electrical energy storage circuit or device as is well known to those of skill in the art.

In one embodiment, the control module 486 includes a microprocessor, microcontroller, or discrete digital and analog control circuits, as are well known to those of skill in the art. The control module 486 controls the transfer of stored energy from the proximal energy storage device 482 to the distal energy storage device 484, as well as the transfer of stored energy from the distal energy storage device 484 to the patient's heart via the electrodes of the electrode and sensor module 488. In one embodiment, energy is transferred from the proximal housing 472 to the distal module 476 according to the digital communications protocol and timing diagram described above with respect to FIG. 24. In such embodiment, the proximal housing 472 includes a CRM Module, and the distal module includes an LAP Module (as described above). In another embodiment, the distal module 476 includes the device 320, POD 320, or sensor module 320, as described in greater detail above, with respect to FIG. 25.

In one embodiment, the electrode and sensor module 488 includes at least one electrode as described above. In one embodiment, the electrode and sensor module 488 includes an electrode for providing pacing stimuli to the heart, and a separate sensing electrode (not shown) to measure and/or sense the electrical activity of the heart. In another embodiment, the electrode and sensor module 488 includes at least one physiological sensor for measuring a physiological parameter of the heart. In one embodiment, the physiological sensor is a pressure sensor, thermometer, ultrasonic sound emitter, ultrasonic sound receiver, IEGM sensor and/or any other sensor as described above, or as known to those of skill in the art. In one embodiment, the physiological parameter is a pressure indicative of the pressure within the left atrium of the heart, a temperature indicative of the patient's core temperature, an acoustic signal indicative of a volume of a chamber of the heart, or an electrical signal indicative of the pulsing and/or beating of the patient's heart.

In one embodiment, the electrode and sensor module 488 includes a full Wheatstone bridge strain gauge, coupled to four conductors (not shown). In another embodiment, the electrode and sensor module 488 includes a half-bridge strain gauge, coupled to three conductors (not shown). Even in such embodiments, only two conductors 490, 492 extend through the lead 474 to the proximal housing 472.

FIG. 32 illustrates another configuration of a CRM device with a digital electrode according to the present invention. This embodiment is similar to that shown in FIG. 31, except that the charge pump 496 and pacing capacitor 327 are now located within the digital electrode housing 476 rather than the proximal housing 472.

In a conventional pacemaker, and in the embodiment of FIG. 31, the pacing pulse charge is first stored on a capacitor 327 in the proximal housing, and is then applied to the pacing electrode via the lead 474. In such embodiment, lead 474 resistance, which in one embodiment is as high as 150 Ohms, reduces the voltage applied to the tissue during pacing, requiring capacitor 327 to be charged to a higher voltage to compensate. In the embodiment of FIG. 32, the pacing capacitor 327 is located in the distal module 476, so the pacing voltage is applied directly to the pacing electrode 488, without passing through the lead resistance.

In one embodiment, the electrical components in the proximal housing 472 operate at a voltage lower than that required for pacing, and are fabricated with 0.12 µm CMOS technology. In such embodiment, the size and power consumption of the proximal housing 472 is reduced. In another embodiment, the electrical components within the distal module 476 are fabricated with 0.5 µm CMOS technology in order to accommodate the greater pacing voltages not found, generated or transmitted to or from the proximal housing 472. Other semiconductor manufacturing techniques and line-widths may be utilized, as is well known to those of skill in the art.

In one embodiment, sensor signals are processed by the control module 486 within the distal module 476, which is generally implanted within the patient's heart. By sensing and processing within the heart (and not communicating the sensed signal through a lead to a proximal housing for processing), susceptibility to noise is essentially eliminated.

In another embodiment, separate sensing and pacing electrodes are provided. By providing separate sensing and pacing electrodes, each can be optimized in shape, dimension, area, contact area with tissue, and/or materials. For example, in one embodiment, a pacing electrode has a small surface area to reduce the voltage required for pacing, and the sensing electrode has a large surface area to minimize impedance, or resistance. One embodiment of separate, optimized sensing and pacing electrodes is illustrated and described with reference to FIG. 22 and FIG. 23. In another embodiment, additional sensors, sensing and pacing electrodes are provided without increasing the number of conductors traveling through the lead 474.

In one embodiment, the electrode and sensor module 488 includes a pressure sensor and a pressure sensor lead (not shown). The pressure sensor lead extends from the distal module 476 to the pressure sensor, which in one embodiment is implanted within a wall of the heart. In such embodiment, the pressure sensor includes a housing which may be used as an electrode for pacing, sensing, or for delivering defibrillation stimuli. In one embodiment, the pressure sensor lead provides pacing or defibrillation stimuli to the pressure sensor housing, which acts as an electrode for pacing or defibrillation.

Figure 33:
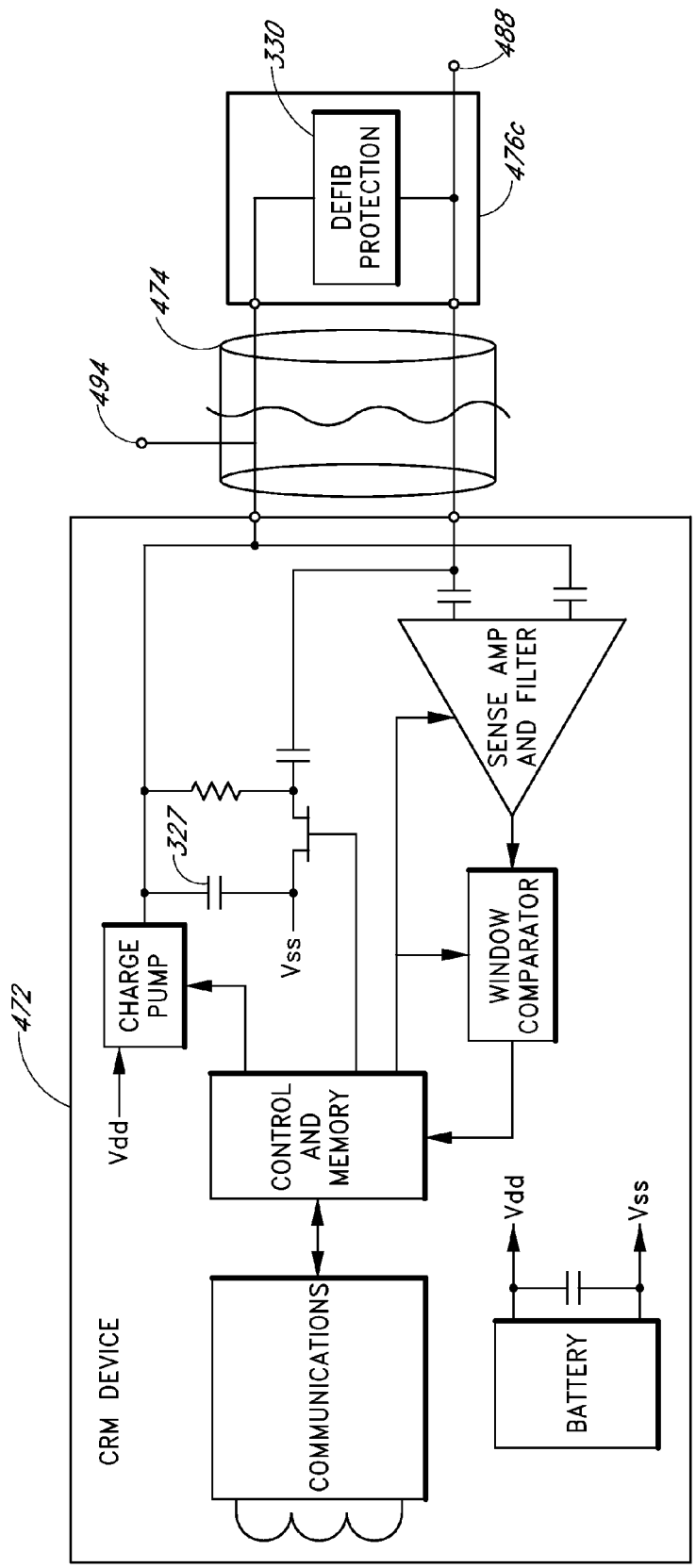
FIG. 33 is a pacemaker in accordance with one embodiment of the present invention, in which the defibrillation protection is provided within the digital electrode housing.

In several embodiments, the distal electrode module comprises the defibrillation protection circuitry 330, as shown for example in FIGS. 31, 32, and 33. Referring now to FIG. 33, a CRM device is shown comprising a proximal housing 472, a lead 474, and a distal electrode module 476, in which the defibrillation protection is located in the distal electrode module. This has the advantage that the conduction path from the pacing electrode 488 to the indifferent electrode 494 (shown in bold lines) is very short, and is almost entirely within the distal electrode housing. This may be compared to the conduction path in the prior art CRM device (shown in bold lines in FIG. 30), which runs the length of the lead from the pacing electrode all the way back to the proximal housing. This aspect of the present invention reduces the effect of induced voltages due to magnetic resonance imaging. In another embodiment, the housing of the distal module 476 acts an the indifferent electrode 494, and the electrode 488 is attached to a conductor that extends a distance from the distal module 476.

D. Digital Defibrillation

In another embodiment, a digital defibrillator includes an implantable heart monitor and a defibrillator, as described in greater detail above. In another embodiment, the implantable heart monitor includes any of the implantable heart monitors described above. The digital defibrillator provides power to the monitor, and it provides signaling for atrial and/or ventricular defibrillation, pacing, and sensing. In addition, the digital defibrillator includes a physiological sensor module that provides measurement data to a memory within a proximal housing. The digital defibrillator also allows the physiological sensor module to be programmed by an external device, such as a patient signaling module, as described in greater detail above.

E. Digital Communication

Referring back to FIG. 24, there is provided one illustration of a digital communication protocol over a two-conductor lead between a proximal housing and a distal module. In one embodiment the digital communication protocol is implemented in a digital pacemaker, and in another embodiment, the digital communication protocol is implemented in a digital defibrillator. Each power pulse-to-power pulse interval illustrated in FIG. 24 defines a frame of information over a particular time span. Each frame is further divided or segmented into a number of distinct sub-frame intervals. In one embodiment, each sub-frame interval is used to implement a defined function.

In one sub-frame interval a power pulse is delivered from a proximal housing to a distal module to charge the energy storage device, or power supply of the distal module. As described above, the distal module is generally located at the distal end of a lead which is coupled to a proximal housing at the lead's proximal end. In one embodiment, the power pulse is provided in the first interval of the frame, and it defines the end of one frame, and the beginning of the next frame. In one embodiment, the power pulses are generated at a particular frequency determined by a control module (such as control module 486 of the digital pacemaker 470 illustrated in FIG. 31). The frequency is used by the control module and a sensor module to adjust an internal RC or current source clock to synchronize operation between the measurement components and sensors of the distal module, and the defibrillator and/or pacing components of the digital defibrillator and/or pacemaker.

In one embodiment, data transmission intervals are defined between power pulse intervals. In one embodiment, a data transmission interval signals the defibrillator or pacemaker to provide an electrical stimulus, such as an electrical pulse to the electrode coupled to the patient's heart. In another embodiment, the data transmission interval commands a change in operation mode of a measurement or sensor module. In one embodiment, the data transmission interval includes a download interval, where data, including digitized data from a sensor is transmitted from the distal module to components, such as a memory device, or telemetry module, within the proximal housing.

In another embodiment, the data transmission interval includes an upload interval, during which information, commands, or data from the proximal housing is communicated to a distal module. In one embodiment, the proximal housing includes a measurement module, such as a POD or Heart-POD™ as described in greater detail above, and the distal module includes a defibrillator. In one embodiment, information communicated during the upload interval includes measurement data and/or status information regarding the current mode of operation of the measurement module, or a trigger signal that indicates that a sensed signal has been detected. In one embodiment, the type of data is conditional, depending, for example, on whether a programming mode change was called for in the previous download interval. In one embodiment, if a programming mode change was called for in the previous download interval, the upload interval data provides status information indicating whether the mode change was successful.

In one embodiment, the download and upload intervals are subdivided into data words, each containing a predefined number of bits, so that multiple pieces of information are communicated in each interval or word. For example, in one embodiment, the download interval includes a pacing pulse trigger bit followed by one or more programming bits. In another embodiment, the upload interval includes a sensing bit which is set if an R-wave and/or a P-wave of the internal electrocardiogram is sensed by the measurement module. The upload interval also includes NP bits of pressure data and NT bits of temperature data. In another embodiment, checksum bits are provided as well to guard against data transmission errors.

IV. EXAMPLES OF SYSTEM APPLICATION

A. Example 1

Exemplary modes of operation for an embodiment of the system of the invention are described as follows. The following Example illustrates various embodiments of the present invention and is not intended in any way to limit the invention.

In one embodiment, the system is programmed to power up once per hour to measure the left atrial pressure and other conditions as dictated by the configuration of the particular system and any other sensors that might be present. Left atrial pressure measurements are taken at a 20-Hertz sampling rate for sixty seconds, yielding 1200 data values reflective of the fluid pressure within the left atrium. The central processing unit then computes the mean left atrial pressure based on the stored values. Then, if the mean pressure is above a threshold value predetermined by the patient's physician, the central processing unit causes an appropriate communication to be sent to the patient via the patient signaling device.

A set of coded communications to the patient can be devised by the treating physician and encoded into the device either at the time of implantation or after implantation by transcutaneous programming using data transmission into the non-volatile program memory 110 via the transceiver 105. For example, assume that the physician has determined that a particular patient's mean left atrial pressure can be controlled at between 15 and 20 mm Hg under optimal drug therapy. This optimal drug therapy might have been found to comprise a drug regimen including 5 milligrams (mg) of Lisinopril, 40 mg of Lasix, 20 milliequivalents (mEq) of potassium chloride, 0.25 mg of Digoxin, and 25 mg of Carvedilol, all taken once per day.

The patient is implanted with the device and the device is programmed as follows. The device includes a pressure transducer implanted across the atrial septum such that the transducer responds to the difference in pressure between the right and left atria. This differential pressure is independent of changes in atmospheric pressure, and in most circumstances is well correlated with, and thus indicative of, the left atrial pressure. The device's programming provides for four possible "alert levels" that are specified according to mean differential atrial pressure detected by the transducer and computed in the central processing unit, and that the patient signaling device is a mechanical vibrator capable of producing pulsed vibrations readily discernable by the patient.

At predetermined intervals, for example, hourly, daily, weekly, monthly, 3-4 times per day, or in response to a detected event, in response to a symptom, or in response to an instruction, the device measures the patient's mean left arterial pressure as described above, and determines the appropriate alert level for communication to the patient according to programming specified by the physician. For example, a mean left atrial pressure of less than 15 mm Hg could be indicative of some degree of over-medication and would correspond to alert level one. A pressure between 15 and 20 mm Hg would indicate optimal therapy and correspond to alert level two. A pressure between 20 and 30 mm Hg would indicate mild under-treatment or mild worsening in the patient's condition, and would correspond to alert level three. Finally, a mean left atrial pressure above 30 mm Hg would indicate a severe worsening in the patient's condition, and would correspond to alert level four.

When the proper alert level is determined, the device sends a two-second vibrating pulse to notify the patient that the device is about to communicate an alert level through a sequence of further vibrations. A few seconds later, a sequence of one to four relatively short (one second) vibratory pulses, the number corresponding to the applicable alert level, are made by the device and felt by the patient. The patient can easily count the pulses to determine the alert level, then continue or modify his own therapy with reference to a chart or other instructions prepared for him by the physician.

For example, two pulses corresponds to alert level two, an optimal or near optimal condition for that particular patient. In that case, the doctor's instructions tell the patient to continue his or her therapy exactly as before. The signal for alert level two is given once every 24 hours, at a fixed time each day. This serves mainly to reassure the patient that the device is working and all is well with his therapy, and to encourage the patient to keep taking the medication on a regular schedule.

One pulse, in contrast, corresponds to alert level one, and most likely some degree of recent over-medication. The doctor's orders then notify the patient to reduce or omit certain parts of his therapy until the return of alert level two. For example, the doctor's instructions might tell the patient temporarily to stop taking Lasix, and to halve the dosage of Lisinopril to 2.5 mg per day. The coded signal is given to the patient once every twelve hours until the return of the alert level two condition.

Three pulses indicates alert level three, a condition of mild worsening in the patient's condition. Accordingly, the doctor's instructions notify the patient to increase the diuretic components of his therapy until alert level two returned. For example, the patient might be instructed to add to his to his normal doses an additional 80 mg of Lasix, twice daily, and 30 mEq of potassium chloride, also twice daily. The level three alert signal would be given every four hours until the patient's condition returned to alert level two.

Four pulses indicates alert level four, indicating a serious deterioration in the patient's condition. In this case, the patient is instructed to contact his physician and to increase his doses of diuretics, add a vasodilator, and discontinue the beta-blocker. For example, the patient might be instructed to add to his therapy an additional 80 mg of Lasix, twice daily, an additional 30 mEq of potassium chloride, twice daily, 60 mg of Imdur, twice daily, and to stop taking the beta-blocker, Carvedilol. The signal corresponding to alert level four would be given every two hours, or until the physician was able to intervene directly.

B. Example 2

In one embodiment, the system is configured as an externally powered implantable device with a sensor implanted in the intra-atrial septum. The pressure transducer of the sensor is exposed to the pressure in the left atrium. In one embodiment, the sensor is anchored in the septum such that the pressure transducer is substantially flush with the left atrial wall in fluid contact with blood in the left atrium. In another embodiment, the anchor is designed such that the pressure sensor extends a predetermined distance into the left atrium. In both these embodiments, the pressure sensor package is located in the septum with its proximal end extending back into the right atrium. A flexible lead extends from the proximal end of the sensor package back through the right atrium, into the superior vena cava, up to a subclavian vein, and out through the wall of the subclavian vein, terminating at an antenna coil assembly located in a subcutaneous pocket near the patient's clavicle, similar to a pacemaker generator housing.

The temperature at the site of the sensor and an internal electrocardiogram (IEGM) are also detected by the sensor. A digital signal is communicated to an external telemetry device via an antenna coil implanted under the patient's skin and connected to the sensor by a flexible lead. The sensor is powered by radio frequency energy received by the implanted coil from an external coil connected to the external telemetry device. The external telemetry device forms part of an external patient advisory module, that also includes a battery power source, a signal processor, and a patient signaling device that consists of a personal data assistant (PDA) with a display screen and software for communicating with the patient.

The external patient advisory module is programmed to alert the patient at times determined by the physician, preferably at the times the patient is scheduled to take prescribed medications, typically one to three times per day. In one embodiment, the alert consists of an audible alarm and the appearance of a written message on the graphical interface of the patient-signaling device. The message instructs the patient to perform a "heart check," that is to obtain physiological measurements from the implanted device. Instructions to the patient may include instructions to establish certain standard conditions, such as sitting quietly in a chair, prior to beginning the measurements. The patient is instructed to place the external telemetry/power coil over the implanted antenna coil, then to press a button to initiate the measurement sequence. Once the patient presses the button, the external device begins emits energy via the external coil to power and communicate with the implanted device. In one embodiment the external device emits an audible signal while communication is being established, then emits a second audible signal distinct from the first when communication has been established and while the measurement is taking place. Once the measurement is concluded, typically after 5 to 20 seconds, a third audible signal, distinct from the first two, is emitted to signal the patient that the measurement is complete.

In one embodiment, the external device will further instruct the patient, using its graphical interface, to enter additional information relevant to the patient's condition, such as weight, peripheral blood pressure, and symptoms. The signal processing apparatus of the external device then compares the measured physiological parameters from the implanted device, together with information entered by the patient, with ranges and limits corresponding to different therapeutic actions as predetermined by the physician and stored in the external device as a dynamic prescription, or DynamicRx™. The prescribed therapeutic action will then be communicated to the patient on the graphic display.

In one embodiment, the patient signaling apparatus will prompt the patient to confirm that each prescribed therapy has been performed. For example, if the therapy is taking a specific dose of oral medication, the patient will be prompted to press a button on the graphical interface when the medication has been taken. In one embodiment of the invention, this information is used to keep track of the number of pills remaining since the last time the patient's prescription was filled, so that the patient or caregiver can be reminded when it is time to refill the prescription.

As an example of a DynamicRx™ for a congestive heart failure patient, the level and rate of change of left atrial blood pressure (LAP) may be used by the physician to determine the dosage of diuretic. If the LAP remains in the normal range for that patient, the patient signaling device would display the normal dosage of diuretic. As in Example 1 above, if the LAP falls below the patient's normal range, the doctor may prescribe a reduction or withholding of diuretic, and that instruction would appear on the graphical interface. In another embodiment of a DynamicRx™ the patient may be instructed to take some other kind of action, such as calling the physician or caregiver, altering diet or fluid intake, or getting additional rest. Thus, the apparatus and methods of the present invention allow the physician to conditionally prescribe therapy for the patient, and to communicate the appropriate therapy to the patient in response to dynamic changes in the patient's medical condition.

In one embodiment, the physician enters the therapeutic plan for the patient, e.g., the DynamicRx™, on a personal computer and the DynamicRx™ is then loaded from the PC into the patient advisory module. In one embodiment, the patient advisory module is a PDA using the PALM OS® (Palm Computing, Inc.), or like, operating system and the DynamicRx™ is loaded from the physician's PC via the HOTSYNC® (Palm Computing, Inc.), or like, facility of PALM OS®. Loading of the DynamicRx™ from the physician's PC could be performed in the physician's office, or could be performed over a telephone modem or via a computer network, such as the Internet.

In one embodiment, DynamicRx™ software running on the PC contains treatment templates that assist the physician in creating a complete DynamicRx™, such that appropriate therapies/actions are provided for all possible values of the patient's physiological parameters.

In one embodiment of the present invention, the DynamicRx™ includes a patient instruction. In one embodiment, the patient instruction may includes directions or instructions to take medications, instructions to call 911, instructions to rest; or instructions to call a physician or medical care provider. In another embodiment of the present invention, one or more devices are provided to enable a physician or medical care provider to provide instruction to the patient. These devices include, but are not limited to, workstations, templates, PC-to-Palm hotsync operations, uploading processes, downloading processes, linking devices, wireless connections, networking, data cards, memory cards, and interface devices that permit the physician instruction to be loaded onto a patient's signal processor. In another embodiment, a user instruction is provided, where the user includes a patient, a physician, or a third party.

C. Example 3

Heart failure patients implanted with the embodiments described in the above two examples may at the time of such implantation, or subsequently develop a medical indication for concurrent implantation of a CRM device. For example, required heart failure treatment with beta-blocking medication may slow the heart rate sufficiently to induce symptoms such as fatigue, or may prevent the heart rate from increasing appropriately with exertion, a condition known as chronotropic incompetence. These conditions are recognized indications for atrial pacing or atrial pacing with a rate responsive type of pacemaker. Normally this involves the placement of a pacemaker generator and an atrial pacing lead usually positioned in the right atrial appendage. In many cases, a dual chamber pacemaker is placed to synchronously pace the right atrium via one lead and the right ventricle via a second pacing lead. In other cases, such heart failure patients may have an abnormality of electrical conduction within the heart such as is known to occur with a condition called left-bundle branch block that causes dysynchronous left ventricular contraction thereby worsening heart failure. Implantation of a biventricular pacemaker has been shown to improve many of these patients. Because severe heart failure also carries an increased risk of sudden cardiac death due to a ventricular cardiac tachyarrhythmia, many of these patients are now being treated with implantable cardiac defibrillators (ICD's). In some cases combination rhythm management devices comprised of a biventricular pacemaker and an ICD are implanted.

In such cases where a CRM device is needed, it would be beneficial to the patient if the rhythm management device were integrated with the heart failure management devices described by Eigler, et al., in U.S. Pat. No. 6,328,699 and U.S. Patent Application Publication Nos. 2003/0055344 and 2003/0055345, all of which are incorporated by reference in their entireties, to utilize the sensing lead yielding a pressure indicative of left atrial pressure additionally as an atrial pacing lead. It would be further beneficial if the LAP sensing lead system described in Example 2 could be upgraded to combination heart failure management/CRM device by replacing the coil antenna with an appropriately integrated CRM generator without removing or changing the LAP sensing lead.

In one embodiment, the implanted heart failure device of Example 2 above is modified by replacing the implanted communications coil with an appropriately integrated CRM generator and additional pacing/ICD leads. The LAP sensing lead is connected as the atrial pacing lead to the generator. The generator has appropriate circuitry to power the sensing circuitry of the atrial lead. LAP is read out by telemetry between the external PDA and the telemetry coil in the housing of the integrated rhythm management generator. If clinically appropriate, right and left ventricular pacing or defibrillation leads can be placed and connected to the generator. There are many potential benefits from such a combined rhythm and heart failure management system in addition to the clinical benefits from each individual system. Fewer leads need to be placed in the heart and a single venous insertion site can be used with the combined system. Atrial pacing from the intra-atrial septum has been show to inhibit paroxysmal atrial fibrillation, an arrhythmia common in heart failure patients. Patients can be titrated to higher or more appropriate beta-blocker dose levels with potentially increased survival benefits. Additionally, the LAP sensor can be used to control pacing parameters. As described above, the LAP waveform may be helpful in adjusting mechanical left-sided AV delay to optimize LV filling. Also, when LAP is within the desired normal range and thus the patient is not in acute heart failure, synchronous ventricular pacing can be inhibited to prolong battery life. It is understood by those skilled in the art, such as cardiologists and cardiac surgeons, that there may be additional clinical benefits bestowed by the combination of heart failure and rhythm management devices.

While the inventions disclosed herein have been particularly shown and described with references to embodiments thereof, it will be understood by those skilled in the art that various changes in form and details may be made therein without departing from the scope of the inventions disclosed herein. For all of the embodiments described above, the steps of the methods need not be performed sequentially.

What is claimed is:

1. A cardiac rhythm management device configured to be implanted within a medical patient, the cardiac rhythm management device comprising:
    a proximal component comprising a first energy storage device;
    a lead connected to the proximal component;
    a distal component connected to the lead, the distal component implantable within a patient's heart, the distal component comprising a second energy storage device configured to receive electrical energy from the first energy storage device of the proximal component and to store the electrical energy; and
    a control module configured to cause the second energy storage device to deliver at least a portion of the stored electrical energy as one or more electrical pulses to the patient's heart, thereby managing a cardiac rhythm in the patient.

2. The cardiac rhythm management device of claim 1, wherein the second energy storage device comprises a capacitor.

3. The cardiac rhythm management device of claim 1, wherein the second energy storage device comprises a battery.

4. The cardiac rhythm management device of claim 1, wherein the control module comprises a processor.

5. The cardiac rhythm management device of claim 1, further comprising a pacing electrode, wherein the control module is further configured to cause the second energy storage device to deliver at least a portion of the stored electrical energy to the patient's heart via the pacing electrode.

6. The cardiac rhythm management device of claim 1, wherein the control module is further configured to control the transfer of energy from the first energy storage device to the second energy storage device.

7. The cardiac rhythm management device of claim 1, wherein the distal component further comprises a pressure sensor configured to sense a pressure of the patient's heart.

8. A method of managing a cardiac rhythm in a medical patient, the method comprising:
- providing a proximal component configured to be implanted in a patient, the proximal component operative to store energy;
- providing a distal component configured to be implanted in the patient's heart;
- providing a lead configured to be implanted in the patient, the lead operative to couple the proximal and distal components;
- providing a controller configured to:
  - transfer at least a portion of the stored energy from the proximal component to the distal component;
  - store the transferred energy in the distal component;
  - deliver at least a portion of the transferred energy stored in the distal component as one or more electrical pulses to the patient's heart.

9. The method of claim 8, wherein said controller is further configured to transfer the energy by transferring at least a portion of the stored energy through one or more digital signals.

10. The method of claim 9, wherein the one or more digital signals comprise a digital power interval portion and a digital instruction interval portion.

11. The method of claim 8, wherein the controller is further configured to receive physiological data from a physiological sensor.

12. The method of claim 11, wherein the sensor comprises a pressure sensor configured to obtain a pressure signal indicative of a pressure of the heart.

13. The method of claim 11, wherein the distal component is further configured to communicate the physiological data to the proximal component.

14. The method of claim 8, wherein the controller is further configured to deliver at least a portion of the transferred energy by at least delivering the one or more electrical pulses to the heart using a pacing electrode.

15. The method of claim 8, wherein the proximal component comprises the controller.

16. The method of claim 8, wherein the distal component comprises the controller.

17. An apparatus configured to be implemented within a medical patient for managing cardiac health of the patient, the apparatus comprising:
- a proximal housing adapted to be implanted in a location external to a patient's heart;
- a lead connected to the proximal housing;
- a distal module connected to the lead;
- the lead comprising one or more electrical conductors configured to communicate electrical energy from the proximal housing to the distal module; and
- the distal module comprising an energy storage device configured to:
  - receive the electrical energy from the lead,
  - store the electrical energy, and
  - provide at least a portion of the stored electrical energy as one or more electrical pulses to the patient's heart.

18. The apparatus of claim 17, wherein the lead is configured to communicate one or more digital signals between the proximal component and the distal component.

19. The apparatus of claim 17, further comprising a control module configured to cause the energy storage device to provide at least a portion of the stored electrical energy as one or more electrical pulses to the patient's heart.

20. The apparatus of claim 19, wherein the control module is further configured to control the communication of electrical energy from the proximal housing to the energy storage device.

* * * * *